US008746877B2

(12) United States Patent
Belbey et al.

(10) Patent No.: US 8,746,877 B2
(45) Date of Patent: Jun. 10, 2014

(54) EYEWEAR WITH ENHANCED BALLISTIC RESISTANCE

(71) Applicant: Oakley, Inc., Foothill Ranch, CA (US)

(72) Inventors: Jason Belbey, Fullterton, CA (US); Steve Oldham, Corona, CA (US); Hans Karsten Moritz, Foothill Ranch, CA (US); Jason Hutchison, San Clemente, CA (US); Chad McCormick, Foothill Ranch, CA (US)

(73) Assignee: Oakley, Inc., Foothill Ranch, CA (US)

( * ) Notice: Subject to any disclaimer, the term of this patent is extended or adjusted under 35 U.S.C. 154(b) by 0 days.

(21) Appl. No.: 13/925,048

(22) Filed: Jun. 24, 2013

(65) Prior Publication Data
US 2013/0286345 A1 Oct. 31, 2013

Related U.S. Application Data

(60) Division of application No. 13/020,747, filed on Feb. 3, 2011, now Pat. No. 8,469,510, which is a continuation-in-part of application No. 12/648,232, filed on Dec. 28, 2009, now Pat. No. 8,192,015.

(60) Provisional application No. 61/143,645, filed on Jan. 9, 2009, provisional application No. 61/266,804, filed on Dec. 4, 2009.

(51) Int. Cl.
*G02C 1/00* (2006.01)
(52) U.S. Cl.
USPC ............................................. 351/156; 351/43
(58) Field of Classification Search
CPC ............... G02B 2027/0178; G02B 27/017; G02B 27/0093; A63B 33/002; A63B 33/00; A63B 2033/004; A63B 71/10

USPC ............ 351/156, 157, 153, 158, 41, 43; 2/13, 2/15, 427, 431, 435, 436, 437, 439, 452
See application file for complete search history.

(56) References Cited

U.S. PATENT DOCUMENTS

| 1,308,477 A | 7/1919 | Blanchard |
| 1,918,954 A | 7/1933 | Baker |

(Continued)

FOREIGN PATENT DOCUMENTS

| EP | 0 121 018 | 10/1984 |
| EP | 0496 292 | 1/1991 |

(Continued)

OTHER PUBLICATIONS

International Search Report and Written Opinion in related International Application No. PCT/US2012/020211, mailing date of May 25, 2012, in 18 pages.

(Continued)

*Primary Examiner* — Hung Dang
(74) *Attorney, Agent, or Firm* — Knobbe Martens Olson & Bear, LLP

(57) ABSTRACT

Eyewear is provided that can comprise a frame, a lens, and at least one retention component that can secure the lens relative to the frame. The frame can be configured to support at least one lens in a field of view of a wearer. The retention component can be supported by the frame and/or the lens and can be movable or fixed relative to the frame and/or the lens. In some embodiments, the retention component can slidably engage an engagement portion of the frame and/or the lens for preventing the lens from separating from the frame in response to a ballistic event. In some embodiments, the eyewear can comprise a faceplate and a pair of straps that attach to the frame of the eyewear in a manner that evenly distributes compressive stresses across the surface of the faceplate.

12 Claims, 31 Drawing Sheets

(56) References Cited

U.S. PATENT DOCUMENTS

| | | |
|---|---|---|
| 1,942,393 A | 1/1934 | Baker |
| 1,943,910 A | 1/1934 | Baker |
| 2,443,422 A | 6/1948 | Hansen |
| 2,652,746 A | 12/1950 | Shanks |
| 2,610,323 A | 9/1952 | Johnson |
| 2,799,862 A | 7/1957 | Rowe |
| 3,214,767 A | 11/1965 | Weber |
| 3,229,303 A | 1/1966 | Jonassen |
| 3,383,707 A | 5/1968 | McNeill |
| 3,395,964 A | 8/1968 | Chartrice |
| 3,552,840 A | 1/1971 | Braget |
| 3,691,565 A | 9/1972 | Galonek |
| 3,826,564 A | 7/1974 | Werling, Sr. |
| 3,829,201 A | 8/1974 | Whiting |
| 3,931,646 A | 1/1976 | Loughner |
| 4,056,853 A | 11/1977 | Bottazzini et al. |
| 4,176,921 A | 12/1979 | Matthias |
| 4,264,987 A | 5/1981 | Runckel |
| 4,304,469 A | 12/1981 | Solomon |
| 4,314,814 A | 2/1982 | Deroode |
| 4,340,282 A | 7/1982 | Murakami |
| 4,357,080 A | 11/1982 | Solomon |
| 4,471,496 A | 9/1984 | Gardner, Jr. et al. |
| 4,515,448 A | 5/1985 | Tackles |
| 4,527,291 A | 7/1985 | Nussbickl |
| 4,616,367 A | 10/1986 | Jean et al. |
| 4,662,966 A | 5/1987 | Sumi et al. |
| 4,670,084 A | 6/1987 | Durand |
| 4,686,712 A | 8/1987 | Spiva |
| 4,715,702 A | 12/1987 | Dillon |
| 4,759,622 A | 7/1988 | Schmidthaler |
| 4,813,775 A | 3/1989 | Kaksonen |
| 4,822,158 A | 4/1989 | Porsche |
| 4,843,655 A | 7/1989 | Hegendorfer |
| 4,859,048 A | 8/1989 | Jannard |
| 4,867,550 A | 9/1989 | Jannard |
| 4,901,374 A | 2/1990 | Van der Woude |
| 4,951,322 A | 8/1990 | Lin |
| 4,983,030 A | 1/1991 | Chandler |
| 5,016,293 A | 5/1991 | Lickle |
| 5,048,944 A | 9/1991 | Porsche |
| 5,056,163 A | 10/1991 | Chou |
| 5,069,541 A | 12/1991 | Holmes et al. |
| 5,144,344 A | 9/1992 | Takahashi et al. |
| 5,182,586 A | 1/1993 | Bennato |
| 5,182,587 A | 1/1993 | Hyoi |
| 5,208,614 A | 5/1993 | Jannard |
| 5,257,050 A | 10/1993 | Wiedner |
| 5,270,743 A | 12/1993 | Hofmair et al. |
| 5,308,426 A | 5/1994 | Claveau |
| 5,357,292 A | 10/1994 | Wiedner |
| 5,373,331 A | 12/1994 | Vallalla et al. |
| 5,379,463 A | 1/1995 | Schleger et al. |
| 5,390,369 A | 2/1995 | Tubin |
| 5,400,089 A | 3/1995 | Danloup et al. |
| 5,410,763 A | 5/1995 | Bolle |
| 5,418,580 A | 5/1995 | Sondrol |
| 5,423,092 A | 6/1995 | Kawai |
| 5,455,639 A | 10/1995 | Magdelaine et al. |
| 5,467,148 A | 11/1995 | Conway |
| 5,536,828 A | 7/1996 | Deluca et al. |
| 5,541,674 A | 7/1996 | Jannard |
| 5,576,775 A | 11/1996 | Bolle |
| 5,583,583 A | 12/1996 | Wilson |
| 5,587,747 A | 12/1996 | Bernheiser |
| 5,602,603 A | 2/1997 | Bondet |
| 5,610,668 A | 3/1997 | Mage |
| 5,617,588 A | 4/1997 | Canavan et al. |
| 5,638,145 A | 6/1997 | Jannard et al. |
| 5,641,372 A | 6/1997 | Okuno |
| 5,648,832 A | 7/1997 | Houston et al. |
| 5,652,954 A | 8/1997 | Paiement et al. |
| 5,657,106 A | 8/1997 | Herald et al. |
| 5,689,323 A | 11/1997 | Houston et al. |
| 5,708,489 A | 1/1998 | Jannard |
| 5,752,280 A | 5/1998 | Hill |
| 5,760,866 A | 6/1998 | Wedeck et al. |
| 5,765,223 A | 6/1998 | McCausland |
| 5,768,716 A | 6/1998 | Porsche |
| 5,790,230 A | 8/1998 | Sved |
| 5,798,017 A | 8/1998 | Claveau |
| 5,802,622 A | 9/1998 | Baharad et al. |
| 5,805,261 A | 9/1998 | Houston et al. |
| 5,809,580 A | 9/1998 | Arnette |
| 5,815,235 A | 9/1998 | Runckel |
| 5,862,529 A | 1/1999 | Moodie et al. |
| 5,898,469 A | 4/1999 | Wang |
| 5,914,767 A | 6/1999 | Wedeck et al. |
| 5,929,963 A | 7/1999 | McNeal |
| 5,963,293 A | 10/1999 | Jannard |
| 5,969,789 A | 10/1999 | Houston et al. |
| 5,971,536 A | 10/1999 | Chiu |
| 6,009,564 A | 1/2000 | Tackles et al. |
| 6,010,217 A | 1/2000 | Houston et al. |
| 6,010,218 A | 1/2000 | Houston et al. |
| D428,620 S | 7/2000 | Maturaporn |
| 6,086,199 A | 7/2000 | Holland et al. |
| 6,102,033 A | 8/2000 | Baribeau |
| 6,106,116 A | 8/2000 | Houston et al. |
| 6,119,279 A | 9/2000 | Haslbeck |
| 6,168,271 B1 | 1/2001 | Houston et al. |
| 6,193,367 B1 | 2/2001 | Lee |
| 6,224,209 B1 | 5/2001 | Chen |
| 6,250,756 B1 | 6/2001 | Jannard |
| 6,273,564 B1 | 8/2001 | Wedeck et al. |
| 6,276,794 B1 | 8/2001 | Chiang |
| 6,282,727 B1 | 9/2001 | Lindahl |
| 6,296,357 B1 | 10/2001 | Bof |
| 6,349,422 B1 | 2/2002 | Schleger et al. |
| 6,357,873 B1 | 3/2002 | Spindelbalker |
| 6,428,165 B1 | 8/2002 | Rivera |
| 6,464,353 B1 | 10/2002 | Spindelbalker |
| 6,477,717 B1 | 11/2002 | Winefordner et al. |
| 6,533,412 B1 | 3/2003 | Wang et al. |
| 6,550,912 B2 | 4/2003 | Vitaloni |
| 6,561,647 B1 | 5/2003 | Chen |
| 6,637,877 B1 | 10/2003 | Hartley et al. |
| 6,712,465 B2 | 3/2004 | Teng |
| 6,715,157 B2 | 4/2004 | Mage |
| 6,732,383 B2 | 5/2004 | Cleary et al. |
| 6,742,890 B1 | 6/2004 | Teng |
| 6,742,891 B2 | 6/2004 | Chen |
| 6,749,299 B1 | 6/2004 | Hsu |
| 6,786,592 B2 | 9/2004 | Rivera |
| 6,804,835 B2 | 10/2004 | Chou |
| 6,834,951 B2 | 12/2004 | Xie |
| 6,863,395 B1 | 3/2005 | Teng |
| 6,877,169 B2 | 4/2005 | Acquaviva |
| 6,923,537 B2 | 8/2005 | Hartley et al. |
| 6,926,404 B2 | 8/2005 | Bassahon et al. |
| 6,928,663 B1 | 8/2005 | Tappeiner |
| 6,929,364 B1 | 8/2005 | Jannard |
| 6,948,813 B2 | 9/2005 | Parks |
| 6,959,988 B1 | 11/2005 | Sheldon |
| 6,964,067 B1 | 11/2005 | Hartman |
| 6,964,477 B1 | 11/2005 | Teng |
| 7,000,263 B2 | 2/2006 | McNeal |
| 7,003,802 B2 | 2/2006 | Broersma |
| 7,036,152 B2 | 5/2006 | Gafforio et al. |
| 7,090,346 B2 | 8/2006 | Tsai |
| 7,100,215 B2 | 9/2006 | Shiue |
| 7,137,426 B2 | 11/2006 | Neri et al. |
| 7,137,700 B2 | 11/2006 | DiChiara et al. |
| 7,150,525 B1 | 12/2006 | Yang |
| 7,163,289 B2 | 1/2007 | Wedeck et al. |
| 7,200,875 B2 | 4/2007 | Dondero |
| 7,219,992 B1 | 5/2007 | Wu |
| 7,219,993 B1 | 5/2007 | Chiou |
| 7,222,958 B1 | 5/2007 | Chiou |
| 7,222,959 B2 | 5/2007 | Jannard |
| 7,234,808 B2 | 6/2007 | Bruck |
| 7,241,007 B2 | 7/2007 | Cody |
| 7,261,410 B1 | 8/2007 | Chen |
| 7,267,737 B2 | 9/2007 | Neri et al. |

(56) References Cited

U.S. PATENT DOCUMENTS

| | | | |
|---|---|---|---|
| 7,328,999 | B2 | 2/2008 | Zelman |
| 7,343,631 | B2 | 3/2008 | Lin |
| 7,390,086 | B2 | 6/2008 | Lee |
| 7,396,124 | B1 | 7/2008 | Wang |
| 7,425,065 | B2 | 9/2008 | Wang |
| 7,452,069 | B2 | 11/2008 | Lipawsky |
| 7,478,906 | B2 * | 1/2009 | Fielding, Jr. .................. 351/156 |
| 7,481,529 | B1 | 1/2009 | Chen |
| 7,497,569 | B2 | 3/2009 | Webb |
| 7,520,217 | B2 | 4/2009 | Roberts et al. |
| 7,520,605 | B1 | 4/2009 | Chen |
| 7,553,013 | B2 | 6/2009 | Tsai |
| 7,563,341 | B2 | 7/2009 | Ferguson et al. |
| 7,585,072 | B1 | 9/2009 | Wang-Lee |
| 7,585,073 | B2 * | 9/2009 | Paolino ........................ 351/158 |
| 7,604,346 | B2 * | 10/2009 | Wang ............................ 351/43 |
| 7,681,257 | B1 | 3/2010 | Broersma |
| 7,686,449 | B2 | 3/2010 | Jannard et al. |
| D616,485 | S | 5/2010 | Thixton |
| 7,712,894 | B2 | 5/2010 | Tsai |
| 7,712,896 | B1 | 5/2010 | Lee |
| 7,725,959 | B2 | 6/2010 | Wang-Lee |
| D622,303 | S | 8/2010 | Thixton |
| 7,810,174 | B2 | 10/2010 | Matera |
| 7,850,301 | B2 | 12/2010 | DiChiara |
| 7,856,673 | B2 | 12/2010 | Reed |
| 7,887,181 | B1 | 2/2011 | Chen |
| 7,954,942 | B2 | 6/2011 | Calilung et al. |
| D649,178 | S | 11/2011 | Moritz |
| D653,697 | S | 2/2012 | Taylor |
| D653,698 | S | 2/2012 | Taylor |
| 8,192,015 | B2 | 6/2012 | Taylor et al. |
| 8,316,470 | B2 | 11/2012 | McNeal et al. |
| 8,408,695 | B2 | 4/2013 | Calilung et al. |
| 8,414,119 | B2 | 4/2013 | Yeh |
| 8,469,510 | B2 | 6/2013 | Belbey et al. |
| 8,534,830 | B2 | 9/2013 | Taylor et al. |
| 2002/0039928 | A1 | 4/2002 | Spurgeon et al. |
| 2003/0188376 | A1 | 10/2003 | Dondero |
| 2004/0139532 | A1 | 7/2004 | Parks |
| 2004/0141147 | A1 | 7/2004 | Cyr |
| 2005/0070434 | A1 | 3/2005 | Drake |
| 2005/0132478 | A1 | 6/2005 | Canavan |
| 2005/0160521 | A1 | 7/2005 | Hussey |
| 2005/0270477 | A1 | 12/2005 | Curci et al. |
| 2006/0048289 | A1 | 3/2006 | Shiue |
| 2006/0119790 | A1 | 6/2006 | Tsai |
| 2006/0179554 | A1 | 8/2006 | Barton |
| 2006/0191062 | A1 | 8/2006 | Matera |
| 2006/0256281 | A1 | 11/2006 | Li |
| 2006/0283555 | A1 | 12/2006 | Green |
| 2007/0024806 | A1 | 2/2007 | Blanshay et al. |
| 2007/0033718 | A1 | 2/2007 | Lin |
| 2007/0109490 | A1 | 5/2007 | Collier et al. |
| 2007/0121059 | A1 | 5/2007 | Chiou |
| 2007/0153230 | A1 | 7/2007 | Musal et al. |
| 2007/0200997 | A1 | 8/2007 | Jannard |
| 2007/0240812 | A1 | 10/2007 | Bortolato |
| 2007/0261782 | A1 | 11/2007 | Frye et al. |
| 2008/0036961 | A1 | 2/2008 | Zhou |
| 2008/0137028 | A1 | 6/2008 | Webb |
| 2008/0155736 | A1 | 7/2008 | Paulson et al. |
| 2008/0198323 | A1 | 8/2008 | Yu |
| 2008/0266515 | A1 | 10/2008 | Hou |
| 2008/0301858 | A1 | 12/2008 | Wang-Lee |
| 2008/0304005 | A1 | 12/2008 | DiChiara |
| 2009/0019620 | A1 | 1/2009 | Reed |
| 2009/0038057 | A1 | 2/2009 | Tews |
| 2009/0038059 | A1 | 2/2009 | McNeal et al. |
| 2009/0300830 | A1 | 12/2009 | Mage |
| 2009/0313746 | A1 | 12/2009 | Wang |
| 2010/0085533 | A1 | 4/2010 | Calilung et al. |
| 2010/0186153 | A1 | 7/2010 | Reyes et al. |
| 2010/0231850 | A1 | 9/2010 | Hones |
| 2011/0007262 | A1 | 1/2011 | Taylor et al. |
| 2011/0194065 | A1 | 8/2011 | Belbey et al. |
| 2011/0225709 | A1 | 9/2011 | Saylor et al. |
| 2011/0225710 | A1 | 9/2011 | Reyes et al. |
| 2011/0225711 | A1 | 9/2011 | Reyes et al. |
| 2011/0258758 | A1 | 10/2011 | Renaud-Goud et al. |
| 2011/0299026 | A1 | 12/2011 | Calilung et al. |
| 2012/0038879 | A1 | 2/2012 | Reyes et al. |
| 2012/0218504 | A1 | 8/2012 | Taylor et al. |
| 2012/0218507 | A1 | 8/2012 | Calilung et al. |
| 2012/0255104 | A1 | 10/2012 | Didier |
| 2013/0083285 | A1 | 4/2013 | McNeal et al. |
| 2013/0104300 | A1 | 5/2013 | Park |
| 2013/0271723 | A1 | 10/2013 | Calilung et al. |

FOREIGN PATENT DOCUMENTS

| | | |
|---|---|---|
| EP | 1810648 | 7/2007 |
| EP | 1830221 | 9/2007 |
| FR | 1126329 | 11/1956 |
| FR | 2088866 | 1/1972 |
| FR | 2626683 | 8/1989 |
| FR | 2688322 | 12/1992 |
| FR | 2684292 | 6/1993 |
| FR | 2 800 173 | 4/2001 |
| GB | 512419 | 9/1939 |
| GB | 2199155 | 6/1988 |
| GB | 2278459 | 11/1994 |
| JP | 59-79827 | 5/1984 |
| JP | 59-104127 | 7/1984 |
| JP | 219021 | 2/1990 |
| JP | 2002-228986 | 8/2002 |
| WO | WO 98/30930 | 7/1998 |
| WO | WO 03/023495 | 3/2003 |
| WO | WO 2007/049070 | 5/2007 |
| WO | WO 2010/003143 | 1/2010 |
| WO | WO2010/081043 | 7/2010 |

OTHER PUBLICATIONS

Correspondence from the International Searching Authority in corresponding PCT Application No. PCT/US2010/020551, dated Nov. 5, 2010, 7 pages.

European Search Report and Written Opinion in related European Application No. 13173649.8, mailing dated Sep. 3, 2013, in 13 pages.

European Search Report and Written Opinion in related European Application No. 13182081.3, mailing dated Oct. 15, 2013, in 8 pages.

International Search Report and Written Opinion issued in corresponding PCT Application No. PCT/US2010/020551, dated Aug. 3, 2010 in 20 pages.

International Preliminary Report on Patentability and Written Opinion of the International Searching Authority in corresponding PCT Application No. PCT/US2010/020551, dated Jul. 12, 2011 in 11 pages.

International Preliminary Report on Patentability and Written Opinion of the International Searching Authority in corresponding PCT Application No. PCT/US2012/020211, dated Aug. 8, 2013 in 11 pages.

* cited by examiner

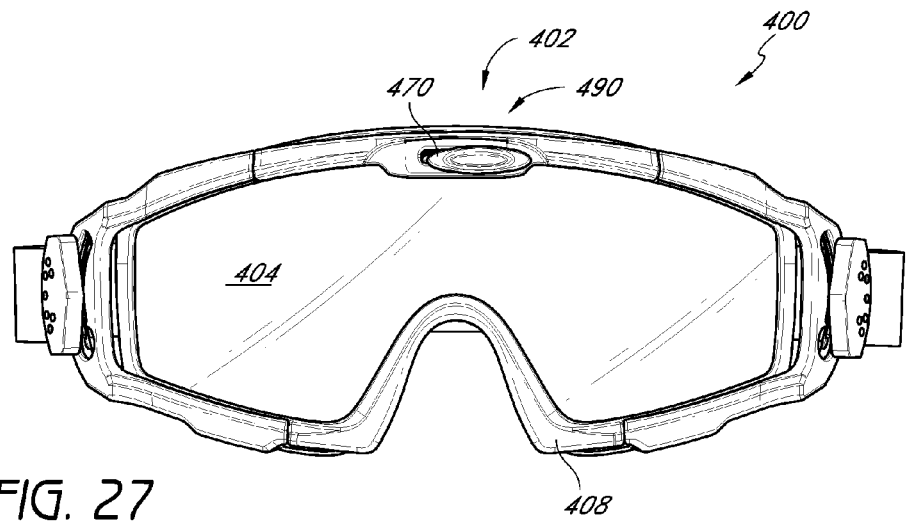
FIG. 27
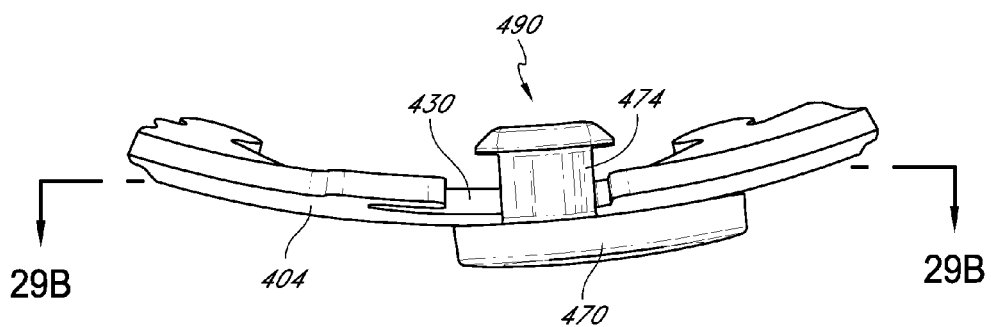
FIG. 28
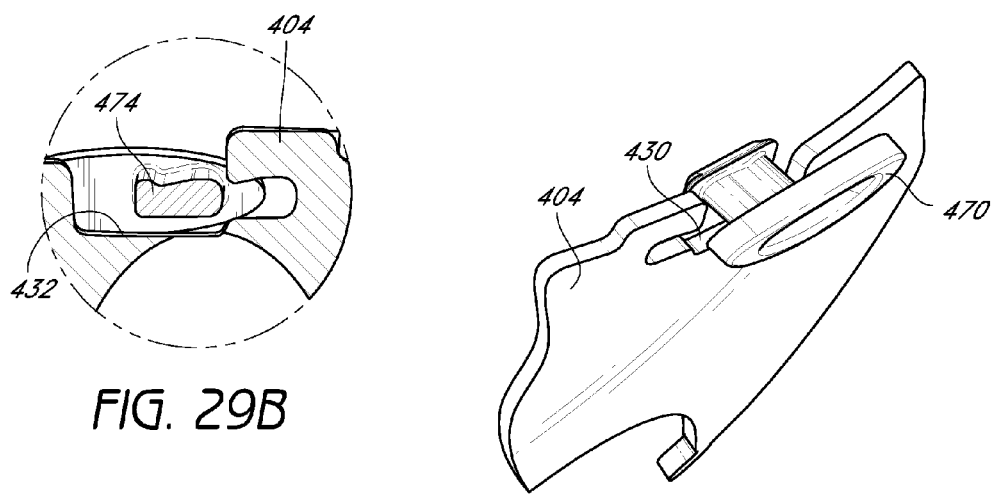
FIG. 29B
FIG. 29A

EYEWEAR WITH ENHANCED BALLISTIC RESISTANCE

CROSS-REFERENCE TO RELATED APPLICATIONS

This application is a divisional of U.S. patent application Ser. No. 13/020,747, filed on Feb. 3, 2011, now U.S. Pat. No. 8,469,510, which is a continuation-in-part of U.S. patent application Ser. No. 12/648,232, filed on Dec. 28, 2009, now U.S. Pat. No. 8,192,015, which claims the benefit of U.S. Provisional Application Nos. 61/143,645, filed Jan. 9, 2009, and 61/266,804, filed on Dec. 4, 2009, the entireties of each of which are incorporated herein by reference

BACKGROUND

1. Field of the Inventions

The present inventions relate generally to mounting systems for eyewear, and more specifically to methods and apparatuses for mounting an optical lens in a manner that provides excellent ballistic resistance and lens stability.

2. Description of the Related Art

A wide variety of improvements have been made in recent years in the eyewear field, particularly with respect to eyewear intended for use in active sports or as fashion sunglasses. These eyewear designs accomplish a variety of functional advantages, such as maximizing interception of peripheral light, reducing optical distortion and increasing the wearer's comfort level, compared to previous active sport eyewear.

Moreover, various other improvements have been made to enhance the durability and strength of eyewear. For example, various durable eyewear designs have been developed that enable eyewear to be sturdy even during accidents, impact, stress, and other forms of use or misuse. Further, lenses have also been developed that have enhanced ballistic protection. Thus, eyewear can be generally resistant to breaking, bending, or otherwise becoming unusable.

SUMMARY

A continuing objective in the field of high quality eyewear, particularly that is intended for use in high-speed action sports or military applications, is providing eyewear that exhibits superior ballistic resistance and lens stability. Various improvements have been made that enable a wearer to quickly modify their goggle or eyeglass using replaceable components and/or lenses, such by using the systems disclosed in U.S. Pat. Nos. 4,730,915, 5,387,949, and 7,347,545, the entirety of the disclosure of each of which is incorporated herein by reference. Nevertheless, at least one of the embodiments disclosed herein reflects the realization that in order to enhance the ballistic resistance and lens stability of a goggle or eyeglass, additional support can be provided to a replaceable or removable lens.

Embodiments disclosed herein provide, at least in part, a durable eyewear design for a goggle, eyeglass, or other eyewear that enables the lens to be securely retained by the frame of the eyewear. The eyewear can incorporate one or more retention components that may be used in conjunction with traditional lens mounting components, such as those in the systems disclosed in the patent references mentioned above. However, in some embodiments, the retention components can be used independent of traditional lens mounting components.

In some embodiments, in response to a ballistic event (such as an impact from a projectile and/or blunt contact with an object), the retention component can advantageously constrain the lens from sliding and/or rotational movement in all directions where the lens is engaged and/or supported by the retention component. Such a feature can be contrasted with prior art lens mounting components in that a prior art lens is generally constrained from sliding and/or rotational movement in many, but not all directions at a given point along the lens-frame border. Thus, impact from a ballistic event can cause the prior art lens to be dislodged, dislocated, or dismounted from the prior art frame.

For example, conventional detachable unitary lens systems of eyewear, such as a goggle or eyeglass, include an upper frame having a downwardly facing lens groove. The upper edge of a lens is positioned within the lens groove. The lens is retained within the groove by a first interference fit at a first lateral edge of the lens, and a second interference fit at a second lateral edge of the lens. This may provide secure mounting of the lens and good resistance to motion of the lens from side to side relative to the frame during light use of the eyewear. However, at least the center portion of the lens can be advanced downwardly and out of the lens groove during elastic reconfiguration of the eyewear following impact. Thus, at least one of the embodiments disclosed herein reflects the realization that prior art eyewear fails to provide sufficient ballistic resistance.

In contrast, embodiments disclosed herein can securely retain the lens relative to the frame during and after a ballistic impact. For example, the center portion of the lens can be fully seated within the lens groove during and following impact.

Such embodiments can be advantageous in that they allow the lens to be securely retained by the frame without undermining or ruining the optical characteristics of the lens. For example, the lens can be secured to and/or supported by the frame in a manner that preserves the as-molded geometry of the lens.

Moreover, embodiments disclosed herein can advantageously provide eyewear in which the lens can be easily removed and replaced by the wearer while enabling the wearer to mount the lens such that the lens exhibits superior ballistic resistance and the lens stability.

For example, in some embodiments disclosed herein, eyewear is provided that comprises a frame onto which at least one lens can be mounted. The lens can have an engagement portion. For example, the engagement portion can be disposed adjacent to a periphery of the lens. The eyewear can comprise at least one retention component or clip. The retention component can be mounted onto, carried, or supported by the frame and/or a lens. The retention component can be configured to engage at least a portion of the frame and/or a lens. The retention component can be configured to secure the lens relative to the frame to resist and/or prevent the lens from separating from the frame in response to a ballistic event. For example, the lens may be "separated" from the frame when any portion of the upper edge of the lens is pulled out of the lens groove.

The retention component can comprise at least one engagement structure for facilitating engagement with the lens. Further, the retention component can be a system or plurality of components that operate to engage the lens.

In some embodiments, the retention component can comprise at least one clip. The clip can be attached along the frame. The clip can be disposed at a central portion and/or lateral portion(s) of the frame, such as centered on the midline of the frame. The clip can be actuated by the wearer in order to secure a central and/or a lateral portion(s) of the lens to the frame.

For example, the frame can comprise opposing lateral terminals that interconnect with corresponding projections or detents in the lens in order to mount the lens to the frame in a mounted position while a single clip is used to secure the center portion of the lens to the frame in order to resist and/or prevent the lens from separating from the frame in response to a ballistic event. Thus, should the eyewear be subjected to unexpected forces such as would result from being dropped, knocked, or hit by a projectile, the lens will not tend to be separate from the frame. However, multiple clips can also be used to secure the lens relative to the frame along a plurality of portions of points of the lens.

In some embodiments, the clip can be rotated relative to and/or about the frame and/or the lens. In some embodiments, the clip can be translated, slid, or moved relative to the frame and/or the lens. For example, the retention component can comprise a rotating or sliding clip that can be mounted on or supported by the frame of the eyewear. In some embodiments, the retention component can comprise a rotating or sliding clip that can be mounted on, carried, or supported by the lens. The clip can be manually adjusted or actuated by the wearer. The clip can engage directly or indirectly with a portion of the frame and/or the lens. In some embodiments, one or more clips can engage directly or indirectly with a portion of a plurality of lenses, such as a dual lens system.

In some embodiments, the clip can comprise an engagement structure such as a tab that is operative to engage and/or interlock with an engagement portion or corresponding surface structure such as a recess or aperture on the frame and/or the lens.

For example, the lens can comprise an aperture or slot that can be engaged and/or supported by the tab of the clip. In some embodiments, the clip can have a first rotational/sliding position or disengaged position in which the lens can be freely removed downwardly from the frame, enabling disengagement of the lens. The clip can also have a second rotational/sliding position or engaged position in which the lens can be secured and/or supported relative to the frame such that the lens does not separate from the frame in response to a ballistic event.

The clip can have a hingeless configuration. For example, the clip can be configured as a tubular member that wraps around at least a portion of the frame. The clip can have a hingeless, rotatable configuration in which the clip rotates relative to or about at least a portion of the frame to facilitate engagement of the lens relative to the frame. The clip can also have a hingeless, sliding configuration in which the clip slides along at least a portion of the frame to facilitate engagement of the lens relative to the frame.

In some embodiments, the clip can be configured as a split ring having a gap or split. The split ring can encompass or surround a portion of the frame by wrapping around, for example, at least about 50% and/or less than or equal to about 80% of the perimeter or circumference of the portion of the frame, with approximately at least about 20% and/or less than or equal to about 50% of the clip defining the gap or split. In a rotating clip embodiment, the gap or split can be configured such that at least a portion of the lens can be received therein for securing the lens relative to the frame. In such embodiments, the tab can be disposed at one of the free ends forming the gap or split.

In some embodiments, a sliding clip embodiment can engage a slot in the lens. For example, the lens can be seated against the frame with the clip being positioned adjacent to the slot of the lens in a first or disengaged position. The clip can then be moved within the slot towards a second or engaged position, thus securing the lens relative to the frame.

In some embodiments, the clip can be configured to snap-fit onto the frame. The clip can be urged onto the frame with a portion of the frame passing through the gap or split in the clip. In some embodiments, the clip can be fabricated from a resilient material such that the clip deflects to allow enlargement of the gap or split such that the clip can attach to the frame. The clip can therefore be attachable to the frame without requiring pins, latches, or other components. Embodiments disclosed herein can thus allow for superior assembly and maintenance of the eyewear compared to other designs. Further, the design can be durable and sturdy, providing capable and secure retention despite stresses or other forces that may act on the eyewear.

Further, the clip can rotate with the gap or split being moved from a first rotational position or disengaged position in which a portion of the lens can be received into the gap or split to a second rotation position or engaged position in which the gap or split is rotated such that the clip engages a portion of the lens. Rotation of the gap or split can enable quick and secure engagement with the lens.

In some embodiments, the clip can define an outer profile that tapers and blends with the surface of the frame. For example, the clip can define a contour or external shape that blends with a contour or external shape of the frame. In some embodiments, the contour or external shape can blend in only one of the first or second rotational positions. For example, a mismatch in contour can provide a visible and tactile indication that the clip is in a disengaged position while the clip and frame have a generally or substantially uniform, smooth contour when the clip is in the engaged position.

In some embodiments, the clip can rotate about and/or slide along a horizontal axis such that the tab moves in a generally anterior-posterior direction to engage the lens. For example, the tab can be rotated about a generally horizontal axis that extends laterally or in a side-to-side direction in order to allow the tab to be aligned with a portion of the lens to engage the lens. Further, the tab can be moved along the frame within a generally vertical anterior-posterior plane to align with the lens to engage the lens.

In some embodiments, the clip can rotate about and/or slide along a vertical axis. In such embodiments, the tab can be rotated within a generally horizontal plane to align with the lens in a generally vertical plane to engage the lens.

For example, the engagement structure of the retention component can comprise a tab that is pivotally coupled to the frame such that the tab can rotate about a vertical axis. Optionally, the retention component can comprise a shaft that couples the retention component to the frame. Further, the retention component can optionally comprise an actuating element that is in mechanical communication with the tab such that the actuating element can be used to rotate the tab.

In some embodiments, the retention component can be slidably supported by the frame. The retention component can comprise a user-actuatable portion and a securing portion. The securing portion can extend from the user-actuatable portion and be supported at least partially by the frame. The securing portion can be engaged with the engagement portion of the lens. The retention component can be movable relative to the frame and relative to the lens to engage the securing portion with the engagement portion of the lens for preventing the lens from separating from the frame in response to a ballistic event.

In some embodiments, the frame can comprise a recess or aperture configured to receive and/or support the retention component. For example, the recess or aperture of the frame can support the retention component such that a force (exerted in at least one direction) on the retention component is transferred to the frame. The recess or aperture of the frame can optionally be configured to support the retention component such that forces exerted in several directions on the retention component are transferred to the frame.

For example, in embodiments wherein the retention component rotates about and/or slides along a horizontal axis, the retention component can engage with a horizontal section of the frame. As noted above, the engagement can be a snap-fit engagement. The retention component can fit over the horizontal section and rotate about the horizontal section. Further, the retention component can be weaved into or fit within a horizontally-extending recess or space in the frame.

For example, the frame can comprise first and second apertures. The first aperture can extend generally vertically through the frame. The second aperture can extend generally horizontally through the frame and cross or intersect the first aperture. The engagement portion of the lens can be configured to be disposed upwardly through the first aperture. The retention component can be supported by the second aperture and slidable therein. Further, the retention component can be movable between an engaged position in which the engagement portion of the lens is engaged by the retention component and a disengaged position in which the engagement portion of the lens is disengaged from the retention component.

Additionally, the retention component can slide generally laterally or side-to-side within the second aperture of the frame. Further, the engagement portion of the lens can comprise a slot that extends horizontally along the periphery of the lens. In some embodiments, the slot of the lens can extend adjacent an upper edge of the lens, and the first and second apertures can be disposed through an upper portion of the frame. The slot can also extend in a vertical direction along a portion of the length thereof and in a horizontal direction along a remaining portion of the length thereof. In some embodiments, the engagement portion of the lens can comprise a locking mechanism for locking the retention component in a given position, such as in an engaged position. In some embodiments, the engagement portion of the lens can comprise a biasing mechanism for biasing the retention component toward a given position, such as toward the engaged position.

Additionally, in embodiments wherein the retention component rotates about and/or slides along a vertical axis, the retention component can engage with a vertical section of the frame. For example, the retention component can fit over the vertical section and rotate about the vertical section. Further, the retention component can be weaved into or fit within a vertically-extending recess or space in the frame.

The retention component can also comprise a plurality of clips disposed along the frame of the eyewear. In such embodiments, the frame of the eyewear can be configured with or without opposing terminals that are used to engage projections or detents of the lens in order to mount the lens in a mounted position. For example, the plurality of clips can be used as the sole connectors to mount and secure the lens from separating from the frame.

Furthermore, the retention component can be formed separately from the frame. For example, the retention component can be coupled to the frame and rotatable or slideable with respect to the frame. In some embodiments, the retention component can be advanced from a first orientation (or a disengaged position) to a second orientation (or an engaged position) in order to engage with the lens. For example, the frame and the retention component can also be configured to permit a predetermined range of rotational or axial movement of the retention component. In one embodiment, the frame can comprise one or more hardstop features that can enter with one or more corresponding detents or recesses in the retention component. The retention component can rotate in a given direction until a hardstop feature of the frame contacts a detents or recess of the retention component to restrict further rotation of the retention component.

For example, in embodiments in which the retention component comprises a hingeless clip, the clip can rotate between two or more rotational positions with hardstop features of the clip and the frame restraining motion of the clip at one or more of the positions. For example, the clip can be configured to comprise an interior having one or more protrusions or recesses that engage(s) with one or more protrusions or recesses of the frame. In some embodiments, the hardstop features can be hidden from view when in an assembled state. Further, engagement between the hingeless clip and the frame can also create the desired interaction between the corresponding hardstop features of the clip and the frame.

In addition, embodiments are provided in which the lens comprises an engagement portion that can be engaged and/or supported by the retention component. The engagement portion of the lens can comprise at least one of a recess, surface contour, cut-out, projection, slot, aperture, and other such surface structure formed in any variety of shapes and/or sizes. For example, in some embodiments, the engagement portion can be an aperture that extends through the thickness of the lens. The engagement structure can also be a cut-out that extends through the thickness of the lens and extends inwardly from a periphery of the lens. Further, some embodiments can be configured such that the frame comprises an engagement portion that can be engaged by a retention component that is supported by the lens.

For example, the engagement portion of the lens can comprise a hook that defines a slot and comprises a downwardly projecting portion that engages with a portion of the retention component when the retention component is in the engaged position. The portion of the retention component engaged by the hook can define a recess that is engageable with the downwardly projecting portion of the hook when the securing portion is positioned within the slot of the engagement portion.

Additionally, in some embodiments, the lens can comprises at least one protrusion or recess disposed along the periphery thereof, and the frame can comprise at least one recess or protrusion corresponding to the at least one protrusion or recess of the lens and engageable therewith. The engagement between the at least one protrusion or recess of the lens and the at least one recess or protrusion of the frame can limit at least one degree of movement of the lens relative to the frame. Further, the retention component can serve to limit at least one of the remaining degrees of movement of the lens relative to the frame.

In accordance with some embodiments, the eyewear can also be configured to comprise a faceplate, a frame, at least one lens, and a strap. The faceplate can be configured to be positioned against a wearer's head when the eyewear is worn by the wearer. The faceplate can include a foam or gasket component for enhancing comfort against the wearer's face. The frame can be coupled to the faceplate and can be configured to support the at least one lens in a field of view of a wearer. The frame can comprise first and second guide slots formed along first and second sides thereof.

Additionally, the strap can secure the eyewear to the wearer's head. The strap can comprise first and second ends and first and second strap engagement mechanisms that are attached to the respective first and second ends of the strap. The first and second strap engagement mechanisms can be slidably engagable with the first and second guide slots of the frame to transfer tensile loading of the strap to the faceplate in the form of compressive forces exerted by the faceplate against the face of the wearer for evenly or substantially evenly distributing the compressive forces along a surface of the faceplate.

In some embodiments, the faceplate can define a centroid. The horizontal centroidal axis can pass through the centroid of the faceplate. In some embodiments, the horizontal centroidal axis can be configured to be parallel or coincident with an interception axis that passes through both pupils of the eyes of the wearer. Further, the horizontal centroidal axis can be positioned posteriorly relative to the lens of the eyewear. In some embodiments, the compressive forces can define a resultant force, and the first and second strap engagement mechanisms can be slidable within the first and second guide slots of the frame to maintain the orientation of the resultant force in a direction passing through or sufficiently near the centroid of the faceplate.

In some embodiments, the first and second strap engagement mechanisms can be slidable within the first and second guide slots of the frame between a first angular position and a second angular position. Further, the orientation of the resultant force can pass generally through or sufficiently near the centroid of the faceplate for evenly or substantially evenly distributing the compressive forces along a surface of the faceplate when the strap is in either of the first or second angular positions.

In some embodiments, the first and second guide slots can define upper and lower portions. The lower portion of each guide slot can comprise an enlarged opening that is wider than the upper portion. The enlarged opening can be configured to receive a wide end portion of the first and second strap engagement mechanisms for permitting engagement between the first and second guide slots and the first and second strap engagement mechanisms. Further, the frame can comprise first and second outriggers, and the first and second outriggers can comprise the first and second guide slots.

The first and second guide slots can each further comprise a tooth being disposed above the lower portion of each guide slot and extending into each guide slot to define a gate. The first and second strap engagement mechanisms can comprise a neck extending from a body thereof. The wide end portion of the first and second strap engagement mechanisms can be disposed at a distal end of the neck. The neck can define a cross-sectional profile that is less that a width of the gate in a first rotational orientation and greater than the width of the gate in a second rotational orientation. Further, the second rotational orientation of the neck can be achieved with the strap of the eyewear in an as-worn orientation.

The first and second guide slots can define a radius of curvature each having a center point. The center points can be located along a guide axis that is generally parallel, coaxial, or coincident relative to a horizontal centroidal axis. As discussed herein, the horizontal centroidal axis can be generally parallel or coincident relative to an interception axis that can pass generally through pupils of the wearer. Further, in some embodiments, the horizontal centroidal axis can be positioned posteriorly relative to the at least one lens. Furthermore, the horizontal centroidal axis can be substantially coincident with the centroid, which can be spaced relative to various structures and geometric features of the lens, frame, faceplate, etc. within certain ranges.

In some embodiments, the guide slots can be substantially linear or straight. However, in some embodiments, the first and second guide slots can have a substantially constant or variable radius of curvature. In some embodiments, the radius can be between about 10 mm and less than or equal to about 40 mm. In some embodiments, the radius can be between about 15 mm and less than or equal to about 30 mm. In some embodiments, the radius can be about 20.8 mm. However, in some embodiments, as long as the center point of articulation is generally adjacent to or coincident with a centroidal axis, the first and second guide slots can be configured to define any desired radius of curvature to achieve a desired strap articulation.

BRIEF DESCRIPTION OF THE DRAWINGS

The abovementioned and other features of the inventions disclosed herein are described below with reference to the drawings of the preferred embodiments. The illustrated embodiments are intended to illustrate, but not to limit the inventions. The drawings contain the following figures:

FIG. 27 is a front view of the goggle of FIG. 20 wherein the retention component is in a disengaged position, according to an embodiment.

FIG. 28 is a partial top view of the lens and the retention component wherein the retention component is in the disengaged position, according to an embodiment.

FIG. 29A is a front partial perspective view of the lens and the retention component of FIG. 28.

FIG. 29B is a rear cross-sectional view of the lens and the retention component of FIG. 28 taken along lines 29B-29B.

DETAILED DESCRIPTION

Figure 1:
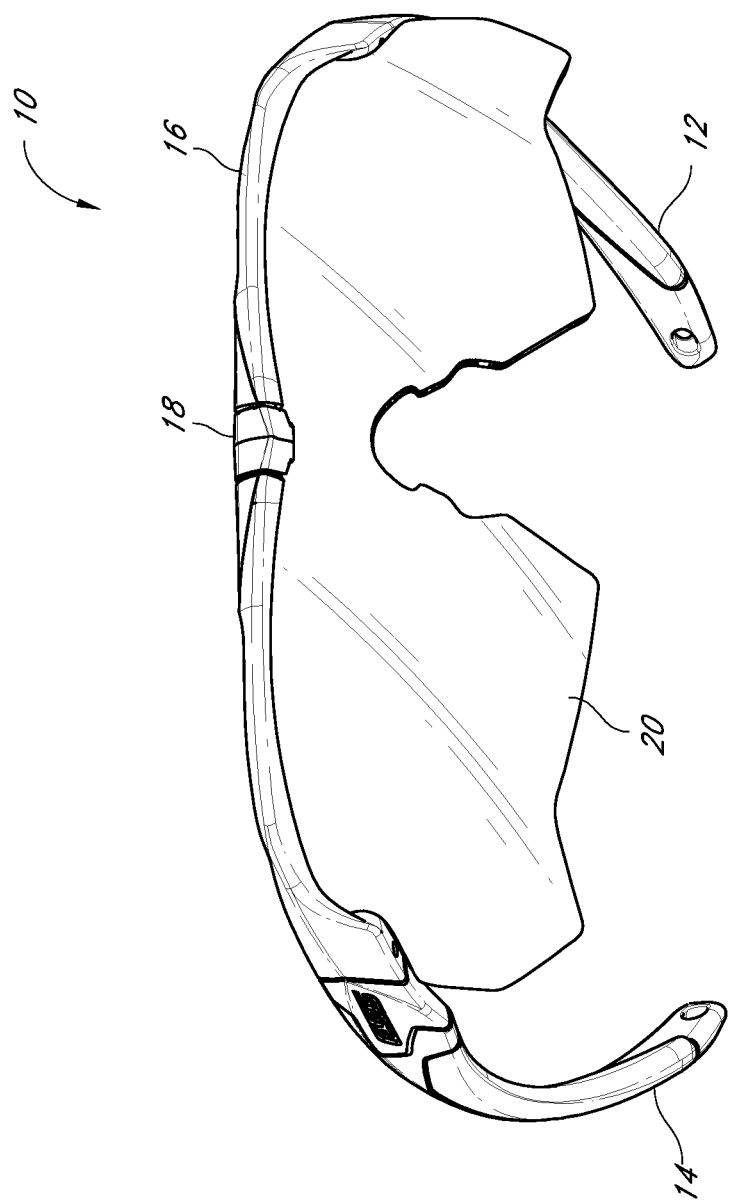
FIG. 1 is a perspective view of an eyeglass comprising a retention component for securing a lens to a frame of the eyeglass, in accordance with an embodiment of the present inventions.

While the present description sets forth specific details of various embodiments, it will be appreciated that the description is illustrative only and should not be construed in any way as limiting. Additionally, although particular embodiments of the present inventions may be disclosed or shown in the context of unitary or dual lens eyewear systems, such embodiments can be used in both unitary and dual lens eyewear systems. Further, although embodiments disclosed herein can be used with eyeglasses that have removable and replaceable lenses, embodiments are also contemplated in which the eyeglasses are not intended to provide for removable or replaceable lenses.

Further, although particular embodiments may be disclosed or shown in the context of frames having partial orbitals, such embodiments can be used with frames having both full and partial orbitals. Retention components and structures in accordance with embodiments disclosed herein can also be utilized to retain a lens or multi-lens construct within a goggle, such as a ski goggle or motocross goggle. The retention structures may be utilized either as the primary connector or as a secondary connector for cooperation with another lens retention system. Furthermore, various applications of such embodiments and modifications thereto, which may occur to those who are skilled in the art, are also encompassed by the general concepts described herein.

For example, some embodiments can provide eyewear comprising a frame and at least one retention component or structure. The frame can be configured to support at least one lens in a field of view of a wearer. The frame can comprise a first ear stem and a second ear stem. The frame can be worn on the wearer's head. The at least one retention component can be supported by the frame and/or by the at least one lens. The at least one retention component can be hingeless. The retention component can be movable relative to the frame and/or to the lens. The retention component can secure the at least one lens relative to the frame. For example, the retention component can engage an engagement portion of the lens for resisting and/or preventing the lens from separating from the frame in response to a ballistic event. Further, some embodiments can be configured such that the frame comprises an engagement portion that can be engaged by a retention component that is supported by the lens.

The retention component of the eyewear can be configured to rotate relative to the frame and/or the lens to engage the respective one of the lens and/or the frame. The retention component can be permanently or detachably mounted on the frame and/or the at least one lens. The retention component can comprise a clip disposed at a central portion of the frame. The clip can be actuated by the wearer to secure a central portion of the lens to the frame. The retention component can be movable from a first orientation in which the lens can be freely moved relative to the frame to a second orientation in which the lens is secured relative to the frame.

For example, the retention component can rotate about a generally horizontal axis relative to the frame to engage the frame and/or the lens. Further, the retention component can comprise a rotatable clip mounted on the frame and/or lens. The rotating clip can comprise an engagement structure that is operative to engage the engagement portion of the lens and/or the frame.

The rotating clip can also comprise a generally tubular or cylindrical body, and the engagement structure can comprise an engagement tab extending generally circumferentially relative to the cylindrical body. The tubular or cylindrical body can be configured to engage a recess of the frame for mounting the retention component on the frame. The tab can have a first orientation in which the lens is movable relative to the frame and a second orientation in which the tab engages the lens to the secure the lens relative to the frame. For example, the tab of the clip can engage the lens at an angle of at least about 5 degrees and/or less than or equal to about 40 degrees relative to a horizontal plane. In some embodiments, the tab of the clip can engage the lens at an angle of about 19.2 degrees relative to a horizontal plane.

Additionally, the retention component can fit over a recess of the frame to be rotatable about a longitudinal axis of the frame. For example, the retention component can fit over the recess in a snap fit. In some embodiments, the engagement portion of the lens can comprise one of a recess and an aperture that can be engaged by the engagement structure of the rotating clip.

In other embodiments, the retention component can rotate about a generally vertical axis relative to the frame to engage the frame and/or the lens. For example, the retention component can comprise an actuation handle and at least one tab being rotatable upon rotation of the handle. The tab can extend generally transversely or obliquely relative to the generally vertical axis. The tab can have a first orientation in which the lens is movable relative to the frame and a second orientation in which the tab engages the lens to the secure the lens relative to the frame. For example, the retention component can rotate in a plane that is generally coplanar with at least a portion of the lens. Additionally, the retention component can comprise an elongate shaft extending between the handle and the tab. Further, the frame can comprise a recess configured to receive at least a portion of the retention component to support the retention component relative to the frame. Furthermore, the handle can be accessible to the wearer for actuating the retention component.

In some embodiments, the frame can comprise opposing lateral terminals that interconnect with corresponding projections in the lens to mount the lens to the frame in a mounted position. The frame can comprise a lens groove. The lens groove can extend at least partially along the frame for receiving at least a portion of the lens therein.

In some embodiments, the at least one lens of the eyewear can comprise an engagement portion. Further, the frame of the eyewear can have a generally horizontal longitudinal axis and a pair of earstems extending posteriorly relative to the frame. The frame can be configured to support the at least one lens in the field of view of a wearer. Further, the eyewear can be configured such that the at least one retention mechanism is coupled to the frame and rotatable about the longitudinal axis of the frame. The retention mechanism can comprise an engagement structure extending therefrom. The engagement structure can be moveable from a first orientation in which the lens can be freely moved relative to the frame to a second orientation in which the retention structure engages the engagement portion of the lens for securing the lens relative to the frame.

The frame can also comprise at least one stop element configured to limit the rotational orientation of the retention mechanism relative to the frame. The retention mechanism can also comprise at least one stop element corresponding to the at least one stop element of the frame. The stop elements can be configured to contact each other to limit the rotational orientation of the retention mechanism relative to the frame.

In some embodiments, the retention mechanism can comprise first and second stop elements that interact with the at least one stop element of the frame. The retention mechanism can have a variety of shapes and structural features, such as including a generally cylindrical body with the engagement structure extending generally circumferentially therefrom. For example, the at least one stop element of the retention mechanism can be formed along an interior surface of the retention mechanism. Further, the at least one stop element of the retention mechanism can comprise a recess, and the at least one stop element of the frame can comprise a protrusion.

The engagement structure of the retention mechanism can comprise a tab that engages the engagement portion of the lens at an angle of between at least about 5 degrees and/or less than or equal to about 40 degrees relative to a line that is normal to the lens. Further, in some embodiments, the tab can engage the engagement portion of the lens at an angle of between at least about 10 degrees and/or less than or equal to about 20 degrees relative to a line that is normal to the lens. For example, the tab can engage the engagement portion of the lens at an angle of about 19.2 degrees.

With reference to FIG. 1, an embodiment of the present inventions is illustrated. In this embodiment, eyewear, and in particular, an eyeglass 10 is shown that comprises a pair of ear stems 12, 14, a frame 16, a retention component 18, and a lens 20. The eyeglass 10 illustrated in FIG. 1 is configured such that the lens 20 can be removed and replaced. However, in other embodiments, the lens may not be removable or replaceable. Nevertheless, such embodiments can provide increased lens stability and ballistic resistance, similar to the embodiment illustrated in FIG. 1.

Figure 2:
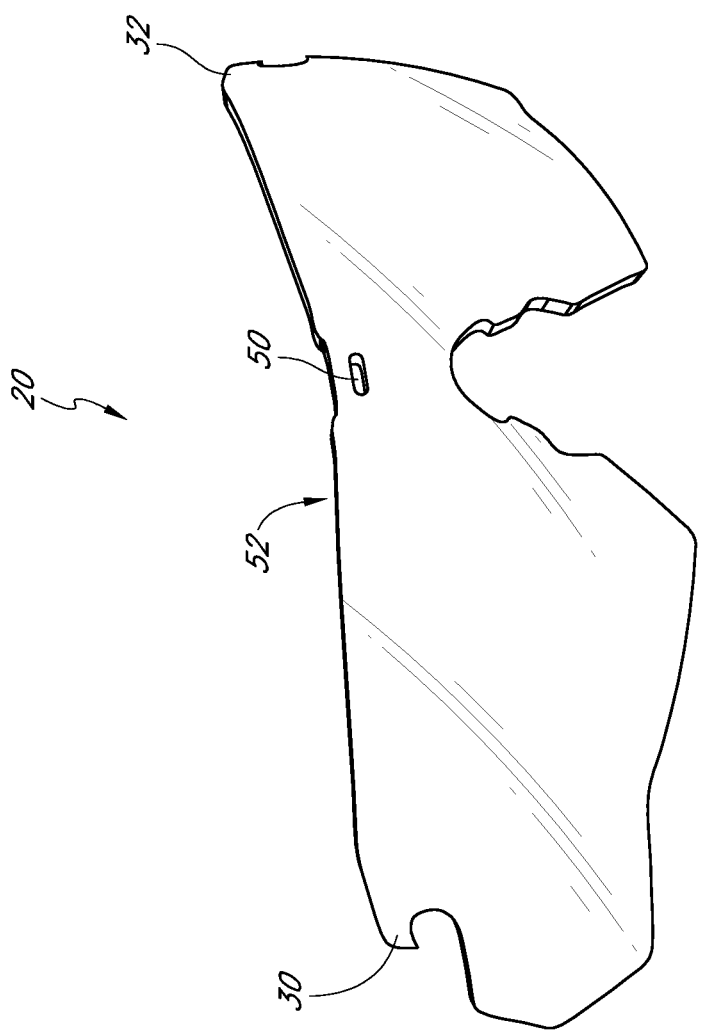
FIG. 2 is a perspective view of a lens comprising a slot that can be engaged by the retention component of the eyeglass shown in FIG. 1, according to an embodiment.
Figure 3:
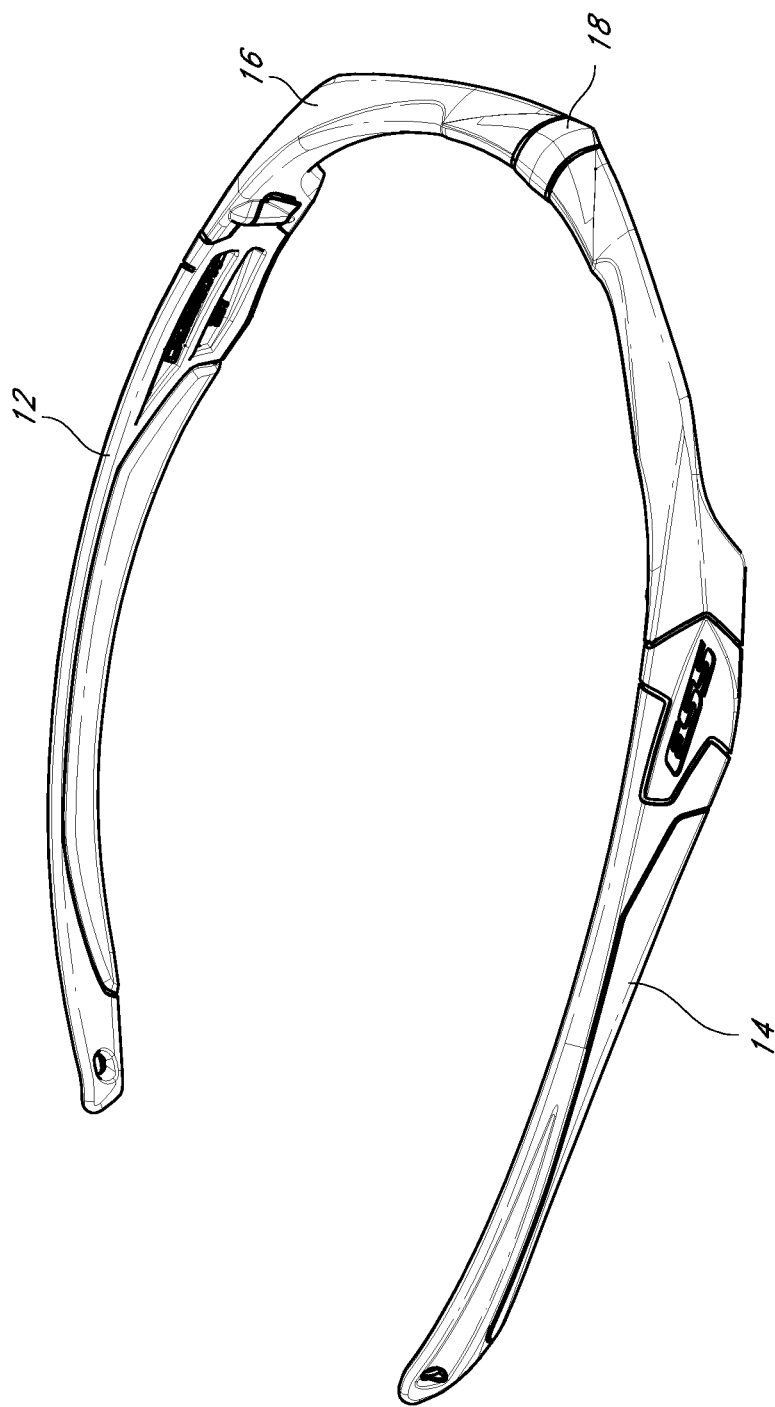
FIG. 3 is a top perspective view of the frame of the eyeglass shown in FIG. 1, according to an embodiment.

FIG. 2 illustrates an embodiment of the lens 20 for use with the eyeglass 10. The lens 20 can be configured to be supported by the frame 16. For example, the lens 20 can comprise one or more engagement portions that can be engaged with one or more retention components of the eyeglass for supporting the lens. Further, other structures can be used to support the lens. For example, the frame can comprise one or more opposing terminals and the lens can comprise one or more projections that can be fitted into the terminal(s) of the frame. However, the use of structures such as projections and terminals is optional and can be omitted in some embodiments. For example, structures in addition to the retention component(s) and engagement portion(s) may be unnecessary where two or more retention components and engagement portions are spaced apart along the edge of the lens.

As will be appreciated with reference to FIGS. 1-4, the lens 20 of the eyeglass 10 can be selectively removed and replaced by the wearer. For example, the wearer can replace the lens 20 with a lens having a different tint or shape. In some embodiments, the wearer can engage interlocking projections or detents of the lens 20 with corresponding opposing terminals of the frame 16 to remove and replace the lens 20.

Figure 4:
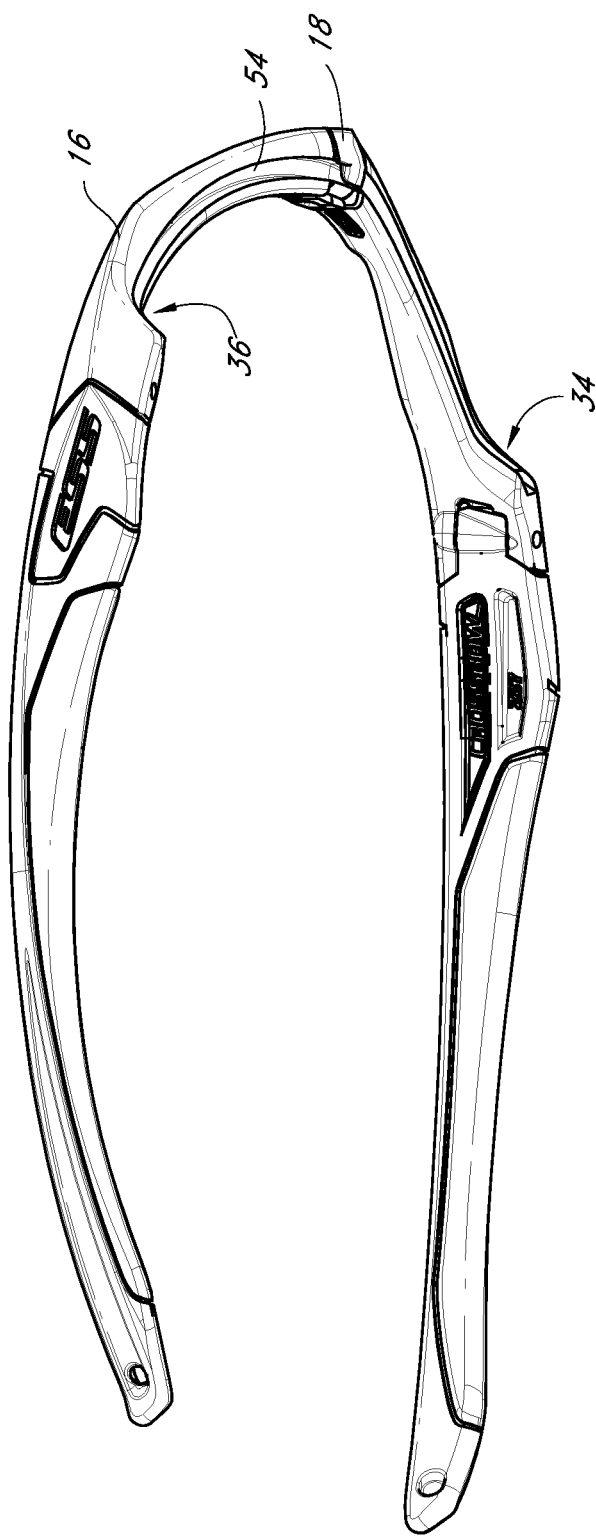
FIG. 4 is a bottom perspective view of the frame of the eyeglass shown in FIG. 1, according to an embodiment.

For example, as shown in FIGS. 2 and 4, the lens 20 can comprise a pair of projections 30, 32 that can be seated in corresponding terminal recesses 34, 36 of the frame 16. In use, when the projections 30, 32 are received within the terminal recesses 34, 36 of the frame 16, the lens 20 can be generally snap fitted into and retained within the lens groove 54 in the frame 16. Thus, in some embodiments, such an arrangement can provide a further degree of lens retention and stabilization in addition to that provided by the retention component 18.

In accordance with the embodiment shown in FIGS. 1-4, the lens 20 can also comprise an engagement portion or structure 50. The engagement portion 50 can comprise at least one portion of the lens 20 can be one of a recess, surface contour, cut-out, projection, slot, aperture, and other such surface structures and be formed in a variety of shapes and/or sizes. For example, in the illustrated embodiment, the engagement portion 50 is shown as an aperture that extends through the thickness of the lens 20. The engagement portion 50 is shown as a single aperture, but can be formed as a plurality of apertures. The engagement portion 50 can extend generally parallel or coincident relative to a line that is normal to the lens 20 (as shown for example, in FIG. 11A). Further, the engagement portion 50 can extend generally transversely or obliquely relative to a line that is normal to the lens 20 (as shown for example, in FIG. 11B).

The engagement portion 50 can be disposed at any point along the lens 20, and preferably, at any point along the lens-frame boundary 52 of the lens 20. The lens-frame boundary can be defined as the portion or portions of the lens along which the lens and the frame border, overlap, or interconnect with each other. For example, referring to FIGS. 1-2, the lens-frame boundary 52 is generally the upper section of the lens 20, adjacent to the upper edge of the lens 20 that is seated within a groove 54 of the frame 16 (shown in FIG. 4). Thus, although a single engagement portion 50 is used in the embodiment of the lens 20 shown in FIG. 2, other embodiments of the lens 20 can be constructed that comprise two or three or four or more engagement portions 50 disposed along the lens-frame boundary 52.

Additionally, as mentioned above, although the engagement portion 50 is shown as an aperture, the engagement portion 50 can also comprise a protrusion, a detent, and/or other shapes and sizes of engagement portions that allow the lens 20 to be interconnected with the retention component 18. Furthermore, as noted above, the lens 20 can comprise a unitary or dual lens system. For example, one or more engagement portions can be used in each lens of a dual lens system, as desired. Moreover, the lens 20 can be mounted within an orbital-type frame. The lens-frame boundary 52 can extend around a perimeter of the lens 20 (or the perimeters of both lenses in a dual lens system). In such embodiments, one or more engagement portions can be selectively disposed along lower portions, lateral portions, or medial portions (such as adjacent to the nosepiece opening of the lens), and the frame can also comprise corresponding retention components configured to engage the respective engagement portion(s) of the lens(es).

Figure 5:
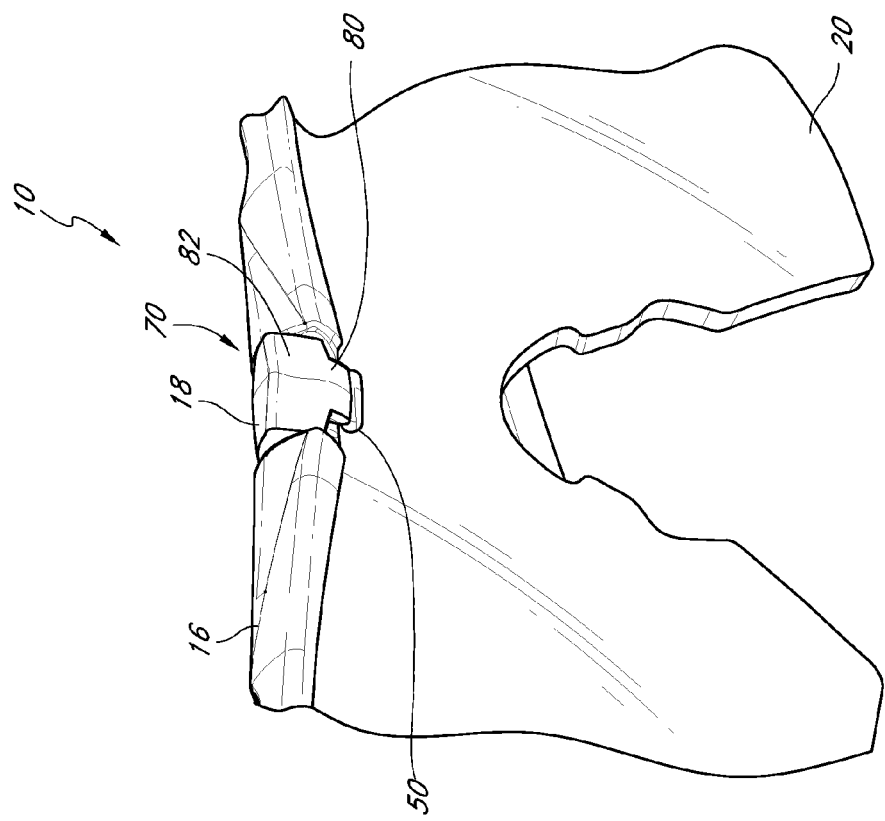
FIG. 5 is an enlarged perspective view of a medial portion of the eyeglass shown in FIG. 1, wherein the retention component is in a disengaged position, according to an embodiment.
Figure 6:
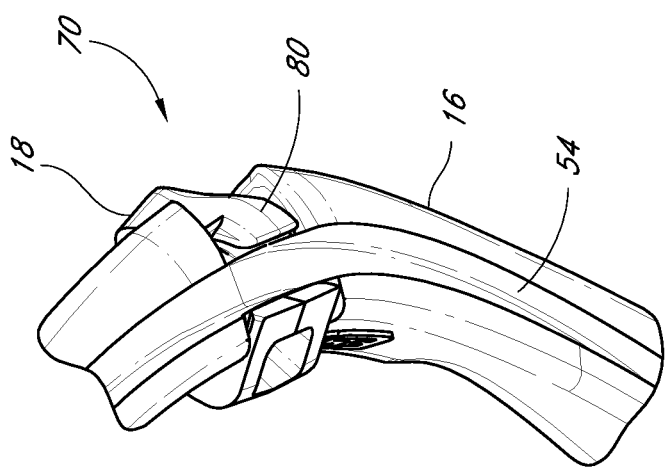
FIG. 6 is a bottom perspective view of a medial portion of the frame, wherein the retention component is in a disengaged position, according to an embodiment.
Figure 7:
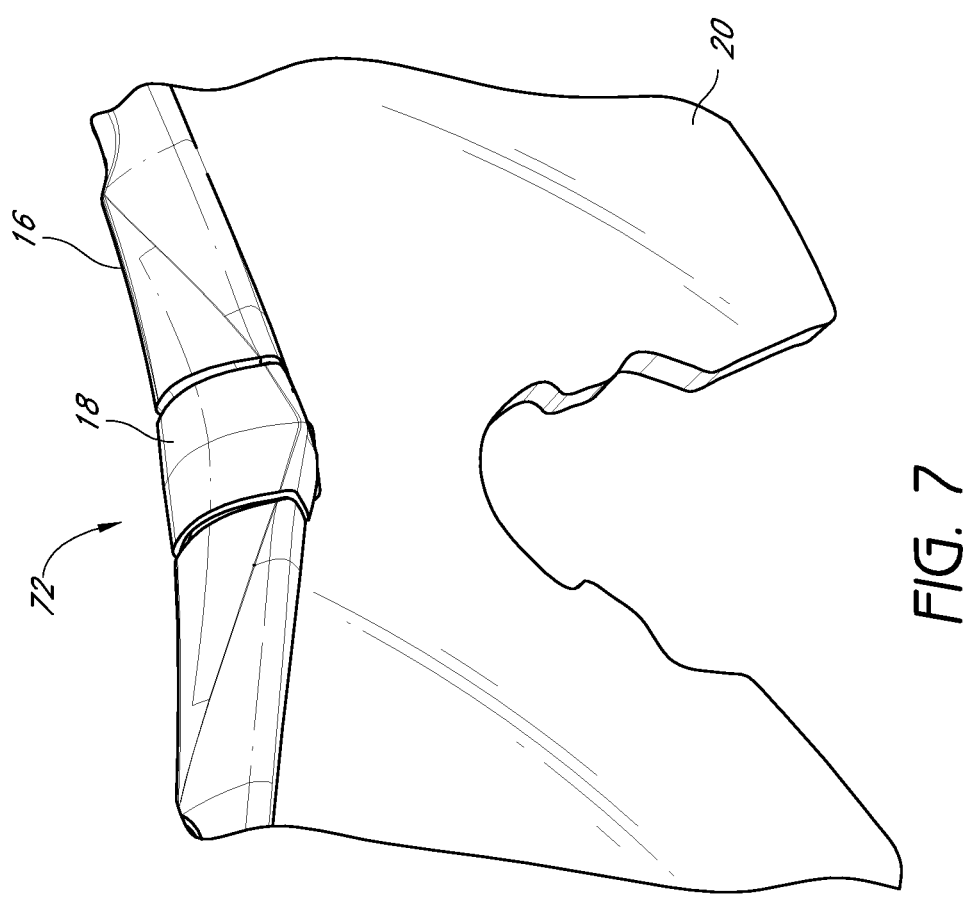
FIG. 7 is an enlarged perspective view of the medial portion of the eyeglass shown in FIG. 1, wherein the retention component is in an engaged position, according to an embodiment.

With reference to FIGS. 5-8, the function and operation of an embodiment of the retention component 18 will now be described. In FIGS. 5-6, the retention component 18 is disposed in a disengaged position 70. Additionally, in FIGS. 7-8, the retention component 18 is disposed in an engaged position 72. As will be appreciated by one skill in the art, when the retention component 18 is disposed in the disengaged position 70, the retention component 18 is not engaged with the corresponding engagement portion 50 of the lens 20. However, when the retention component is disposed in the engaged position 72, the retention component 18 can engage the engagement portion 50 of the lens 20, as shown in FIG. 7.

In order to facilitate engagement with the engagement portion 50 of the lens 20, the retention component 18 can comprise a projection or recess that engages with the corresponding engagement portion 50. As shown in FIGS. 5-8, the retention component 18 can comprise a tab 80 that extends from a body 82 of the retention component 18. In the illustrated embodiment, the tab 80 can be configured to fit within or be seated within the aperture of the engagement portion 50. The tab 80 of the retention component 18 provides an interference engagement to resist and/or prevent the lens 20 from detaching from the frame 16 or exiting the lens groove 54 of the frame 16.

Figure 8:
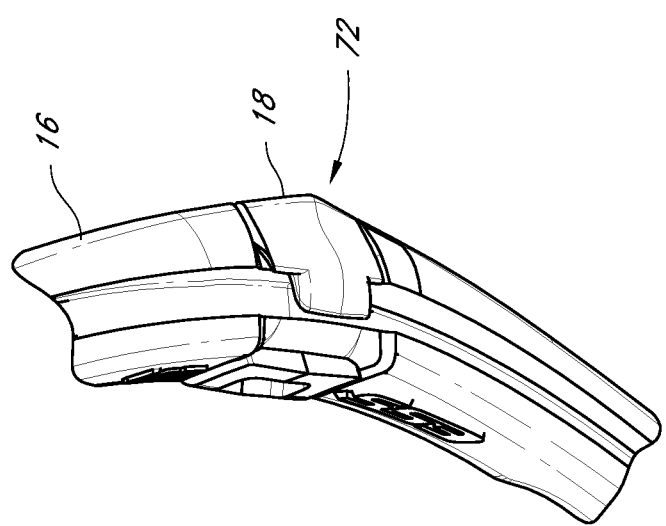
FIG. 8 is a bottom perspective view of the medial portion of the frame, where in the retention component is in an engaged position, according to an embodiment.

As also shown in FIGS. 5-8, in some embodiments, the retention component 18 can be a hingeless clip that defines an outer profile that tapers and blends with the surface of the frame 16. For example, the clip 18 can define a contour or external shape that blends with a contour or external shape of the frame 16. In some embodiments, the contour or external shape can blend in only one of the first or second rotational positions. For example, (as shown in FIGS. 5-6) a mismatch in contour can provide a visible and tactile indication that the clip 18 is in a disengaged position while the clip 18 and frame 16 have a generally or substantially uniform, smooth contour when the clip is in the engaged position (as shown in FIGS. 7-8).

Referring to FIGS. 9-11B, embodiments of the retention component 18 are shown as a rotatable component that is coupled to the frame 16. The body 82 of the retention component 18 can be configured as a generally annular or tubular shape that wraps around at least a portion of the frame 16. For example, the body 82 can be configured as a split ring (as visible in the side views of FIGS. 9-11) that encompasses or surrounds a portion of the frame 16. The retention component 18 can wrap around, for example, at least about 50% and/or less than or equal to about 80% of the perimeter or circumference of a portion of the frame 16, with at least about 20% and/or less than or equal to about 50% of the retention component 18 defining a gap or split 90.

Further, the gap or split 90 can be configured such that at least a portion of the lens can be received therein for securing the lens relative to the frame 16. Thus, when rotated to the disengaged position 70, the gap or split 90 can align with a portion of the frame 16, such as the groove 54. As a result, the retention component 18 can allow passage of at least a portion of the lens 22 into the groove 54 of the frame 16. Furthermore, in the embodiments shown in FIGS. 5-11B, the tab 80 can be disposed at one of the free ends forming the gap or split 90. The retention component 18 can be rotated from the first rotational position or disengaged position to the second rotation position or engaged position in which the tab 80 and gap or split 90 is rotated such that the tab 80 of the retention component 18 engages a portion of the lens. Rotation of the gap or split can enable quick and secure engagement with the lens.

In some embodiments, the retention component 18 can be configured to snap-fit onto the frame 16. In embodiments wherein the retention component is a clip 18, the clip can be urged onto the frame 16 with a portion of the frame 16 passing through the gap or split 90 in the clip. In some embodiments, the clip can be fabricated from a resilient material such that the clip deflects to allow enlargement of the gap or split 90 such that the clip can attach to the frame 16. The clip can therefore be attachable to the frame 16 without requiring pins, latches, or other components. Embodiments disclosed herein can thus allow for superior assembly and maintenance of the eyewear compared to other designs. Further, the design can be durable and sturdy, providing capable and secure retention despite stresses or other forces that may act on the eyewear.

In some embodiments, the retention component 18 can be configured to be mounted to the lens 22 such that the retention component 18 engages a corresponding retention structure in the frame 16 when the lens 22 is mounted onto the frame 16. For example, the retention component 18 can be mounted such that the retention component 18 is movable relative to the lens 22. However, the retention component 18 can be fixed relative to the lens 22. The retention component 18 can be permanently mounted to the lens 22. The retention component 18 can be detachably mounted to the lens 22. Accordingly, in some embodiments, it is not necessary for the clip or retention component 18 to be part of or carried or supported by the frame 16. The various embodiments and features discussed herein with respect to the retention component 18 in embodiments wherein the retention component 18 is carried or supported by the frame 16 can be incorporated into embodiments wherein the retention component 18 is mounted onto the lens 22.

Figure 10:
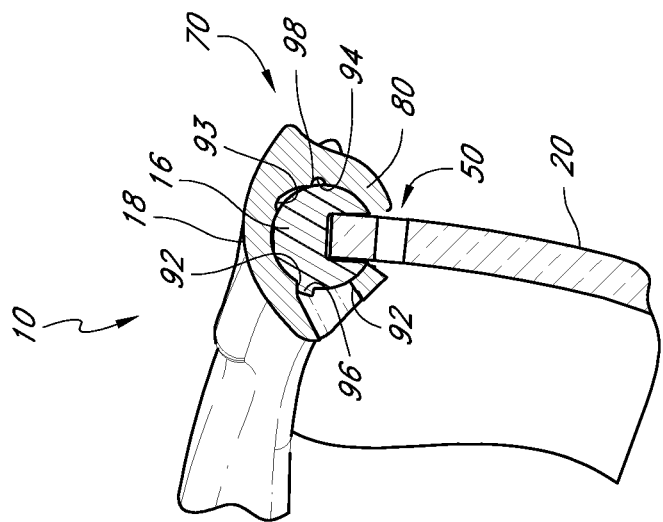
FIG. 10 is a cross-sectional side view of the frame, the retention component, and the lens, wherein the retention component is in the disengaged position and the lens is seated within a groove of the frame, according to an embodiment.

As shown in FIG. 10, the lens 20 can be seated within the groove 54 (FIG. 9) of the frame 16 when the retention component 18 is positioned in the disengaged position 70. Next, when the retention component 18 is rotated to the engaged position 72, as shown in FIG. 11, the tab 80 of the retention component 18 is advanced to a position within the aperture of the engagement portion 50 of the lens 20. As a result, the lens 20 can be generally constrained from movement in all directions at the point of engagement with the frame 16 in the retention component 18.

For example, the eyeglass 10 can tend to provide superior ballistic resistance and lens stability during use. Further, embodiments of the eyewear can be provided in which one or more retention components are utilized to attach the lens to the frame. In such embodiments, the lens can be coupled to the frame in a matter that does not distort the lens or undermine its optical qualities. As a result, embodiments of the eyewear disclosed herein can not only provide superior ballistic resistance and lens stability, but can also provide superior optical quality.

Figure 9:
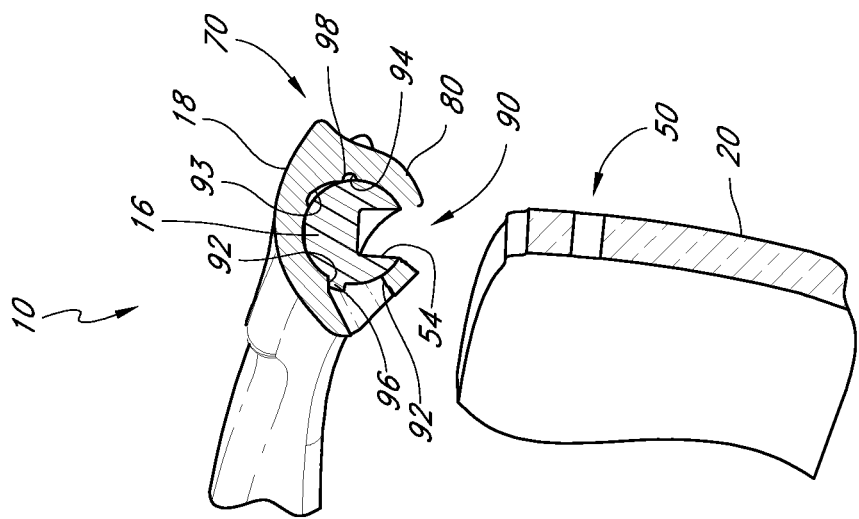
FIG. 9 is a cross-sectional side view of the frame, the retention component, and the lens, wherein the retention component is in the disengaged position and the lens is separated from the frame, according to an embodiment.
Figure 11B:
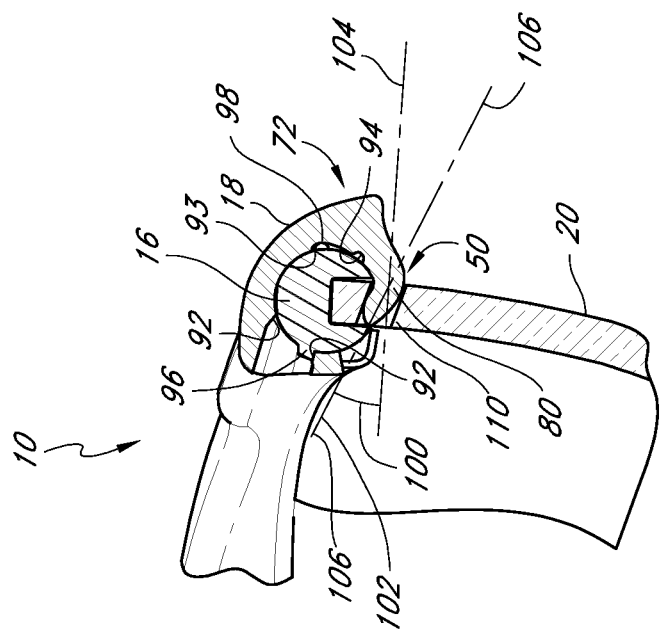
FIG. 11B is a cross-sectional side view of the frame, the retention component, and the lens, wherein the retention component is in the engaged position with the lens being seated within the groove of the frame such that the retention component engages the lens, according to another embodiment.

Additionally, as shown in the embodiments of FIGS. 9-11B, the eyeglass can comprise a motion constrain mechanism. For example, the retention component 18 can comprise one or more stop elements that are configured to interact with one or more stop elements of the frame 16. For example, the retention component 18 can comprise posterior stop elements 92 and upper and lower anterior stop elements 93, 94 that are configured to interact with respective ones of a posterior stop element 96 and an anterior stop element 98 of the frame 16. As illustrated in FIGS. 9-11, the stop elements 92, 93, 94, 96, 98 can restraint rotational movement of the retention component 18 relative to the frame 16. For example, the use of stop elements 92, 93, 94, 96, 98 can facilitate accurate movement from the disengaged position 70 the engaged position 72 and vice versa. Further, in some embodiments, the stop elements 92, 93, 94, 96, 98 can also be used to lock the retention component 18 relative to the frame 16 such that relative rotational movement is resisted and/or prevented. Such a feature can be advantageous once the retention component 18 is moved to the engaged position 72 where it can be snapped into place or otherwise retained to resist and/or prevent inadvertent disengagement.

In the illustrated embodiment, the frame 18 comprises a pair of stop elements 96, 98 formed as protrusions extending from an outer surface of the bridge portion of the frame 16. Although two stop elements 96, 98 are shown, a single stop element can also be used. Further, in embodiments where two stop elements are used, the stop elements can provide different functions for the retention component 18.

For example, the posterior stop element 96 can be relatively larger than the anterior stop element 98 and primarily provide a restraint against rotation in a given direction. The anterior stop element 98 can provide an engagement function that tends to constrain or substantially fix the rotation position of the retention component 18. The posterior stop element 96 can tend to constrain the rotational position of the retention component 18.

In use, with some initial effort to overcome the engagement between the lower, anterior stop element 98 and the lower, anterior stop element 94 of the retention component 18, the retention component 18 can move from the first rotational position or disengaged position 70. The retention component 18 can continue to rotate until being rotationally constrained or stopped by the posterior stop element 96 and the anterior stop element 92. Further, the retention component 18 can be substantially constrained at the second rotational position or engaged position 72 due to engagement between the anterior stop element 98 and the upper, anterior stop element 93. Although the illustrated embodiment shows at least two stop elements of the retention component 18 interacting with at least two stop elements of the frame 16, the motion constraint mechanism can comprise a single stop on the frame and a single stop on the retention component; the stops can interact to provide rotational restraint and substantial fixation of the rotational position.

Therefore, in such embodiments in which the retention component 18 comprises a hingeless clip, the clip can rotate between two or more rotational positions with hardstop features or stop elements 92, 93, 94, 96, 98 of the clip and the frame 16 restraining motion of the clip at one or more of the positions. As shown, the retention component 18 can comprise an interior surface having one or more recesses 92 that engage with one or more protrusions 94 of the frame 16. Further, the retention component 18 can comprise an interior surface having one or more protrusions that engage with one or more recesses of the frame 16. In some embodiments, the hardstop features can be hidden from view when in an assembled state. Further, engagement between the hingeless clip and the frame can also create the desired interaction between the corresponding hardstop features of the clip and the frame.

Although FIGS. 9-11B illustrate embodiments of the retention component 18 as being rotatable relative to the frame 16, the retention component 18 can be configured to pivot or slide relative to the frame 16. In some embodiments, the retention component 18 could be pivotally coupled to a portion of the frame 16. However, in the illustrated embodiment, the retention component 18 is configured to rotate around the frame 16 in order to allow the tab 80 to engage the engagement portion 50 of the lens 20. Further, other slidable and/or rotatable embodiments of a lens retention mechanism and lens structures are disclosed in copending U.S. Patent Application No. 61/373,698, filed on Aug. 13, 2010, the entirety of the disclosure of which is incorporated herein by reference.

Further, the retention component 18 can comprise a resilient material, such as a compressible or flexible material disposed at least along the tab 80 of the retention component 18. As a result, a ballistic event will not tend to result in damage at the interconnection between the retention component 18 and the engagement portion 50. In such embodiments, the tab 80 can be formed from such a resilient or flexible material or comprise a coating, layer, or one or more surface features formed from the resilient or flexible material. The retention component 18, such as the tab 80 and/or the resilient or flexible material, can have a modulus of elasticity that is less than that of the lens. Further, retention component 18, such as the tab 80 and/or the resilient or flexible material, can have a modulus of elasticity that is less than that of the frame. Accordingly, at least a portion of the retention component 18 can dampen or absorb force or vibration from a ballistic event.

Further, the retention component 18 can be configured such that during rotation of the retention component 18 and engagement with the engagement portion 50 of the lens 20, the lens 20 can be brought into the groove 54 to secure the lens 20 within the groove 54. Such a feature can be facilitated using a cam-like motion of the retention component 18 or a cam-like interaction between the tab 80 and the engagement portion 50.

Figure 11A:
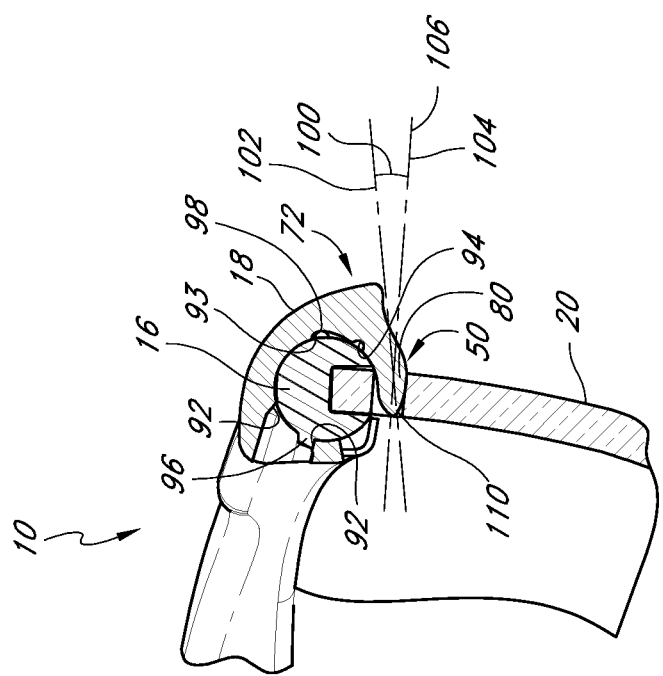
FIG. 11A is a cross-sectional side view of the frame, the retention component, and the lens, wherein the retention component is in the engaged position with the lens being seated within the groove of the frame such that the retention component engages the lens, according to an embodiment.

In some embodiments, the tab 80 of the retention component 18 can engage the engagement portion 50 of the lens 20 in the engaged position (as shown in FIGS. 11A-11B) at a desired engagement angle 100 configured to maximize stability, retention, and resilience of the eyeglass in response to a ballistic event.

The engagement angle 100 can be defined as the angle measured between the tab 80, such as a longitudinal or circumferential centerline or tab axis 102, and a line 104 that is normal to the lens 20. The normal line 104 can be the line that is normal to the lens 20 at approximately the engagement portion 50 of the lens 20.

In some embodiments, the line 104 can be generally parallel or coincident with the axis 106 of the engagement portion 50, as shown in the embodiment of FIG. 11A. Further, in some embodiments, the tab axis 102 can be generally parallel or coincident with a longitudinal centerline or axis 106 of the engagement portion 50 of the lens 20. For example, as shown in the embodiment of FIG. 11B, the tab axis 102 can be generally parallel or coincident with the axis 106 of the engagement portion 50 and oriented transversely or obliquely relative to the normal line 104 of the lens 20.

The engagement angle 100 can be oriented to ensure optimal retention of the lens 20 relative to the frame 16. For example, in either of the embodiments shown in FIGS. 11A-11B and other embodiments, the engagement angle 100 can be at least about 5 degrees and/or less than or equal to about 40 degrees relative to a horizontal plane. Further, in some embodiments, the tab 80 can engage the engagement portion of the lens at an engagement angle 100 of at least about 10 degrees and/or less than or equal to about 30 degrees relative to a horizontal plane. In some embodiments, the engagement angle 100 can be approximately 12 degrees. In other embodiments, such as the embodiment of FIG. 11B, the engagement angle 100 of approximately 19.2 degrees has been found to provide excellent results in ballistic testing.

Furthermore, the rotational range of the retention component 18 between the engaged and disengaged positions can be at least about 10 degrees and/or less than or equal to about 180 degrees. For example, as shown in FIGS. 10-11B, the retention component 18 can rotate about 45 degrees from the engaged position to the disengaged position.

In some embodiments, the tab 80 retention component 18 can engage the engagement portion 50 of the lens 20 with a leading end 110 of the tab 80 extending through the engagement portion 50. For example, FIGS. 11A-B illustrates that the leading end 110 extends to the other face or through the width of the lens 20. However, the leading end 110 can extend only partially into the engagement portion 50 or beyond the engagement portion 50. For example, the leading end 110 can extend through the engagement portion 50 at least about 5 degrees and/or less than or equal to about 90 degrees. Thus, the leading end 110 can be rotated down from the frame 16, through the lens 20, and back toward the frame 16. In some embodiments, the leading end 110 can snap fit or engage the frame 16 to reach a locked fit in the engaged position.

Figure 12:
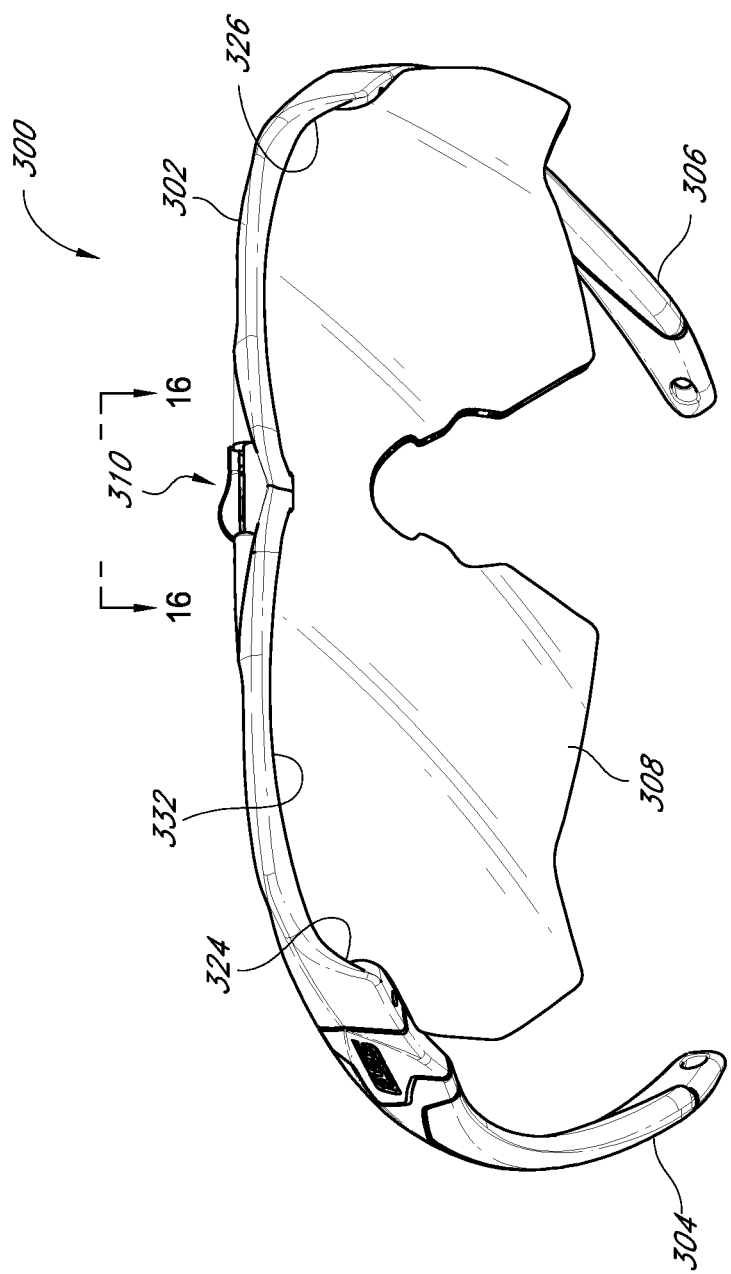
FIG. 12 is a perspective view of an eyeglass comprising a retention component for securing a lens to a frame of the eyeglass, in accordance with another embodiment.

Referring now to FIGS. 12-19, another embodiment of an eyeglass having a retention mechanism is shown. FIG. 12 is a perspective view of an eyeglass 300 that comprises a frame 302, a pair of ear stems 304, 306 extending rearwardly from the frame 302, a lens 308, and a retention mechanism 310. In this embodiment, the retention mechanism 310 can be concealed within the frame 302 such that the eyeglass 300 maintains the appearance of a conventional eyeglass while exhibiting excellent ballistic properties.

Figure 13:
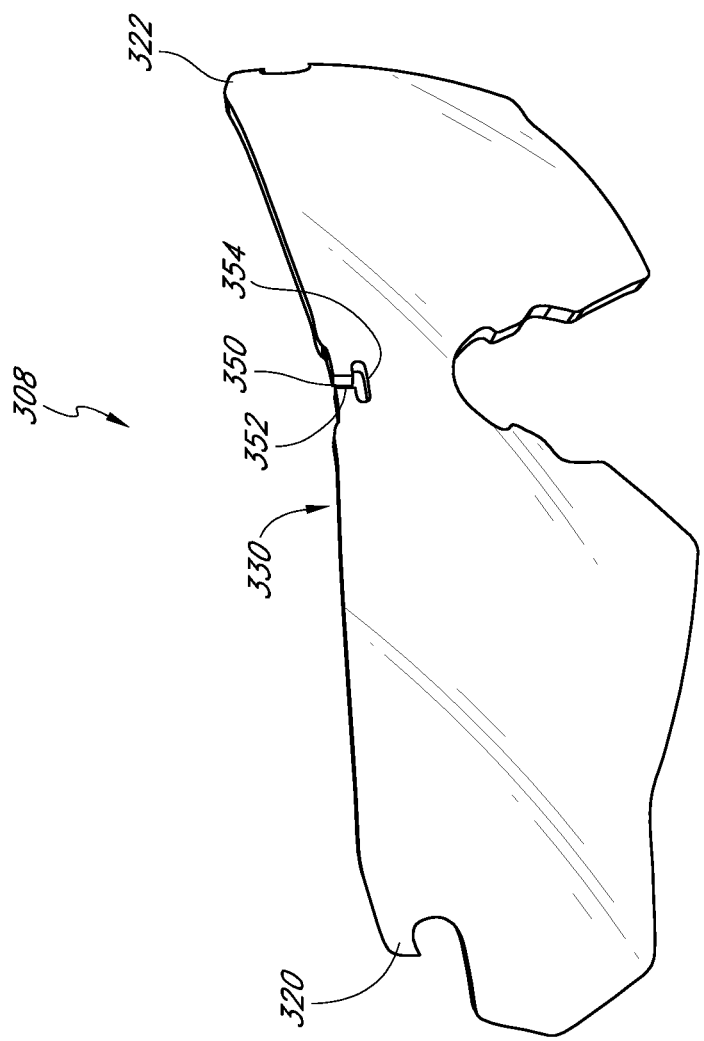
FIG. 13 is a perspective view of a lens comprising a slot that can be engaged and/or supported by the retention component of the eyeglass shown in FIG. 12, according to an embodiment.

FIG. 13 illustrates an embodiment of a lens 308 for use with an eyeglass. The lens 308 can be configured to be supported by the frame 302. For example, the lens 308 can comprise one or more engagement portions that can be engaged with one or more retention components of the eyeglass for supporting the lens. Further, other structures can be used to support the lens. For example, the frame can comprise one or more opposing terminals and the lens can comprise one or more projections that can be fitted into the terminal(s) of the frame. However, the use of structures such as projections and terminals is optional and can be omitted in some embodiments. For example, structures in addition to the retention component(s) and engagement portion(s) may be unnecessary where two or more retention components and engagement portions are spaced apart along the edge of the lens.

In some embodiments, the lens 308 can comprise a pair of projections 320, 322 that can be seated in corresponding terminal recesses 324, 326 of the frame 302. Further, the lens 308 can comprise an upper edge or boundary 330. In use, when the projections 320, 322 are fitted into the recesses 324, 326 of the frame 302, the upper edge or boundary 330 of the lens 308 can be generally snap-fitted into and retained within a lens groove 332 of the frame 302. Thus, in some embodiments, such an arrangement can provide a further degree of lens retention and stabilization in addition to that provided by the retention component.

In accordance with the embodiment shown in FIGS. 12-19, the lens 308 can also comprise an engagement portion 350. The engagement portion 350 can comprise at least one portion of the lens 308 can be one of a recess, surface contour, cut-out, projection, slot, aperture, and other such surface structures and be formed in a variety of shapes and/or sizes. For example, in the illustrated embodiment, the engagement portion 350 is shown as a cut-out that extends through the thickness of the lens 308. Further, the engagement portion 350 is shown as a single cut-out, but can be formed as a plurality of cut-outs. Additionally, the engagement portion 350 can be formed to comprise a narrowed section 352 and a wide section 354.

Figure 15:
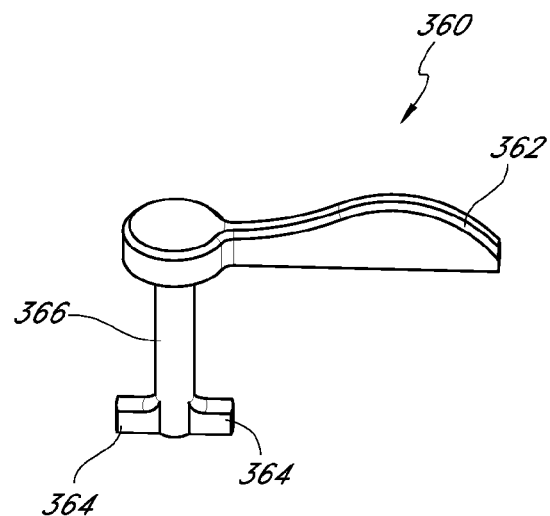
FIG. 15 is a perspective view of the retention component of the eyeglass of FIG. 12, according to an embodiment.

Referring now to FIG. 15, an embodiment of a retention component 360 is shown. The retention component 360 can be configured to engage and secure the lens 308 relative to the frame 302. For example, the retention component 360 can be positioned in one of an engaged position and a disengaged position. In the engaged position, the retention component 360 can interlock, engage, and/or otherwise secure at least a portion of the lens 308 relative to the frame 302. In the disengaged position, the retention component 360 can allow the lens 308 to move freely relative to the frame 302. Further, the retention component 360 can be manually actuated by the wearer in order to allow the wearer to interchange lenses.

In the illustrated embodiment, the retention component 360 can comprise a switch or handle 362 and at least one tab 364. The retention component 360 can be configured to rotate about a generally vertical axis relative to the eyeglass 300. The handle 362 can be actuated by the wearer. In some embodiments, the retention component 360 can comprise an elongate shaft 366 extending between the handle 362 and the tab 364. Further, some embodiments can be configured such that the retention component 360 comprises a pair of tabs 364. As shown, the tab(s) 364 can extend in generally opposite horizontal directions and be attached to a lower or bottom end of the retention component 360.

Figure 17:
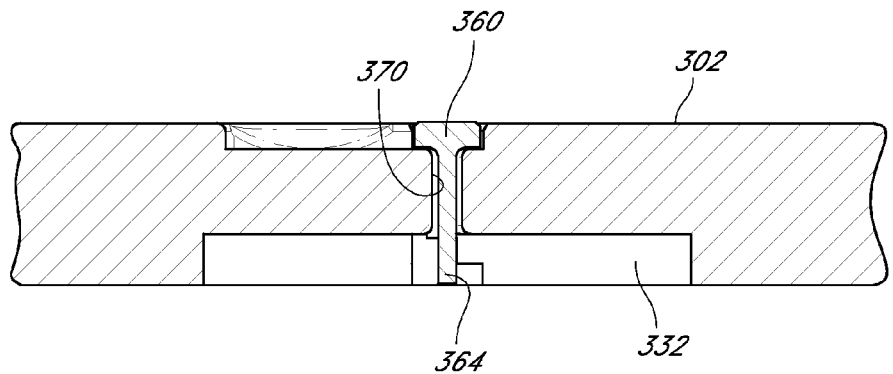
FIG. 17 is a cross-sectional front view of the frame and retention component of the eyeglass of FIG. 12, wherein the retention component is in a disengaged position, according to an embodiment.
Figure 18:
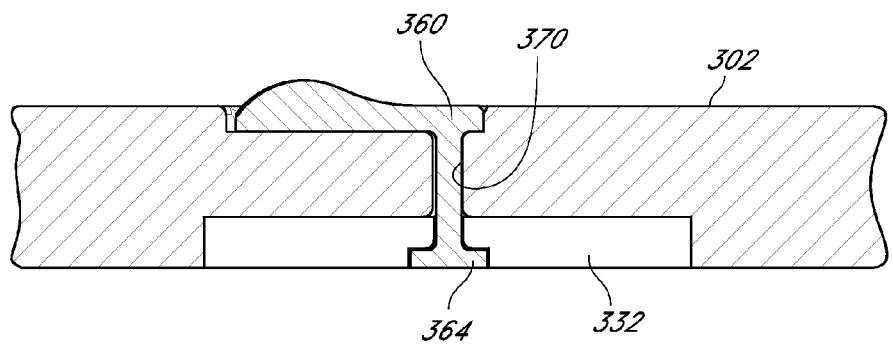
FIG. 18 is a cross-sectional front view of the frame and retention component of the eyeglass of FIG. 12, wherein the retention component is in an engaged position, according to an embodiment.
Figure 19:
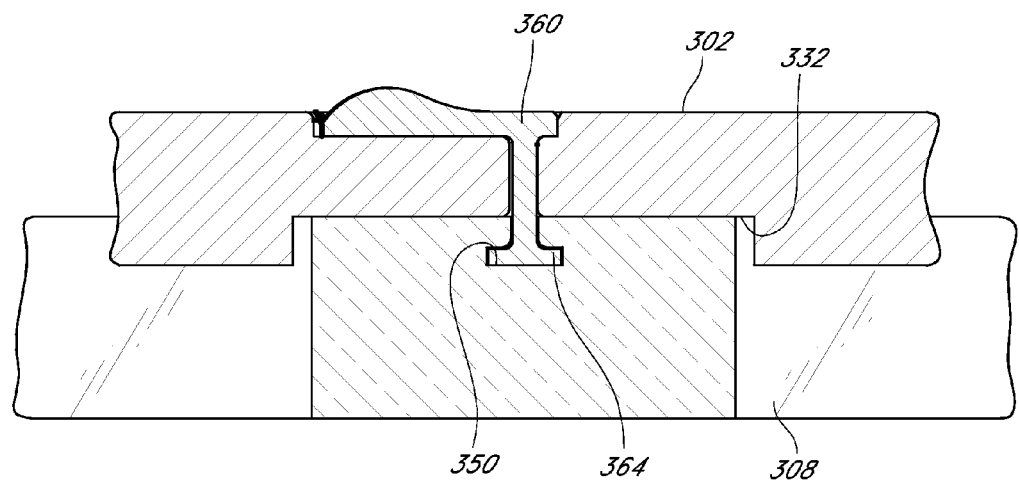
FIG. 19 is a cross-sectional front view of the frame and retention component of the eyeglass of FIG. 12, wherein the retention component is in the engaged position and engaging the lens, according to an embodiment.
Figure 20:
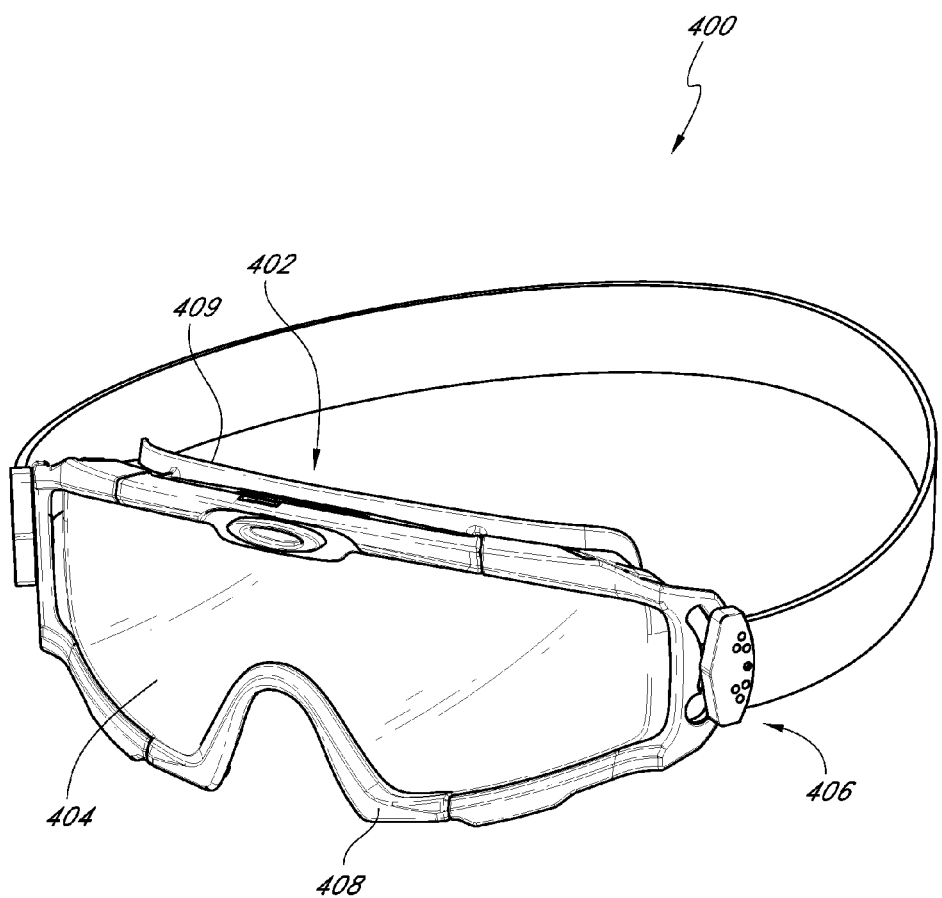
FIG. 20 is a perspective view of a goggle comprising a retention system for securing a lens to a frame of the eyeglass and a centroidal vectoring strap system, in accordance with another embodiment.

The tab 364 can be disposed adjacent to the lens 308 for engaging the lens 308 such that the tab 364 can be positioned in an engaged position or a disengaged position relative to the lens 308 for engaging lens 308. The engaged and disengaged positions of the retention component 360 relative to the frame 302 are shown in FIGS. 17 and 18. Further, FIG. 19 illustrates the retention component 360 engaging the lens 308 in the engaged position.

Figure 14:
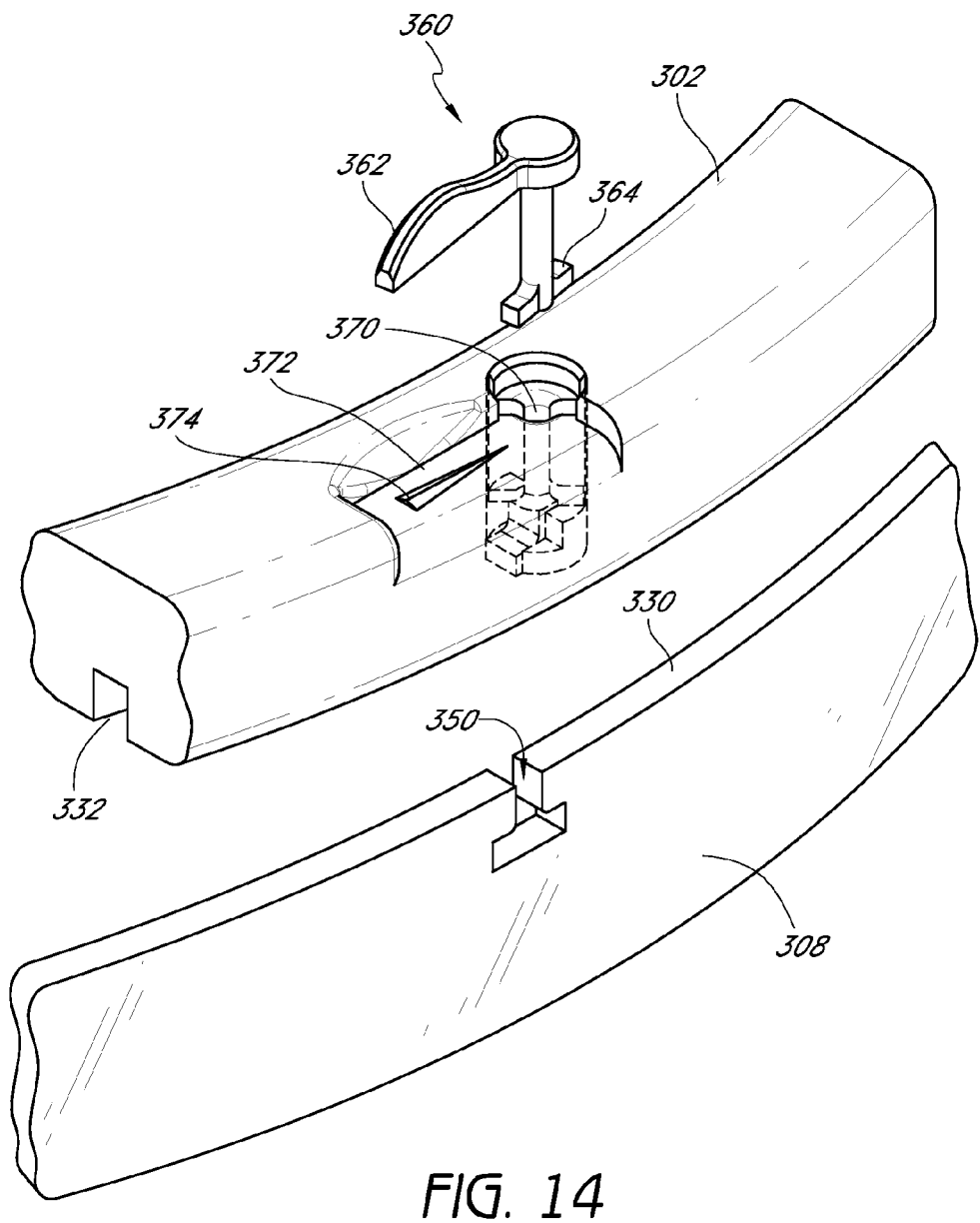
FIG. 14 is a perspective view of another eyeglass, frame, and retention component according to another embodiment.
Figure 16:
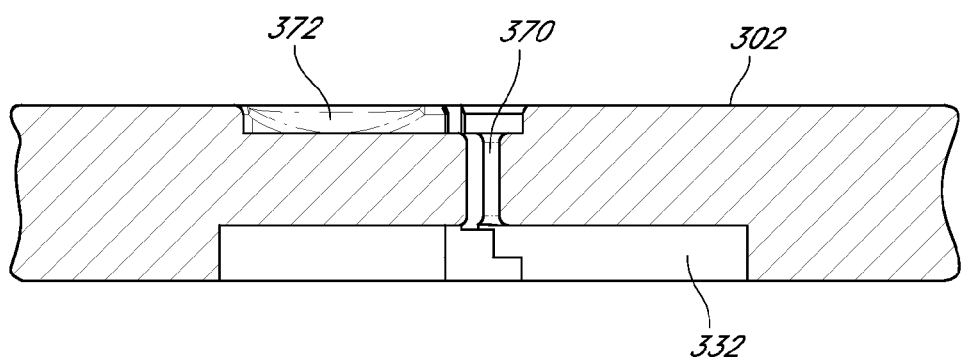
FIG. 16 is a cross-sectional front view of the frame of the eyeglass of FIG. 12, illustrating a recess configured to support the retention component shown in FIG. 15, according to an embodiment.

FIG. 14 is an enlarged perspective view of the eyeglass 300 and the retention mechanism 310. FIG. 16 is a cross-sectional front view of the frame 302 of the eyeglass 300 taken along lines of FIG. 12. As illustrated, the frame 302 can comprise a recess 370 configured to support the retention component 360 shown in FIG. 15, according to an embodiment. FIG. 16 also illustrates the lens groove 332 extending along the frame 302. The recess 370 can be configured to allow the tab 364 of the retention component 360 to be passed downwardly toward the lens groove 332. Further, the recess 370 can comprise a handle-receiving section 372 at an upper end thereof for accommodating at least a portion of the handle 362 of the retention component 360. As shown in FIG. 14, the recess 370 can comprise a rotational step-wise distribution of gaps. The gaps can be configured to allow the tab(s) 364 of the retention component 360 to be rotated as it is advanced into the recess 370, which rotation can limit axial or vertical movement of the retention component 360 (and unintentional removal of the retention component 360 from the recess 370). In this manner, the retention component 360 can be securely seated into and retained by the recess 370. In use, the recess 370 can allow the retention component 360 to rotate therein with the handle 362 being pivotable within the section 372 of the recess 370. Further, the frame 302 can comprise a bump 374 that provides interference and/or frictional resistance to movement of the handle 362 thereover. Thus, unintentional rotation and disengagement of the retention component 360 can be generally resisted and/or prevented.

Additionally, as shown in FIGS. 17 and 18, when the retention component 360 is disposed in the recess 370, the tab 364 can be positioned within or extend within the lens groove 332. Accordingly, the tab 364 can be rotated such that the retention component 360 is in the disengaged position, as shown in FIG. 17. When the retention component 360 is in the disengaged position, the lens 308 can be positioned within the lens groove 332 with the tab 364 fitting into the narrowed section 352 of the engagement portion 350 of the lens 308. Further, as shown in FIG. 19, the retention component 360 can be rotated to the engaged position such that the at least one tab 364 rotates to fit within the widened section 354 of the engagement portion 350 of the lens 308. The retention component 360 can thus be rotated in a plane that is generally coplanar with the engagement portion 350 of the lens. Thus, the retention component 360 can rotate within the engagement portion 350 of the lens 308 in order to selectively engage or disengage with the lens.

The embodiment shown in FIGS. 12-19 enables the retention component 360 to interlock or couple the lens 308 relative to the frame 302. Notably, with the upper edge or boundary 330 of the lens 308 being fitted into the lens groove 332 and with the tab 364 engaging the engagement portion 350 of the lens 308, the lens 308 can be generally constrained against sliding and rotational movement with respect to the frame 302. The ballistic strength of the eyeglass can be substantially increased with such a design.

In accordance with another embodiment, FIGS. 20-46 illustrate a goggle 400 having a lens retention assembly 402, a removable lens 404, a centroidal vectoring strap system 406, and a frame 408. Similar to the eyeglass embodiments noted above, the goggle 400 can be configured to provide superior ballistic lens retention. For example, the goggle 400 improves ballistic impact performance by placing robust retention features perpendicular to the direction of lens dislodgment. Additionally, the goggle 400 ensures easy and practical lens removal and installation.

The lens retention assembly 402 can be incorporated into eyewear, such as an eyeglass or goggle embodiment, using a unitary or dual lenses. Furthermore, some embodiments can be provided in which the retention components 18, 360 of the eyeglass embodiments noted above are integrated into and/or replace the lens retention assembly 402 of the goggle 400 and vice-versa. Moreover, various modifications can be made to the goggle or eyeglass embodiments to incorporate or exchange one or more features of the embodiments discussed herein or as known in the art.

In addition, the goggle 400 can comprise a suspension assembly 409 that is positioned posteriorly relative to the frame 408. The suspension assembly 409 can comprise a variety of structures and materials known in the art. However, the suspension assembly 409 can also incorporate embodiments of suspension assemblies disclosed in the copending U.S. Patent Application No. 61/315,752, filed on Mar. 19, 2010, titled Goggle, and U.S. Patent Application No. 61/426,222, filed on Dec. 22, 2010, titled Eyewear, the entireties of each of which are incorporated herein by reference.

Figure 21:
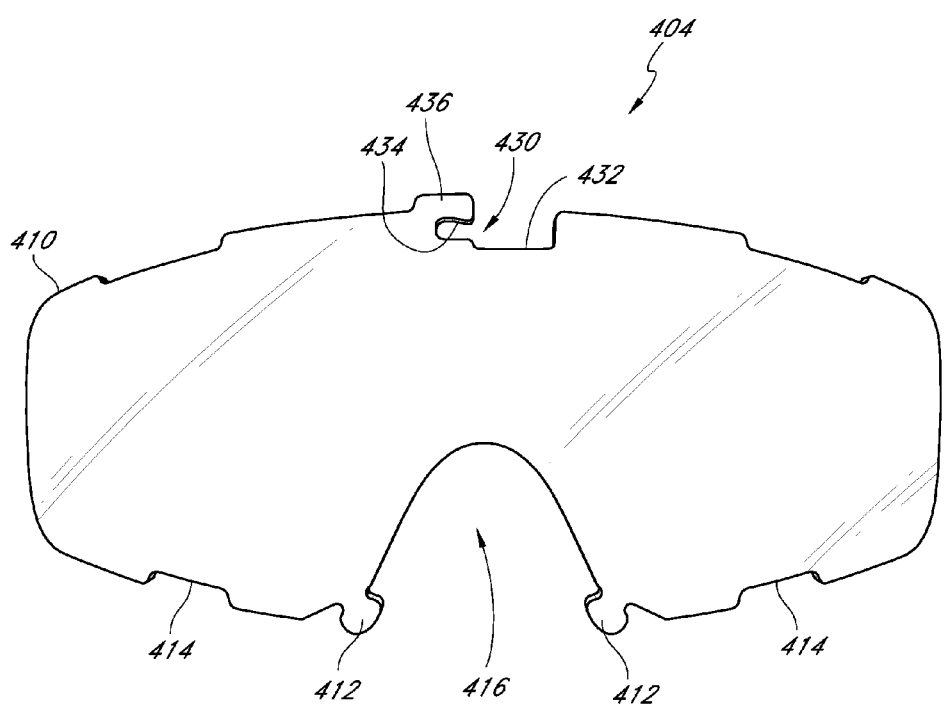
FIG. 21 is a front view of a lens according to an embodiment.

FIGS. 20-32B illustrate specific features related to the lens retention assembly 402. FIG. 21 illustrates a front view of the lens 404. The lens 404 can be configured as a unitary lens, but can also comprise dual lenses in some embodiments. The lens 404 can comprise a lens periphery 410 that defines one or more unique shapes, features, recesses, apertures, sections of reduced lens thickness, cut-outs or other structures that can interact with the frame 408 or other components attached thereto in order to secure the lens 404 relative to the frame 408. One or more such shapes, features, recesses, apertures, sections of reduced lens thickness, cut-outs or other structures can be disposed at any location along the periphery 410 of the lens 404. In some embodiments, one or more such shapes, features, recesses, apertures, sections of reduced lens thickness, cut-outs or other structures can be disposed at a centralized location of a lens, at opposing sides of a lens, or distributed at multiple locations on a lens, whether the lens is part of a unitary lens or dual lens design.

For example, the lens periphery 410 can define one or more passive retention structures and/or one or more active retention structures. A passive retention structure can be defined as a structure that is placed against, into, or through a portion of the frame 408 or other component attached thereto, which is operative to at least partially secure the lens 404 relative to the frame 408 after such placement. An active retention structure can be defined as a structure that is not only placed against, into, or through a portion of the frame 408 or other component attached thereto, but that is also engageable with the frame 408 or other component attached thereto due to movement of a portion of the frame 408 itself or another component. The active retention structure can be operative to at least partially secure the lens 404 relative to the frame 408 after movement of the other component or portion of the frame 408.

The passive retention structure of the lens 404 can comprise a shape, feature, recess, cut-out, protrusion, aperture, indentation in the lens periphery, section of reduced lens thickness, and/or other such structures. In the embodiment shown in FIG. 21, the lens 404 can comprise a pair of protrusions 412 and a pair of recesses 414 disposed along the lens periphery 410 that can serve as passive retention structures. The protrusions and/or recesses can be positioned in a variety of locations about the lens periphery 410. In some embodiments, protrusions and/or recesses can be positioned opposite an active retention structure, spaced apart from each other, and/or positioned on opposing sides of a nosepiece opening 416 of the lens 404. In the illustrated embodiment, the protrusions 412 and recesses 414 are disposed along a lower edge of the lens periphery 410 on opposing sides of the nosepiece opening 416 of the lens 404. As such, the lens 404 can be easily aligned and placed into engagement with the frame 408.

Figure 22:
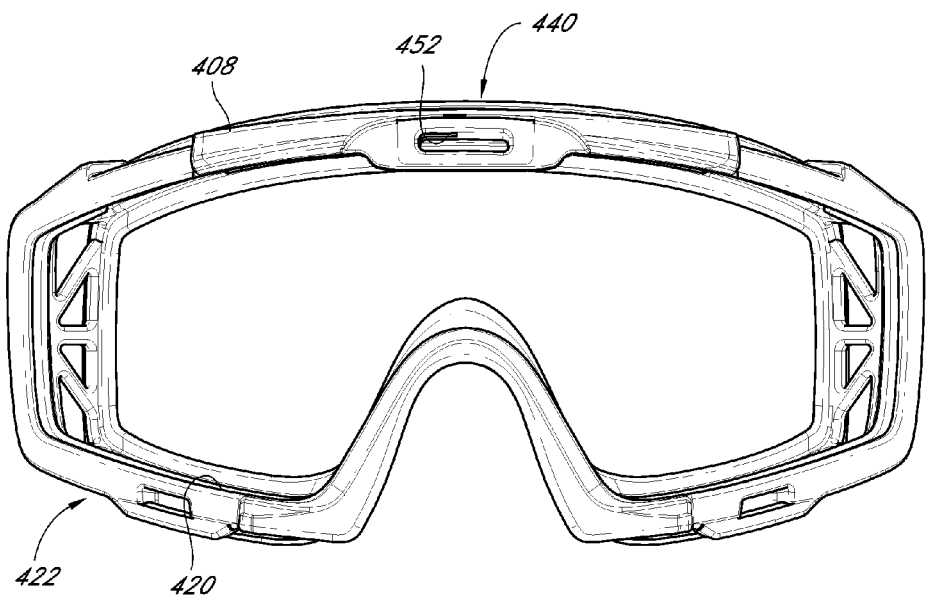
FIG. 22 is a front view of a frame of the goggle of FIG. 20.
Figure 23:
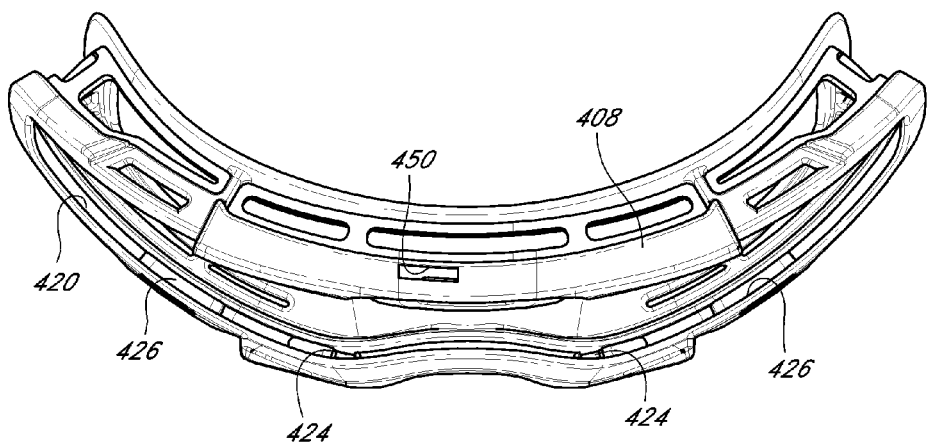
FIG. 23 is a top view of the frame of FIG. 22.

The frame 408 can also comprise one or more retention structures, including a passive retention structure and/or an active retention structure. A passive retention structure can comprise a shape, feature, recess, protrusion, aperture, indentation, and/or other such structure that interacts with a passive retention structure of the lens 404 to at least partially secure the lens 404 relative to the frame 408. For example, engagement between passive retention structures of the frame 408 and the lens 404 can restrict one or more degrees of movement of the lens 404 relative to the frame 408. Referring to FIGS. 22-23, the frame 408 can comprise a lens groove 420 that extends at least partially around a periphery 422 of the frame 408. The lens groove 420 is an example of a passive retention structure. Further, the frame 408 can also comprise one or more other passive retention structures, such as one or more recesses, protrusions, or apertures formed in the lens groove 420 that can be engaged by one or more passive retention structures of the lens 404.

For example, the frame 408 can comprise a pair of recesses 424 that are configured to be engaged with the protrusions 412 of the lens 404 and a pair of protrusions 426 that are configured to be engaged with the recesses 414 of the lens 404. Accordingly, the lens 404 can be inserted downwardly and to the frame 408 such that the protrusions 412 fit into the recesses 424 and such that the recesses 414 receive the protrusions 426. The passive retention structures can enable the lens 404 to be properly seated within the lens groove 420 and can also at least partially secure the lens 404 relative to the frame 408 by restricting one or more degrees of movement of the lens 404 relative to the frame 408.

Additionally, as noted above, the lens 404 can also comprise one or more active retention structures. Similar to the passive retention structure, the active retention structure can comprise a protrusion, an aperture, an indentation in the lens periphery, a section of reduced lens thickness, and/or other such structures. However, the active retention structure of the lens 404 can be configured to be engaged by one or more active retention structures, such as movable components or portions of the frame 408 or other components attached thereto, in order to secure the lens 404 relative to the frame 408. In some embodiments, engagement between the active retention structures of the lens 404 and the frame 408 can restrict one or more of any remaining degrees of movement of the lens 404 relative to the frame 408.

In the illustrated embodiment of FIGS. 21-23, the lens 404 can comprise a slot 430 disposed along the lens periphery 410. The slot 430 can be an active retention structure of the lens 404. The slot 430, used with a lens engagement mechanism or member and an aperture or groove of the frame, can be used to secure the lens to restrict all degrees of motion of the lens in order to prevent lens dislodgment. During a ballistic event, a typical goggle lens may be dislodged in any direction, which direction can have an anterior, posterior, lateral, or vertical component. However, the lens retention assembly 402, which can comprise the slot 430, can aid in reducing and/or preventing dislodgment. Thus, the lens 404 will tend not to be dislodged in response to a high-energy ballistic event.

The slot 430 can provide other functional and structural benefits. For example, slot 430 can comprise a lower section 432 adjacent to an open end thereof and one or more edges 434 by which the slot 430 defines a variable width. The slot 430 can also comprise a closed end 438. Additionally, the lens 404 can include a hook portion 436 that extends at least partially from the lens periphery 410 and defines a boundary to the closed end 438 of the slot 430. In the illustrated embodiment, the edge 434 can form a downwardly projecting tab at a distal end of the hook portion 436. In some embodiments, the downwardly projecting tab 434 can act as a a retention device for a clip or lens engagement mechanism. The hook portion 436 can be configured as a flexible or resilient structure. The hook portion 436 can be formed monolithically or separately from the lens 404. Further, the hook portion 436 can comprise at least one bump, protrusion, detent, recess, or other structure, such as the tab 434 that enables the hook portion 436 to be engaged and secured relative to the frame 408.

Referring to FIGS. 22-23, the frame 408 can comprise an active engagement portion 440 that forms part of the lens retention assembly 402. The active engagement portion 440 can comprise a portion of the frame that is configured to receive or fit against the active retention structure of the lens 404 in order to at least partially secure the lens 404 relative to the frame 408. In some embodiments, the active engagement portion 440 can comprise an aperture, recess, cavity, or indentation in the frame 408. Further, the active engagement portion 440 can comprise one or more other components that facilitate interconnection and engagement with the lens 404.

For example, FIG. 22 illustrates an embodiment of the frame 408 in which the active engagement portion 440 comprises a generally vertical aperture 450 that extends upwardly through a central portion of the upper wall or rim of the frame 408. The aperture 450 is configured to receive the hook portion 436 of the lens 404 when the lens 404 is positioned within the lens groove 420 of the frame 408. Additionally, at least a portion of the lens 404 can align with the active engagement portion 440 securing the lens 404 relative to the frame 408. For example, the active engagement portion 440 can comprise a generally horizontally extending aperture 452 that can be aligned with at least a portion of the slot 430 of the lens 404 when the lens 404 is positioned within the lens groove 420 of the frame 408.

Figure 24:
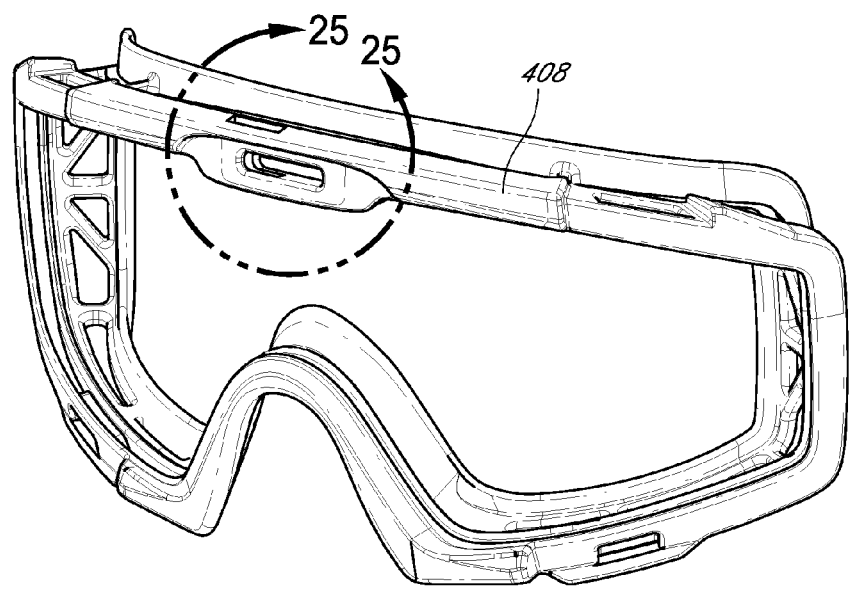
FIG. 24 is a perspective view of the frame of FIG. 22.
Figure 25:
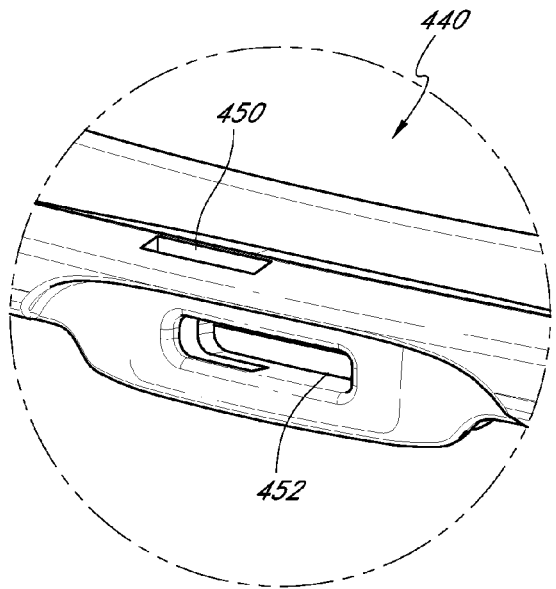
FIG. 25 is a detailed perspective view of a retention aperture of the frame of FIG. 24.

The frame 408 can comprise one or more surfaces that support a slidable lens engagement mechanism. For example, FIGS. 24-25 illustrate a perspective view and a detailed view of the apertures 450, 452 of the active engagement portion 440. The aperture 452 can be configured to receive and support a slidable lens engagement mechanism. Thus, in some embodiments, the hook portion 436 of the lens 404 can be inserted upwardly through the aperture 450 such that the open end of the slot 430 receives at least a portion of a slidable lens engagement mechanism. Subsequently, the slidable lens engagement mechanism can be moved from a disengaged position to an engaged position in order to secure the hook portion 436 relative to the frame 408. The interaction between the slidable lens engagement mechanism can therefore resist and/or prevent the hook portion 436 from exiting the aperture 450.

The slidable engagement mechanism can be configured to include a generally elongate portion that can extend through the aperture 452 of the frame 408. The slidable engagement mechanism can also comprise one or more lens retention components. The slidable engagement mechanism can be formed integrally or of separate components. The active engagement portion 440 of the frame 408 can comprise at least one surface configured to support at least a portion of the slidable engagement mechanism. Further, the slidable engagement mechanism can be actuatable through sliding, translation, or rotation, in either a vertical or horizontal direction. The engagement mechanism can also be biased using a biasing mechanism, such as a spring, deflectable portion, or other such structures.

Additionally, the engagement mechanism can also comprise a locking structure that secures the engagement mechanism in a disengaged and/or engaged position relative to the frame 408. The engagement mechanism can be user-actuated to allow for quick and reliable engagement or disengagement with the lens 404. The locking structure of the engagement mechanism can interact with the frame 408 itself or with the lens 404 when fitted into the frame 408.

FIGS. 26A-D illustrates an embodiment of a slidable lens engagement mechanism or member 470. The engagement member 470 can comprise an actuating portion 472, an elongate central body 474, and a retention tab 476. The actuating portion 472 can be configured to allow easy user manipulation of the engagement member 470 such that a user's fingers can grasp the actuating portion 472 to enable the user to move the engagement member 470 between engaged and disengaged positions.

In some embodiments, the retention tab 476 can be configured as an enlarged portion of the body 474 disposed at a distal end thereof. Furthermore, the retention tab 476 can be fabricated from a compressible or deflectable material or comprise a compressible or deflectable structure. Additionally, the actuating portion 472 and the retention tab 476 can both define a passing profile that is greater than the cross-sectional profile or internal profile of the aperture 452.

The engagement member 470 can be coupled to the frame 408 in a manner that resists and/or prevents separation of the engagement member 470 from the frame 408 absent undue force. An undue force can be a force that exceeds a typical sliding force that is necessary to move the engagement member 470 between engaged and disengaged positions.

In some embodiments, the coupling between the engagement member 470 and the frame 408 can be provided by the retention tab 476 and/or the actuating portion 472. For example, the retention tab 476, along with the actuating portion 472, can function to maintain engagement between the engagement member 470 and the aperture 452 of the active engagement portion 440. During assembly, the retention tab 476 can be urged into an anterior end of the aperture 452 of the active engagement portion 440 and thereby compressed or deflected until exiting a posterior end of the aperture 452. Once the retention tab 476 exits the posterior end of the aperture 452, the retention tab 476 can rebound to its original configuration such that the retention tab 476 and the actuating portion 472 resist and/or prevent the body 474 of the engagement member 470 from exiting the aperture 452. Further, the aperture 452 may be deflected during insertion, allowing the retention tab 576 to be received into the aperture 452. Thus, with reference to the side view of the engagement member 470 shown in FIG. 26C, the frame 408 can be captured between an interior face of the actuating portion 472 and an interior face of the retention tab 476.

Figure 26A:
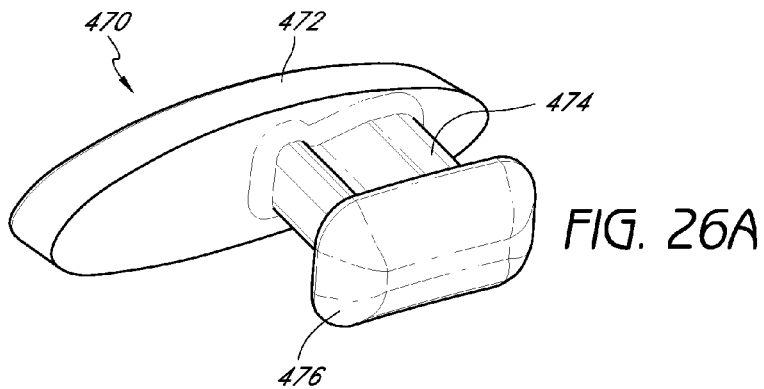
FIG. 26A is a perspective view of a retention component of the retention system of the goggle of FIG. 20.
Figure 26B:
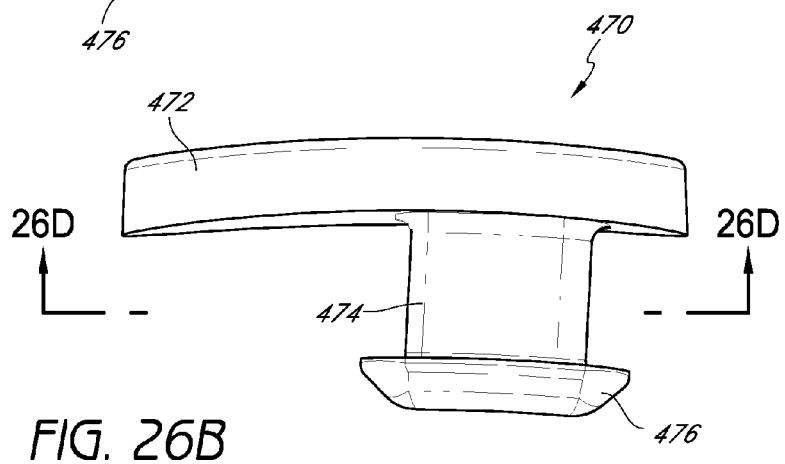
FIG. 26B is a top view of the retention component of FIG. 26.
Figure 26C:
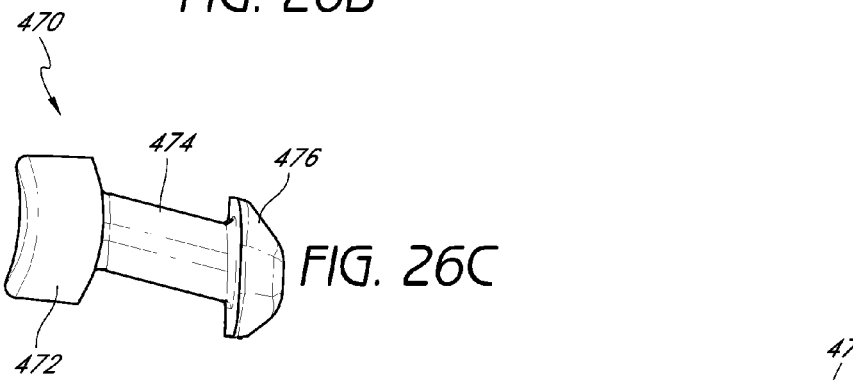
FIG. 26C is a side view of the retention component of FIG. 26.
Figure 26D:
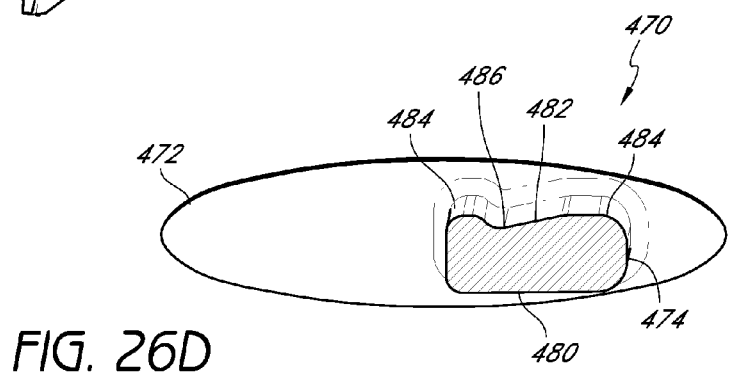
FIG. 26D is a rear cross-sectional view of the retention component of FIG. 26.

FIG. 26D is a cross-sectional end view of the body 474 of the engagement member 470. As shown, the body 474 comprises a variable geometry that provides exceptional benefits. For example, a lower surface 480 of the body 474 can stably support the engagement member 470 during movement within the aperture 452. The body 474 can also comprise an upper surface 482 having one or more ridges 484 and/or one or more recesses or indentations 486. The ridge 484 and/or indentation 486 of the upper surface 482 can enable the engagement member 470 to engage with the lens of 404 and/or the frame 408 in the engaged and/or disengaged positions.

In some embodiments, the ridge 484 and/or indentation 486 can engage with a corresponding recess or protrusion of the lens 404 or frame 408. For example, in the embodiments shown in FIGS. 21 and 26D, the edge or downwardly projecting tab 434 of the hook portion 436 of the lens 404 can be received within the indentation 486 of the body 474 of the engagement member 470. This interaction will be described further below reference to FIGS. 32A-B.

FIGS. 27-32B illustrate the goggle 400 assembled such that the lens 404 has been fitted into the lens groove 420 of the frame 408 with the passive retention structures (the protrusions and recesses) of the lens 404 being received by corresponding passive retention structures (recesses and protrusions) of the frame 408. FIG. 27 is a front view of the goggle 400 wherein the lens 404 is received within the lens groove 420 of the frame 408 and initially secured using passive retention structures. However, an active retention structure of the frame 408, the engagement member 470, is positioned in a disengaged position 490. As such, the lens 404 may be removed or dislodged from the lens groove 420 of the frame 408.

As illustrated in FIGS. 28-29B, when the engagement member 470 is in the disengaged position 490, the engagement member 470 is positioned within the open end of the slot 430 of the lens 404. Thus, the lens 404 can be moved toward or away from the engagement member 470 with ease to replace the lens 404 or if the lens 404 is somehow dislodged by another force.

In some embodiments, as shown in the cross-sectional view of FIG. 29B, the lower section 432 of the slot 404 can be configured such that the body 474 of the engagement member 470 can pass thereinto. For example, in use, the lens 404 can be inserted into the groove 420 of the frame 408 by first, inserting an upper edge of the lens periphery 410 into the lens groove 420 of the frame 408 and thereafter inserting the lower edge of the lens periphery 410 into the lens groove 420. The recess or indentation of the lower section 432 of the slot 430 can be configured such that the body 474 of the engagement member 470 can be positioned therein while the lens 404 is fitted into the lens groove 420 of the frame 408. In some embodiments, this feature provides a degree of play or movement when inserting the upper edge of the lens 404 into the groove 420 of the frame 408 so that the lower edge of the lens 404 can be inserted into the groove 420.

Further, in some embodiments, the initial play or superfluous movement of the lens 404 within the groove 420 can be reduced and/or eliminated by virtue of the interaction between the engagement member 470 and the slot 430 of the lens 404. For example, the slot 430 can be positioned within the lens perimeter such that when the slot 430 is engaged by the engagement member 470, the lens 404 is urged into engagement with a lower portion of the lens groove 420 of the frame 408. Further, the engagement member 470 can restrict and/or fix the relative positioning of the lens 404 relative to the engagement member 470 and the frame 408.

In some embodiments, the lens 404 can be configured such that the spacing between the lower edge of the lens 404 and the closed end 438 of the slot 430 of the lens 404 allows the lens to be urged downwardly into the lens groove 420 of the frame 408 when the engagement member 470 is positioned within the closed end 438 of the slot 430. For example, the spacing between the lower edge of the lens 404 and the closed end 438 can be approximately equal to a spacing between a lower edge of the lens groove 420 of the frame 408 and the aperture 452 of the active engagement portion 440. In some embodiments, the spacing can be configured such that the lens is secured within the lens groove 420 in a manner that substantially restricts and/or eliminates play or movement of the lens within the groove 420 without creating compressive or bending stresses in the lens.

Referring now to FIGS. 30-32B, an active retention structure (the slot 430) of the lens 404 can be positioned within the aperture 452 of active engagement portion 440 of the frame 408. While the passive retention structures of the lens 404 and the frame 408 provide an initial degree of engagement between the lens 404 and the frame 408, the active retention structures can provide further stability and engagement. For example, the interaction between the engagement member 470 of the lens retention assembly 402 and the lens 404 provides a final degree of engagement between the frame 408 and the lens 404. In some embodiments, engagement between the active retention structures of the lens 404 and the frame 408 can restrict one or more of any remaining degrees of movement of the lens 404 relative to the frame 408.

Figure 30:
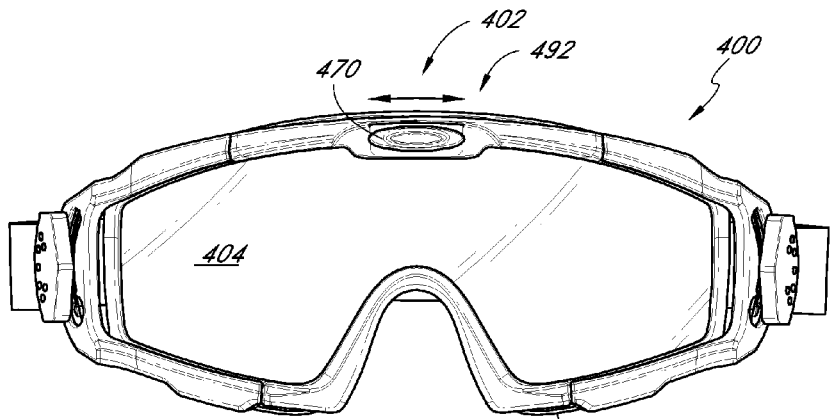
FIG. 30 is a front view of the goggle of FIG. 20 wherein the retention component is in an engaged position, according to an embodiment.
Figure 31:
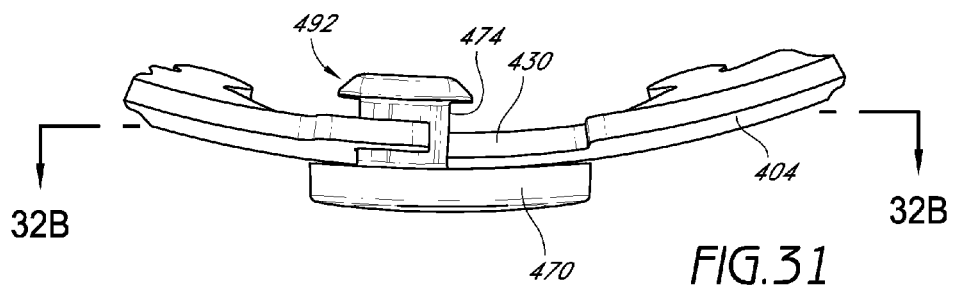
FIG. 31 is a partial top view of the lens and the retention component wherein the retention component is in the engaged position, according to an embodiment.
Figure 32B:
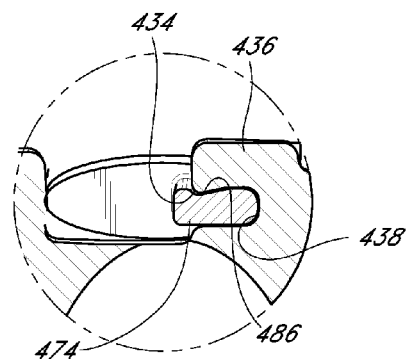
FIG. 32B is a rear cross-sectional view of the lens and the retention component of FIG. 31 taken along lines 32B-32B.
Figure 32A:
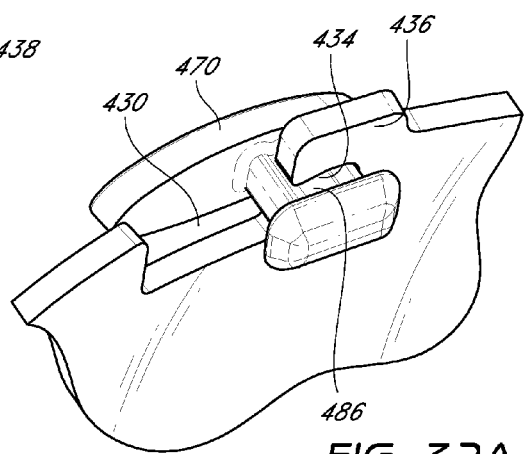
FIG. 32A is a rear perspective view of the lens and the retention component of FIG. 31.

Accordingly, referring to FIG. 30, a front view of the goggle 400 is shown wherein the lens 404 is secured relative to the goggle 400 with the engagement member 470 being positioned in an engaged position 492. Additionally, FIG. 31 is a top view of the engagement member 470 in the engaged position 409 the relative to the slot 430 of the lens 404. Further, FIGS. 32A-B illustrate a rear perspective view and a rear cross-sectional view of the engagement between the mechanism and the lens 404. As shown, in the engaged position 492, the body 474 of the engagement member 470 is disposed within the closed end 438 of the slot 430. Thus, the engagement member 470 can be actuated to engage with the lens 404 to resist and/or prevent relative movement between the frame 408 and the lens 404.

Additionally, in some embodiments, the interaction between the lens 404 and the engagement member 470 can cause the engagement member 470 to be snapped-into place and captured when in the engaged position to thereby form a locking structure or means.

For example, the thickness of the body 474 at the ridge 484 of the engagement member 470 can exceed the spacing or width between the edge or tab 434 and a lower surface of the slot 430 of the lens 404. However, as illustrated in FIGS. 32A-B, the body 474 can be configured to fit within the closed end 438 of the slot 430 provided that the hook portion 436 of the lens 404 deflects slightly upwardly upon insertion of the body 474 toward the closed end 438 of the slot 430. Thus, the body 474 can be urged into the slot 430 and towards the closed end 438 of the slot 430. After initial resistance, the body 474 can be accepted into the slot 430. Once the body 474 is received within the closed end 438 of the slot 430, the hook portion 436 of the lens 404 can rebound to its original position as the edge or tab 434 moves into the recess or indentation 486 of the body 474. At that point, the tab or protrusion of the hook portion 436 can engage with the recess 482 of the body 474 to resist movement of the body 474 out of the slot 430. The engagement member 470 can thereby achieve an engaged position with the lens 404 in a manner that not only resist and/or prevent the movement of the lens 404 relative to the frame 408, but to also resist and/or prevent movement of the engagement member 470 within the slot 430 of the lens 404.

In some embodiments, the engagement member 470 can be biased toward one of the engaged position or the disengaged position. For example, some embodiments can be configured such that the engagement member 470 is acted on by a biasing force or biasing mechanism, such as a spring, that urges the engagement member 470 toward the engaged position. Such a feature may advantageously reduce and/or eliminate the possibility of accidental disengagement of the engagement member 470 with the lens 404. Further, even if a disengaging force is exerted on the engagement member 470 by the user, the disengaging force would need to be constant to maintain the engagement member 470 in the disengaged position while the lens 404 is removed. Otherwise, the engagement member 470 could rebound toward the engaged position, thereby securing the lens 404 relative to the frame 408, which also mitigates accidental disengagement of the engagement member 470 with the lens 404. Such configurations could be used independently of or in cooperation with the locking mechanism discussed immediately above.

Some embodiments of the goggle can also comprise a centroidal vectoring strap tension system, noted above in FIG. 20 as element 406. The centroidal vectoring strap tension system can ensure that when worn, the faceplate of the goggle exerts a generally or substantially uniform pressure against the face of the wearer, even when the strap of the goggle is oriented at an angled or non-horizontal position. In accordance with some embodiments, the faceplate can include a foam or gasket component for enhancing comfort against the wearer's face.

Figure 33:
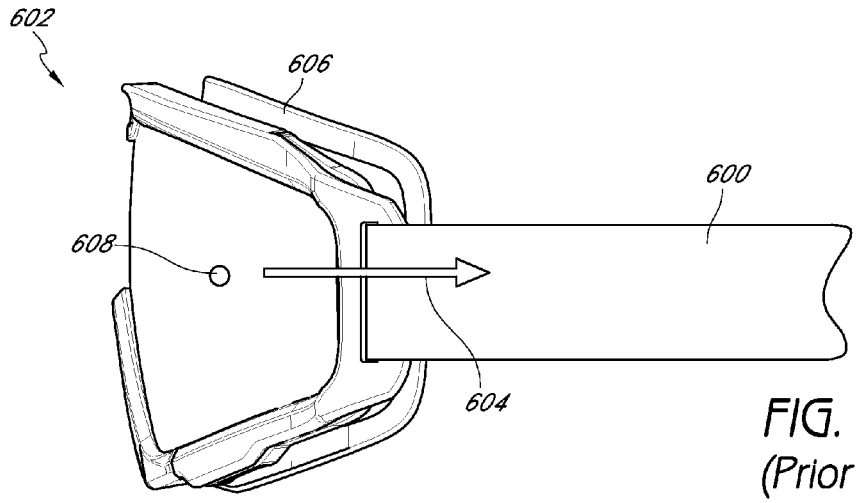
FIG. 33 is a side view of a prior art goggle illustrating a force exerted in a horizontal direction at a centroid of the goggle.
Figure 34:
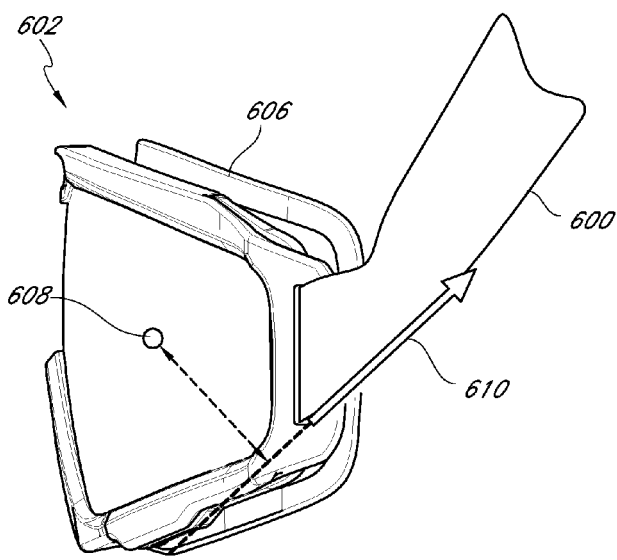
FIG. 34 is a side view of a prior art goggle illustrating a force exerted in a vertical direction and the resultant force created about the centroid of the goggle.
Figure 35:
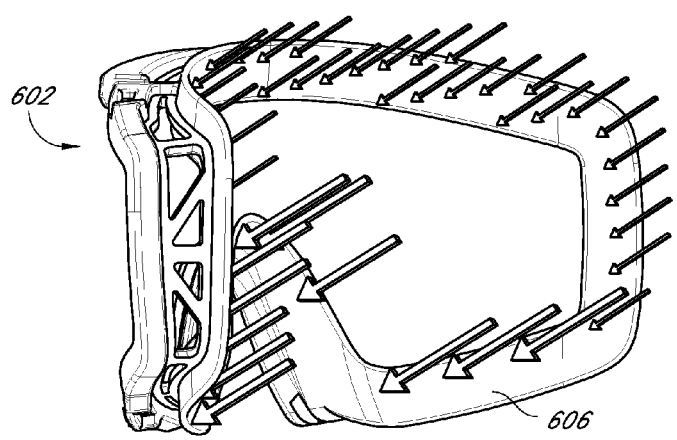
FIG. 35 is a force distribution diagram illustrating representative forces exerted on a faceplate of the goggle of FIG. 34.

FIGS. 33-35 illustrate a prior art goggle having a fixed strap design. Generally, when a strap 600 of a goggle 602 undergoes any degree of stretching during wear, the strap 600 experiences a corresponding tensile load 604 that is transferred as compressive forces by a faceplate 606 of the goggle 602 against the face of the wearer. When the tensile load 604 is oriented in a generally horizontal direction, the compressive forces exerted by the faceplate 606 against the face of the wearer tend to be generally equally distributed about the faceplate 606. This is because the tensile load 604 passes generally through or sufficiently near a centroid 608 or geometric center, center of balance, or center of mass of the faceplate 606 and creates compressive forces whose resultant force passes generally through or sufficiently near the centroid of the faceplate 606. For example, a resultant force may pass sufficiently near the centroid if it passes within about 25 mm of the centroid. A resultant force may also pass sufficiently near the centroid if it passes within between at least about 1 mm and/or less than or equal to about 20 mm of the centroid. Further, a resultant force may pass sufficiently near the centroid if it passes within between at least about 1 mm and/or less than or equal to about 15 mm of the centroid. Furthermore, a resultant force may pass sufficiently near the centroid if it passes within between at least about 2 mm and/or less than or equal to about 10 mm of the centroid. Furthermore, a resultant force may pass sufficiently near the centroid if it passes within about 2 mm, 5 mm, or 10 mm.

As generally shown in FIGS. 33-34, the centroid 608 can generally lie behind the lens generally at a horizontal center of the faceplate. In some embodiments, the centroid 608 can generally be at the center of the goggle, side to side, and slightly above the center, top to bottom. For example, the centroid 608 can generally be spaced slightly rearward and downward relative to a center of a top rim of the faceplate or lens. A horizontal line extending through or sufficiently near the centroid 608 side-to-side can intersect the lateral-most edges of the faceplate or lens or be spaced apart from the lateral edges within a range of about +/−40 mm.

In some embodiments, the centroid 608 can lie anterior to a horizontal (front-to-back) center of the faceplate and above a vertical (top-to-bottom) center of the faceplate. The centroid 608 can be spaced anterior to the horizontal center of the faceplate within a range of between about 1 mm and less than or equal to about 40 mm. Further, the centroid 608 can be spaced anterior to the horizontal center of the faceplate within a range of between about 10 mm and less than or equal to about 20 mm. In some embodiments, the centroid 608 can be spaced about 15 mm anterior to the horizontal center of the faceplate. In some embodiments, the centroid 608 can be spaced above the vertical center of the faceplate within a range of between about 1 mm and less than or equal to about 40 mm. Further, the centroid 608 can be spaced above the vertical center of the faceplate within a range of between about 3 mm and less than or equal to about 20 mm. In some embodiments, the centroid 608 can be spaced about 5 mm above the vertical center of the faceplate.

FIGS. 33-34 illustrate a centroid 608 of the faceplate 606 of the goggle 602. The centroid 608, shown as a sphere, represents the averaged center location of every point on the surface of the faceplate 606 that would contact the wearer's face. The centroid 608 is a function of both area size (magnitude) and three-dimensional distance from every other point. Since every portion of the surface of the faceplate 606 goes into the calculation, there are no discreet "landmarks" that indicate the centroid 608; the entire surface must be analyzed. For the purpose of strap vectoring, the centroid 608 represents the center of balance of the faceplate surface. Centroid calculation can be a cumbersome, tedious summation ideally suited to computerized analysis, and may be completed with a single mouse click with most CAD programs (commonly used by those skilled in the art).

Every unique faceplate shape has a unique centroid. Exact centroids can be calculated for various goggles. In some methods, an accurate digital representation of the faceplate surface is required to quickly calculate the centroid. If the original CAD data is unavailable, a laser scan of the faceplate can be imported into CAD and used to calculate the centroid of the faceplate. This is a readily available method for finding a faceplate centroid, but other methods of achieving the same result may be conceived by those skilled in the art. Further, the centroid calculation can also take into account the presence of a foam seal or gasket component that is frequently used on the faceplate of the goggle. For example, the centroid calculation could be based on the seal or gasket surface for a relatively rigid seal or gasket. Further, the centroid could be based on the faceplate (thereby ignoring the seal or gasket surface) for soft or highly compressible seals.

The distribution of compressive forces along the surface of the faceplate 606 can also be identically represented with a resultant force (equal to the pressure times the faceplate area). In a perfect condition, the distribution of compressive forces is even along the surface of the faceplate, providing a maximum level of comfort for the wearer, and the resultant force is directed through or sufficiently near the geometrical centroid of the faceplate. Further, as shown in FIG. 33, the strap 600 undergoes generally or substantially uniform stretching along the top and bottom thereof, thus ensuring efficient wear and maximum useful life of the strap 600.

However, when the resultant force does not pass through or sufficiently near the centroid, the distribution of compressive forces on the faceplate is generally uneven, which is uncomfortable for the wearer. An example of such a condition is represented in FIGS. 34-35. This condition may be encountered when applications require that the strap 600 be oriented in a non-horizontal direction. For example, when a goggle is worn with a helmet, the goggle strap 600 may be positioned at an angled or non-horizontal position, as shown in FIG. 34.

With reference to FIG. 34, the fixed strap design of the goggle 602 causes the strap 600 to buckle or experience a tensile force 610 that creates generally or substantially non-uniform stresses along the top and bottom of the strap 600. While the bottom of the strap 600 is experiencing significant tensile loading, the top of the strap 600 can be experiencing a lesser degree of tensile loading or none at all. Such loading is represented by the force vector or tensile force 610. As illustrated, the tensile load 610 will create a torque or moment about the centroid 608 of the faceplate 606 of the goggle 602.

As a result, the compressive forces exerted by the faceplate 606 against the face of the wearer will be generally uneven, as shown in FIG. 35. This creates uncomfortable high pressure on the cheeks and low pressure across the top portion, potentially detaching the faceplate from the forehead. A resultant force of the illustrated forces in FIG. 35 does not pass through or sufficiently near the centroid of the faceplate 606. The distribution of compressive forces is uneven on the faceplate 606, with maximum compression occurring along a lower portion of the faceplate 606. Therefore, the wearer will experience much higher compressive force along the lower portion of the goggle 602 which will create discomfort and stress. Further, the strap 600 may tend to experience reduced useful life and uneven wear due to the imbalance of forces exerted along the top and bottom of the strap 600.

Some prior art goggles use a rotatable or pivot connection between the strap and the frame of the goggle. In an angled position, the pivot aligns the strap with the load and prevents buckling, but the tensile load is still directed in a non-centroidal direction, which results in a torque or moment generated about the centroid of the goggle. The torque about the centroid, though reduced compared with the fixed strap design, still results in uneven reaction pressure on the faceplate. This also creates uncomfortable high pressure on the cheeks and low pressure across the top portion, potentially detaching the faceplate from the forehead.

Figure 36:
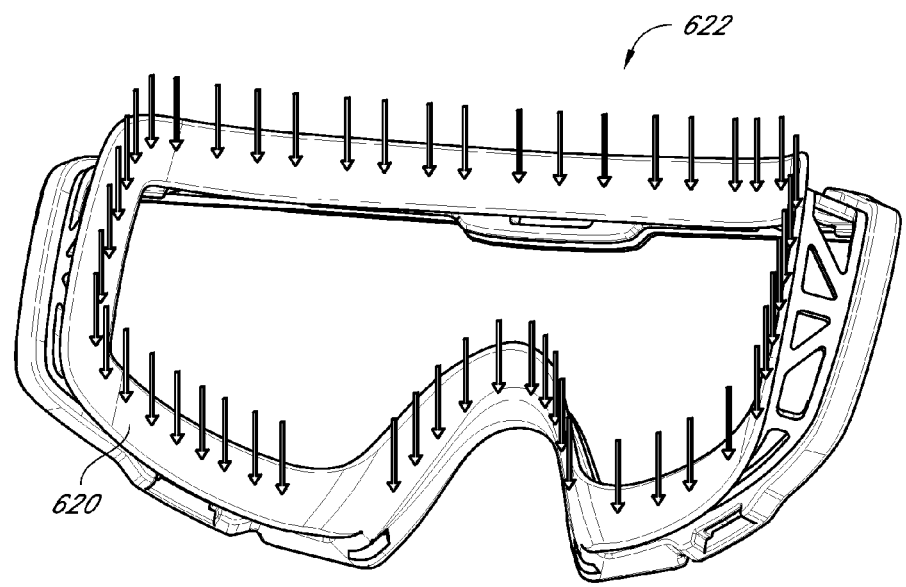
FIG. 36 is a force distribution diagram illustrating representative forces exerted on a faceplate of a goggle wherein the forces are in equilibrium, according to an embodiment disclosed herein.
Figure 37:
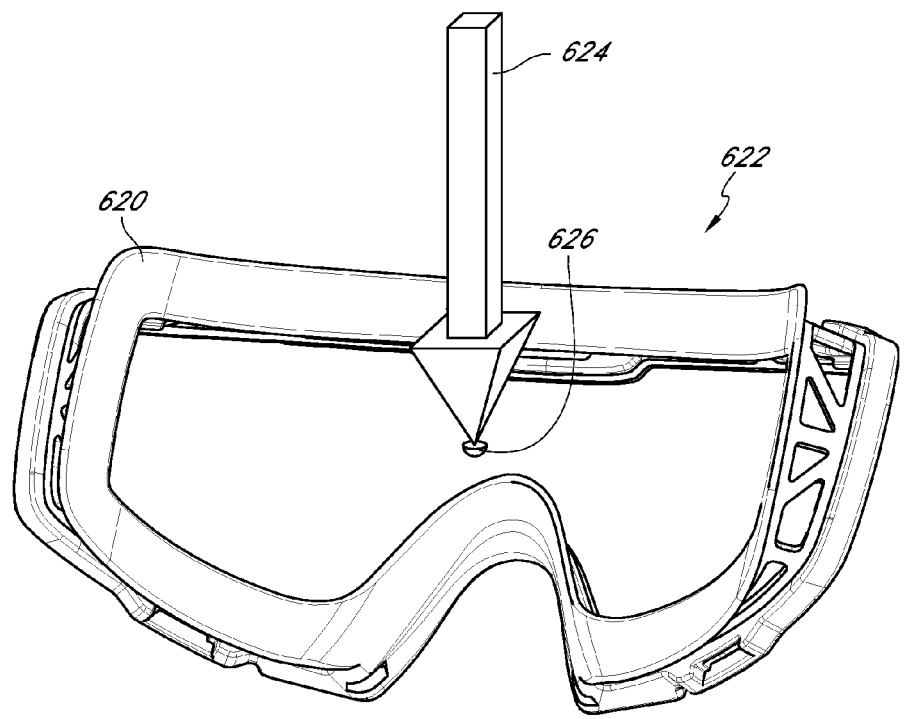
FIG. 37 is a simplified force distribution diagram illustrating a single force vector that is representative of the equilibrium forces shown in FIG. 36, wherein the single force vector is exerted through or sufficiently near a centroid of the goggle, according to an embodiment.
Figure 38:
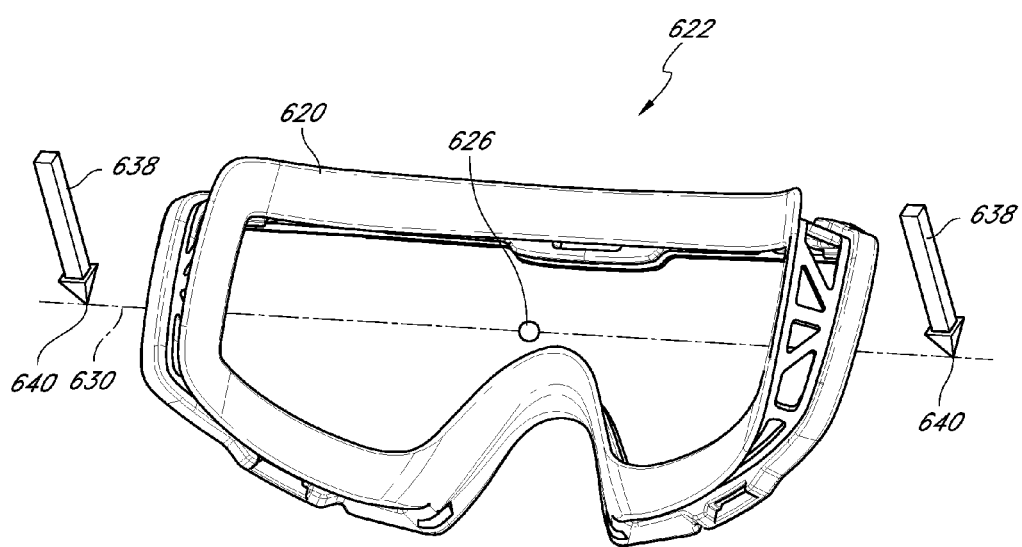
FIG. 38 is a force distribution diagram illustrating a pair of force vectors passing through a line that passes through or sufficiently near the centroid of the goggle shown in FIG. 36, according to an embodiment.

With reference to FIGS. 36-38, some embodiments disclosed herein reflect the realization that in order to maximize comfort and optimize the wear of the strap of the goggle, compressive forces exerted by the faceplate against the wearer's face should be generally evenly distributed. FIG. 36 illustrates a diagram wherein forces are distributed generally equally along a faceplate 620 of a goggle 622. The diagram of FIG. 36 depicts the ideal as-worn condition, where the wearer's face pressure is evenly or substantially evenly distributed across the entire face plate (i.e., no high-pressure areas or pressure gradients).

As shown in FIG. 37, the perfect condition of FIG. 36 (in which the distribution of compressive forces is even along the faceplate 620) can also be identically represented with a resultant force 624 directed through or sufficiently near a geometrical centroid 626 of the face plate 620. Accordingly, FIGS. 36-38 illustrate a condition in which the resultant force is directed through or sufficiently near the centroid 626 and the compressive forces are evenly or substantially evenly balanced across the entire faceplate surface. The resultant force 624 is representative of the product of the summation of the forces illustrated in FIG. 36 and the faceplate area.

Figure 39:
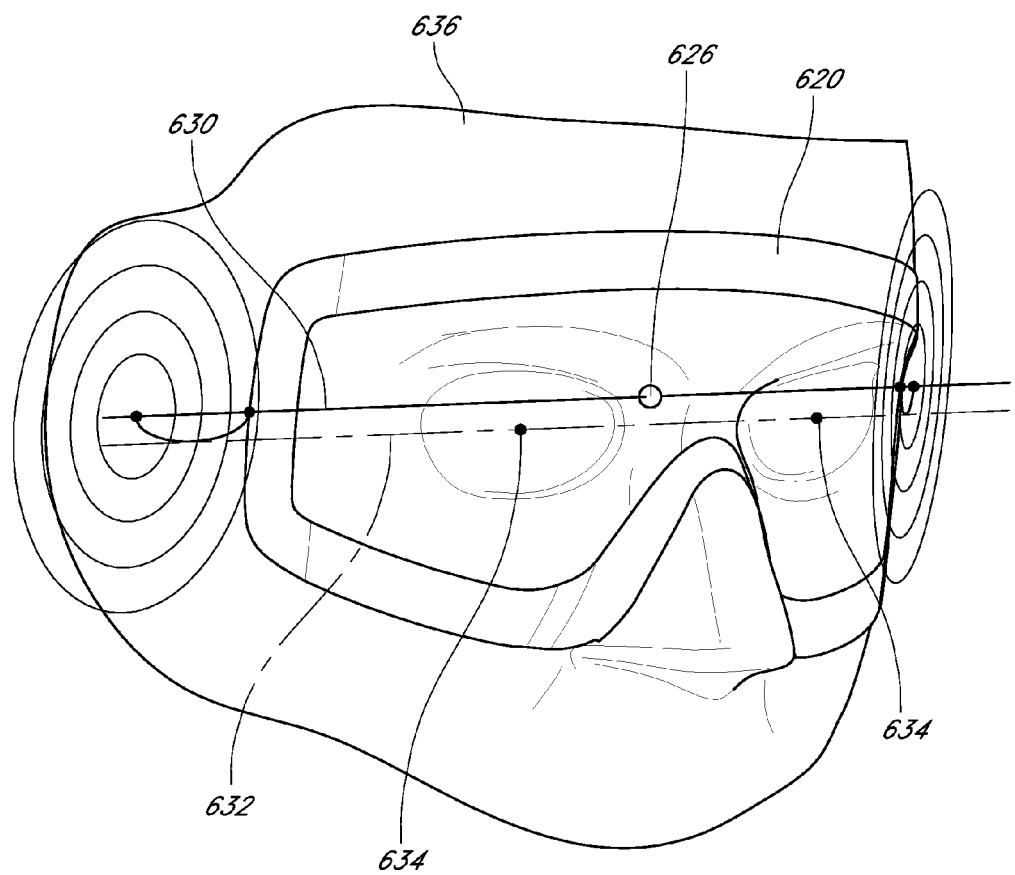
FIG. 39 is a perspective view illustrating a horizontal axis passing through or sufficiently near the centroid of the goggle, according to an embodiment.

FIGS. 38-39 illustrate another aspect of embodiments disclosed herein. In FIG. 38, a horizontal centroidal axis 630 is shown. The horizontal centroidal axis 630 can be determined by establishing an interception axis 632 that intercepts both pupils 634 of the desired headform 636, as shown in FIG. 39. A parallel or coincident axis that passes through or sufficiently near the centroid 626 of the faceplate 620 is the horizontal centroidal axis 630.

In some embodiments, the horizontal centroidal axis 630 can intersect with the centroid 626. The horizontal centroidal axis 630 can also be oriented generally perpendicular relative to a vertical centerline or axis of symmetry of the faceplate 620. As generally shown in FIGS. 38-39, the centroid 626 can generally lie behind the lens generally at a horizontal center of the faceplate. In some embodiments, the centroid 626 can generally be at the center of the goggle, side to side, and slightly above the center, top to bottom. For example, the centroid 626 can generally be spaced slightly rearward and downward relative to a center of a top rim of the faceplate or lens. A horizontal line extending through or sufficiently near the centroid 626 in a side-to-side direction can intersect the lateral-most edges of the faceplate or lens or be spaced apart from the lateral edges within a range of about +/−40 mm. Ideally the reference point is coincident with the centroid.

In some embodiments, the centroid 626 can lie anterior to a horizontal (front-to-back) center of the faceplate and above a vertical (top-to-bottom) center of the faceplate. The centroid 626 can be spaced anterior to the horizontal center of the faceplate within a range of between about 1 mm and less than or equal to about 40 mm. Further, the centroid 626 can be spaced anterior to the horizontal center of the faceplate within a range of between about 10 mm and less than or equal to about 20 mm. In some embodiments, the centroid 626 can be spaced about 15 mm anterior to the horizontal center of the faceplate. In some embodiments, the centroid 626 can be spaced above the vertical center of the faceplate within a range of between about 1 mm and less than or equal to about 40 mm. Further, the centroid 626 can be spaced above the vertical center of the faceplate within a range of between about 3 mm and less than or equal to about 20 mm. In some embodiments, the centroid 626 can be spaced about 5 mm above the vertical center of the faceplate.

FIG. 38 illustrates an identical representation of the ideal as-worn condition as shown in the diagram of FIG. 37. However, in FIG. 38, half of the resultant force 624 is applied through half-forces 638 applied at each of two symmetrically opposed points 640. The points 640 are each equidistant from the centroid 626, through a horizontal centroidal axis 630 that passes through or sufficiently near the centroid 626 and that is parallel or coincident to the interception axis 632. Thus, the embodiment shown in FIG. 38 would provide superior results and even pressure distribution across the faceplate 620 because the forces 638 are directed through or sufficiently near the centroid 626 to evenly or substantially evenly balance the entire surface of the faceplate 620.

Further, the compressive forces across the surface of the faceplate 620 need not be perfectly balanced for centroidal strap vectoring to be effective. For example, as discussed further below, imbalance of compressive forces can be present within an acceptable range, which would still allow the wearer to benefit from the comfort provided by centroidal strap vectoring.

Figure 40:
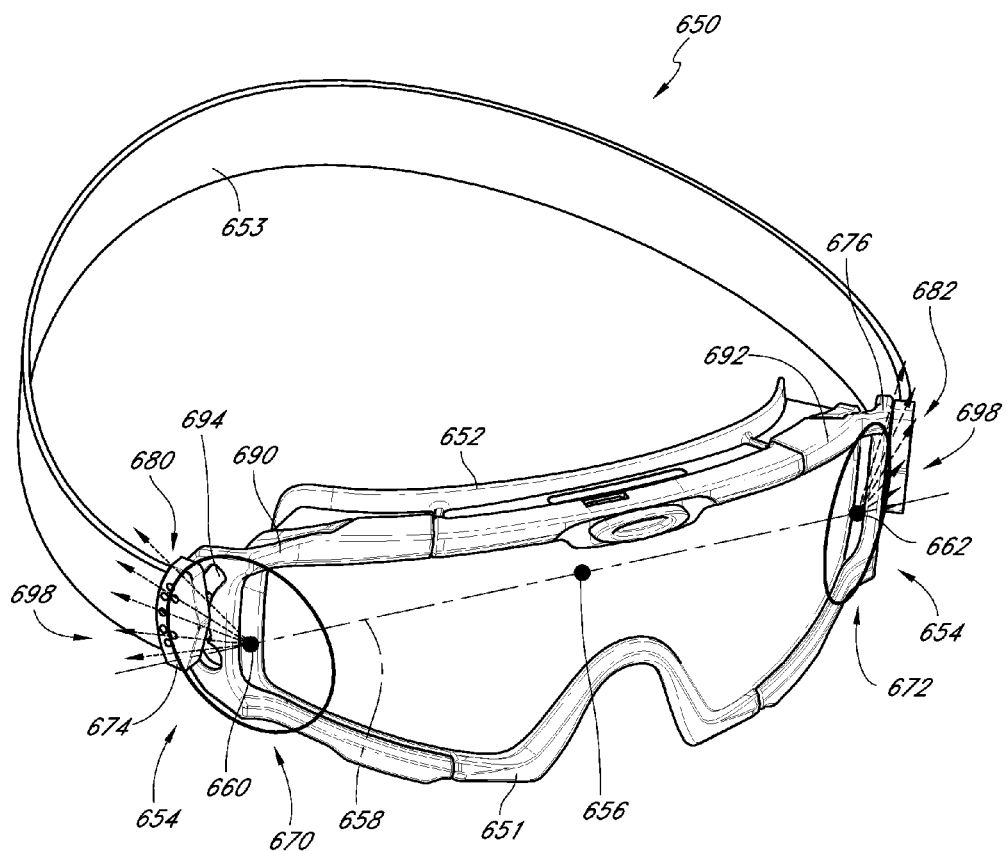
FIG. 40 is a perspective view of a goggle illustrating rotational angles of a strap of the goggle about a centroidal axis, according to an embodiment.

Referring now to FIG. 40, an embodiment of a goggle 650 having a frame 651, a faceplate 652, a strap 653, and a centroidal vectoring strap system 654 is illustrated. The faceplate 652 of the goggle 650 can also define a centroid 656, which can be used to define a horizontal centroidal axis 658. Similar to the illustration of FIG. 39, the horizontal centroidal axis 658 can be parallel or coincident to the interception axis 632 that passes generally through the pupils of the wearer.

The horizontal centroidal axis 658 can be used as a reference point for first and second center points 660, 662 disposed at respective first and second sides 670, 672 of the goggle 650. The first and second center points 660, 662 can be disposed along a guide axis that is generally parallel or coincident relative to the horizontal centroidal axis 658. In the embodiment of FIG. 40, the first and second center points 660, 662 are shown as lying on the horizontal centroidal axis 658 (e.g., the guide axis can be generally collinear with the horizontal centroid axis 658 in some embodiments). However, the guide axis and the first and second center points 660, 662 can also be spaced from the horizontal centroidal axis 658, as discussed below. The first and second center points 660, 662 can be used as centers of the radius of curvature of an arcuate travel path along which ends of the strap 653 can move.

The first and second center points 660, 662 can be spaced equidistant from the centroid 656. In some embodiments, the spacing or distance of the first and second center points 660, 662 from the centroid 656 is configured to overlay a structure of the goggle 650. For example, the first and second center points 660, 662 can be overlaid onto first and second connecting portions or outriggers of the goggle 650, whereat the strap 653 is attached.

The first and second strap engagement mechanisms 680, 682 can be configured to rotate relative to the frame 651 of the goggle 650. In some embodiments, the first and second strap engagement mechanisms 680, 682 can rotate about the first and second center points 660, 662. In some embodiments, rotation of the first and second strap engagement mechanisms 680, 682 about the first and second center points 660, 662 can ensure that the resultant force of the compressive forces exerted by the faceplate 652 passes generally through or sufficiently near the centroid 656 of the faceplate 652, regardless of the angular position of the strap 653 or the radial distance of the first and second strap engagement mechanisms 680, 682 from the first and second center points 660, 662. Accordingly, the compressive forces can tend to be evenly or substantially evenly balanced across the entire surface of the faceplate 652 to promote greater comfort and less fatigue for the wearer and proper seating of the entire faceplate area and thereby reduce and/or eliminate any gapping between the user's face and the faceplate.

In some embodiments, the coupling between the first and second strap engagement mechanisms 680, 682 and the frame 651 can be displaced or spaced from the first and second center points 660, 662. For example, the coupling can be spaced at a radial distance defined as a radius of curvature of the first and second strap engagement mechanisms 680, 682. In some embodiments, the radial spacing and rotational alignment can ensure that compressive forces are evenly or substantially evenly balanced and a resultant force passes through or sufficiently near the centroid 656.

Further, although in some embodiments, the center points 660, 662 (and the guide axis) can be located along the horizontal centroidal axis 630, even distribution of the compressive forces along the surface of the faceplate can also be achieved when the center points 660, 662 are spaced between at least about 0.0 mm and/or less than or equal to about 8 mm from the horizontal centroidal axis 658. Further, in some embodiments, even distribution of the compressive forces along the surface of the faceplate can also be achieved when the center points 660, 662 are spaced between at least about 2 mm and/or less than or equal to about 6.35 mm from the horizontal centroidal axis 658. Furthermore, in some embodiments, even distribution of the compressive forces along the surface of the faceplate can also be achieved when the center points 660, 662 are spaced about 3.5 mm from the horizontal centroidal axis 658.

For example, referring again to FIG. 40, in some embodiments, the goggle 650 can comprise first and second outriggers 690, 692 that can be coupled to the first and second sides 670, 672 of the frame 651. The first and second outriggers 690, 692 can be coupled with the first and second strap engagement mechanisms 680, 682. The first and second outriggers 690, 692 can be configured to allow rotatable movement of the first and second strap engagement mechanisms 680, 682 relative to the frame 651.

In some embodiments, the first and second outriggers 690, 692 can comprise respective first and second elongate guide slots 694, 696. The first and second elongate guide slots 694, 696 can be configured to receive at least a portion of the first and second strap engagement mechanisms 680, 682 in order to rotatably couple first and second strap engagement mechanisms 680, 682 with the first and second outriggers 690, 692. Thus, the first and second strap engagement mechanisms 680, 682 can be spaced from the first and second center points 660, 662.

When coupled together, the first and second strap engagement mechanisms 680, 682 can slide within the first and second elongate guide slots 694, 696. The first and second strap engagement mechanisms 680, 682 can be adjusted through a range of strap adjustment angles, represented by the directional arrows generally referred to by element 698. According to some embodiments, the interaction between the first and second elongate guide slots 694, 696 and the first and second strap engagement mechanisms 680, 682 can enable tensile forces exerted on the strap 653 to have a resultant force that passes through or sufficiently near the centroid 656 of the faceplate 652.

The first and second elongate guide slots 694, 696 can define an elongate travel path along which the first and second strap engagement mechanisms 680, 682 can move. In some embodiments, the first and second strap engagement mechanisms 680, 682 can be positioned at any point along the travel path and still transfer tensile forces exerted on the strap 653 to the first and second outriggers 690, 692 such that a resultant force passes through or sufficiently near the centroid 656 of the faceplate 652. In some embodiments, the first and second strap engagement mechanisms 680, 682 can be positioned at symmetric or identical locations within the first and second elongate guide slots 694, 696 to ensure that the transfer of tensile forces produces a resultant force that passes through or sufficiently near the centroid 656 of the faceplate 652.

Figure 41:
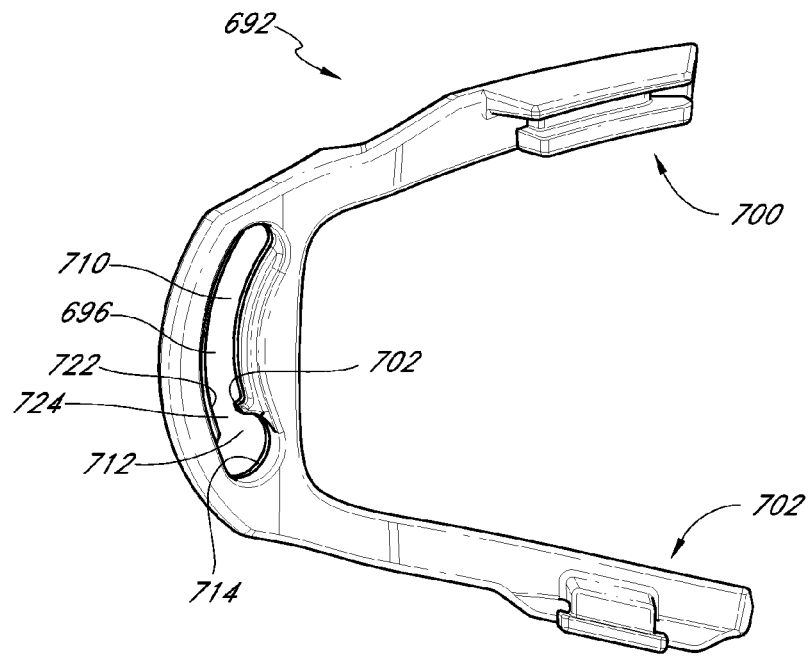
FIG. 41 is a rear perspective view of an outrigger of the goggle, according to an embodiment.

In some embodiments, the first and second elongate guide slots 694, 696 can define an arcuate travel path along which the first and second strap engagement mechanisms 680, 682 can move. Such an embodiment is illustrated in FIGS. 40-41. Although the travel path can be straight or linear, the travel path can configured to be curved or arcuate. In some embodiments, the adjustment angle or arc range of the travel path can allow the first and second strap engagement mechanisms 680, 682 to a strap adjustment angle within a range of between at least about 30 degrees below horizontal (−30 degrees) and less than or equal to about 50 degrees above horizontal. In some embodiments, the arc range of the travel path can allow the first and second strap engagement mechanisms 680, 682 to move between at least about 10 degrees below horizontal and less than or equal to about 45 degrees above horizontal. Further, in some embodiments, the arc range of the travel path can allow the first and second strap engagement mechanisms 680, 682 to move between at least about 10 degrees below horizontal and less than or equal to about 40 degrees above horizontal. Accordingly, the length of the travel path can be calculated based on the arc range and the curvature of the first and second elongate guide slots 694, 696.

In embodiments having an arcuate travel path, the curvature of the travel path can be generally defined by the inverse of the radius of a circle having a center point located at the respective one of the first or second center points 660, 662. Further, in embodiments wherein the arcuate travel path lies along a circle, the radius of the circle can be varied in order to vary the curvature of the arcuate travel path, such as that represented in FIG. 39.

Thus, in some embodiments, the first and second guide slots 694, 696 can be generally linear or have a substantially radius of curvature that is constant or variable. In some embodiments, the radius can be between about 10 mm and less than or equal to about 50 mm. In some embodiments, the radius can be between about 16 mm and less than or equal to about 35 mm. In some embodiments, the radius can be about 20.8 mm. However, in some embodiments, as long as the radius places the center point of articulation generally adjacent to or coincident with the centroidal axis 658, the first and second guide slots 694, 696 can be configured to define any desired radius of curvature to achieve a desired strap articulation.

For example, FIG. 39 illustrates a series of concentric circles having arcs of rotation that represent potential arcuate travel paths along which the first and second strap engagement mechanisms 680, 682 can be moved and/or rotated. The first and second center points 660, 662 can serve as a geometric center of circles or arcs of rotation 674, 676 of respective first and second strap engagement mechanisms 680, 682. The arcs of rotation 674, 676 each define a radius of curvature that is centered on the first and second center points 660, 662. The radius of curvature can be a desired length, which may be dependent on the overall size and configuration of the goggle. Although in some embodiments, the center points 660, 662 can be located on the horizontal centroidal axis 630, even distribution of the compressive forces along the surface of the faceplate can also be achieved when the center points 660, 662 are spaced on or closely to the horizontal centroidal axis 658.

In some embodiments wherein the elongate guide slots 694, 696 are arcuate, the radius of curvature of the guide slots 694, 696 can be centered on the first and second center points 660, 662. Further, the radii thereof can be configured as desired, according to the configuration of the goggle. For example, the first and second center points 660, 662 can be located along a guide axis that is generally parallel, coincident, or coaxial relative to the horizontal centroidal axis 630. As noted above, the horizontal centroidal axis 630 can be generally parallel or coincident relative to the interception axis 632. Further, in some embodiments, the horizontal centroidal axis 630 can be positioned posteriorly relative to the at least one lens. Furthermore, the horizontal centroidal axis can be substantially coincident with the centroid 656, which can be spaced relative to various structures and geometric features of the lens, frame, faceplate, etc. within certain ranges.

Accordingly, the first and second strap engagement mechanisms 680, 682 can direct the force vector for each mechanism 680, 682 through or sufficiently near the respective first and second center points 660, 662 due to the movement of the first and second strap engagement mechanisms 680, 682 along such arcs of rotation. Further, in some embodiments, the force vectors can be directed generally through or sufficiently near the centroid 626 of the faceplate 620, thereby improving the comfort and pressure distribution of the goggle.

As generally illustrated, each circle shown in FIG. 39 defines a different radius. Further, the guide slots 694, 696 can have a substantially constant, but arbitrary radius of curvature. In some embodiments, the center of the radius of curvature (the center points 660, 662) is located generally on the horizontal centroidal axis 630. As noted above, even distribution of the compressive forces along the surface of the faceplate can also be achieved when the center of the radius of curvature is positioned closely to the horizontal centroidal axis 658, such as between at least about 0.0 mm and/or less than or equal to about 8 mm. Further, in some embodiments, even distribution of the compressive forces along the surface of the faceplate can also be achieved when the center points 660, 662 are spaced between at least about 2 mm and/or less than or equal to about 6.35 mm from the horizontal centroidal axis 658. Furthermore, in some embodiments, even distribution of the compressive forces along the surface of the faceplate can also be achieved when the center points 660, 662 are spaced about 3.5 mm from the horizontal centroidal axis 658.

In some embodiments, the radius of the guide slots 694, 696 can be between at least about 10 mm and/or less than or equal to about 40 mm. In some embodiments, the radius of the guide slots 694, 696 can be between at least about 15 mm and/or less than or equal to about 30 mm. In some embodiments, the radius of the guide slots 694, 696 can be between at least about 20.8 mm. However, any radius may be chosen to achieve the same strap vectoring function, as long as the radius is centered on the horizontal centroidal axis 658.

The arcuate travel path of the first and second elongate guide slots 694, 696 can also define an arc length configured to allow a desired angular displacement of the first and second strap engagement mechanisms 680, 682. For example, during typical use of the goggle 650, the strap 653 may be worn at the generally horizontal position. For purposes of illustration, the horizontal position can be used as a "zeroing angular position" such that angular displacement above horizontal is positive and angular displacement below horizontal is negative.

Accordingly, in some embodiments, the strap 653 can be rotated to a strap adjustment angle about the arcs of rotation 674, 676 within an arc range of between at least about –20 degrees and/or less than or equal to about 60 degrees. In some embodiments, the strap 653 can be rotated to a strap adjustment angle about the arcs of rotation 674, 676 within an arc range of between at least about –10 degrees and/or less than or equal to about 40 degrees. Further, in some embodiments, the first and second outriggers 690, 692 can be interchangeable such that the wearer can select a desired outrigger having a guide slot design that not only provides a desired arc length, but that also provides a desired curvature of the arcuate travel path. Accordingly, the goggle can be provided as an interchangeable system or kit.

Accordingly, in some embodiments, the centroidal vectoring strap system 654 can ensure that the compressive forces exerted by the faceplate 652 of the goggle 650 are generally or substantially uniform through a range of strap adjustment angles, such as the ranges noted above. Further, the centroid vectoring strap system 654 can be selectively modified to provide a desired length and/or curvature of the travel path of the guide slot.

A method of determining whether a goggle utilizes centroidal strap vectoring can include: accurately scanning the faceplate and strap attachment into a CAD program; orienting the parts with respect to a chosen headform and the associated horizontal axis; determine centroid and centroidal horizontal axis of the faceplate; and determining the center of the strap attachment radius of action. If the center of the radius of curvature exceeds a distance, such as 6.35 mm, from the horizontal centroidal axis, it is possible that the goggle is not set up for centroidal strap vectoring. However, other methods and procedures for determining whether centroidal strap vectoring is used can also be employed.

Further, a goggle can be set up for centroidal strap vectoring even if the compressive forces across the surface of the faceplate, seal, or gasket are not perfectly balanced. Some embodiments can be configured such that the compressive forces can be substantially balanced or have a variance within an acceptable range for a given non-horizontal strap position or adjustment angle that falls within the adjustment angle or arc ranges discussed herein. In some embodiments, the goggle can provide superior balancing of the compressive forced throughout a range of strap positions or adjustment angles.

For example, the centroidal strap vectoring can be effective to provide a distribution of forces with a maximum variance within an acceptable range for a given strap position or adjustment angle. In some embodiments, the maximum variance can be between about 2% and/or less than or equal to 20% for a given strap position or adjustment angle. In some embodiments, the distribution of forces can also have a maximum variance of between about 3% and/or less than or equal to 10% for a given strap position or adjustment angle. Further, the distribution of forces can have a maximum variance of between about 4% and/or less than or equal to 8% for a given strap position or adjustment angle. The maximum variance can be calculated based on an average or median force and the percent deviation from that value, of forces measured at other areas across the faceplate, seal, or gasket. These values can be based forces generated using a typical as-worn strap tension. Accordingly, centroidal strap vectoring can be present and effective in a goggle to balance compressive forces within an acceptable range, which allows the wearer to benefit from the comfort provided by centroidal strap vectoring.

Figure 42:
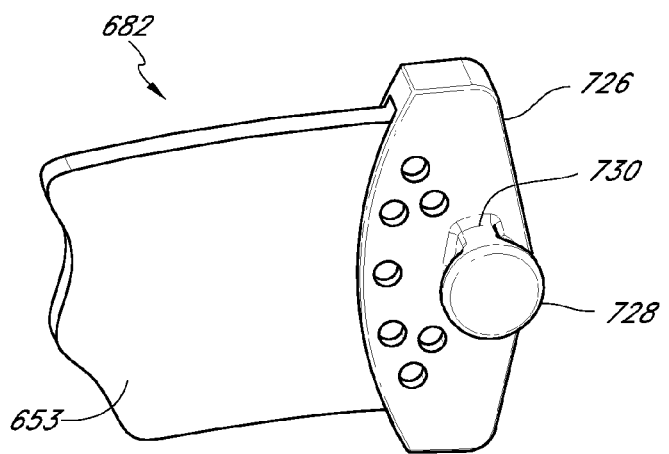
FIG. 42 is a perspective view of a strap engagement mechanism, according to an embodiment.

Referring now to FIGS. 41-44, an embodiment of an outrigger and a strap engagement mechanism are provided shown in detail. FIG. 41 illustrates the second outrigger 692 of the goggle 650 shown in FIG. 40. FIG. 42 illustrates the second strap engagement mechanism 682 attached to the strap 653 of the goggle 650 shown in FIG. 40.

In the illustrated embodiment, the outrigger 692 comprises upper and lower engagement arms 700, 702. The upper and lower engagement arms 700, 702 can be configured to be coupled with corresponding upper and lower portions of the frame 651. Further, the outrigger 692 can comprise the guide slot 696. As illustrated, the guide slot 696 defines a generally arcuate travel path. The guide slot 696 also defines an upper portion 710 and a lower portion 712. The lower portion 712 of the guide slot 696 can comprise an enlarged opening 714 into which a portion of the strap engagement mechanism can be inserted. In some embodiments, the upper portion 710 of the guide slot 696 can be narrower than the lower portion 712 thereof in order to prevent or resist disengagement of the portion of the strap engagement mechanism with the guide slot 696.

For example, the guide slot 696 can also comprise a tooth, protrusion, or tab 720 that can limit or control movement of the strap engagement mechanism within the guide slot 696. The tooth, protrusion, or tab 720 can be positioned adjacent to the lower portion 712 of the guide slot 696, above the enlarged opening 714. The tooth, protrusion, or tab 720 and an opposing edge 722 of the guide slot 696 can define a portion of narrowed width or a gate 724 through which the portion of the strap engagement mechanism must pass in order to access and move within the remainder of the guide slot 696.

FIG. 42 illustrates a perspective view of the second strap engagement mechanism 682 and the strap 653. The second strap engagement mechanism 682 can comprise an engagement body 726 that can be coupled to an end of the strap 653. The second strap engagement mechanism 682 can also comprise an engagement pin or member 728 extending from the body 726. The engagement member 728 can comprise a neck 730. The engagement member 728 can be configured to engage with the guide slot 696 of the second outrigger 692.

Figure 43:
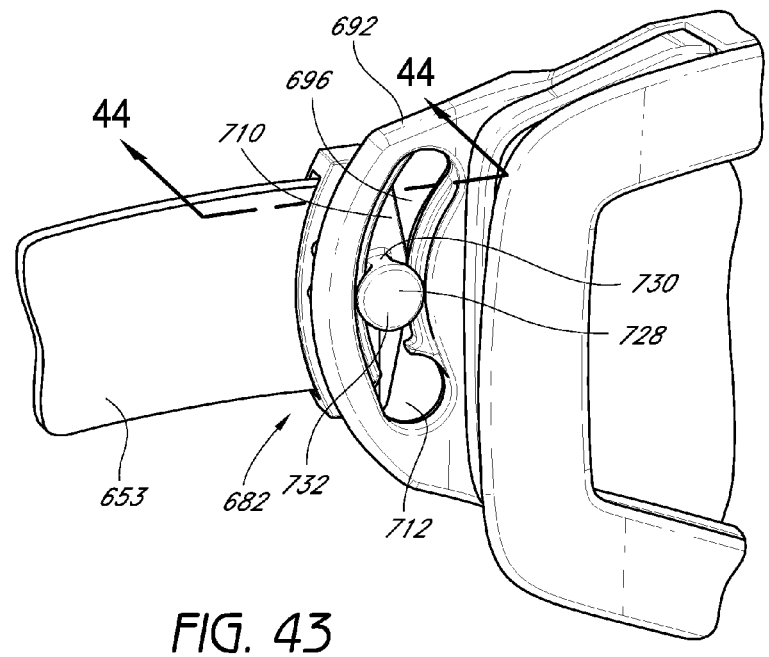
FIG. 43 is a perspective view of the strap engagement mechanism of FIG. 42 assembled with the outrigger of FIG. 41, according to an embodiment.

FIG. 43 illustrates a perspective view of the engagement between the second strap engagement mechanism 682 and the second outrigger 692. Once the engagement member 728 of the second strap engagement mechanism 682 is coupled with the guide slot 696, the second strap engagement mechanism 682 can slide within the guide slot 696 in order to allow the angular position of the strap 653 to be adjusted. In order to couple the second strap engagement mechanism 682 with the guide slot 696, the engagement member 728 can be inserted into the enlarged opening 714 of the guide slot 696. The neck 730 can define a cross-sectional profile that enables the neck 730 to move within the guide slot 696. Further, the engagement member 728 can comprise a wide end portion 732 whose cross-sectional profile exceeds that of the upper portion 710 of the guide slot 696. Thus, once the engagement member 728 is coupled with the guide slot 696 and positioned in the upper portion 710 of the guide slot 696, the second outrigger 692 will be captured between the end portion 732 and the body 726 of the second strap engagement mechanism 682.

Figure 44:
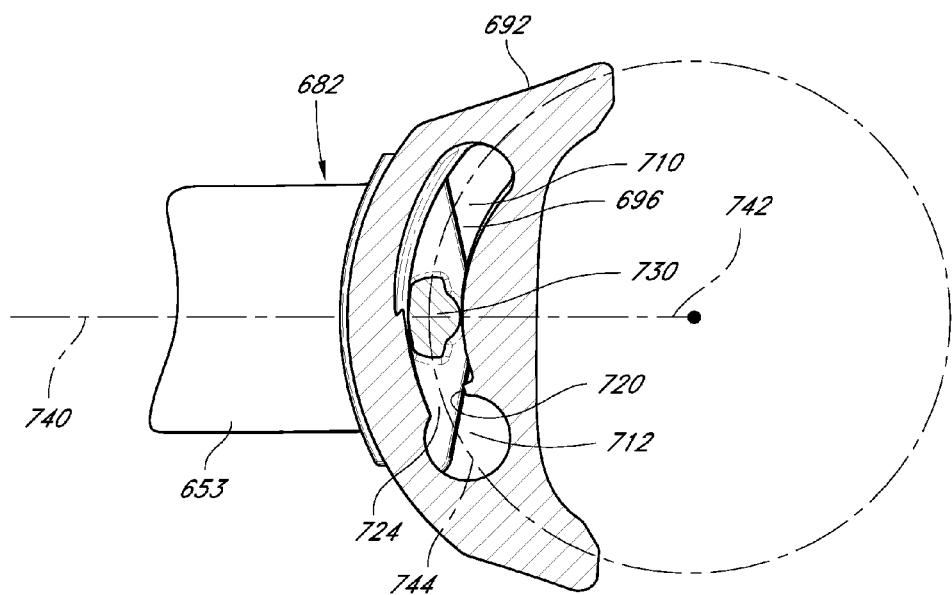
FIG. 44 is a cross-sectional view of the strap engagement mechanism and outrigger assembly taken along section lines 44-44 of FIG. 43.

FIG. 44 illustrates a cross-sectional side view of the guide slot 696 in which the neck 730 of the second strap engagement mechanism 682 is disposed within the guide slot 696. In some embodiments, the cross-sectional profile of the neck 730 can be configured such that the neck 730 can rotated to a position at which the passing profile or width of the neck 730 is less than or equal to the width of the portion of narrowed width or gate 724, thus allowing passage of the neck 730 through the gate 724. In some embodiments, a longitudinal axis 740 of the second strap engagement mechanism 682 and the strap 653 may be misaligned with a radius 742 of the arc of curvature of the guide slot 696 in order to accomplish passing the neck 730 through the gate 724. However, when the strap 653 is positioned in the as-worn orientation (as shown in FIGS. 44-45), the longitudinal axis 740 is aligned with the radius 742 in order to preserve the even distribution of pressure throughout the faceplate 652, as discussed herein.

Advantageously, after the neck 730 is inserted into the enlarged opening 714 and moved past the gate 724, the neck 730 can be configured such that the passing profile or width of the neck 730 exceeds the width of the gate 724 when the longitudinal axis 740 is aligned with the radius 742. This position is shown in FIG. 44. Further, it can be seen that if the neck 730 were to move downwardly toward the lower portion 712 of the guide slot 696 while the longitudinal axis 740 maintains alignment with the radius 742 of arc 744 (during motion through the angular range), the neck 730 will not be permitted to move beyond the gate 724. This scenario can be representative of typical adjustments or movement of the strap 653 during use of the goggle 650. Thus, the unique configuration of the neck 730 and the guide slot 696 can allow the second strap engagement mechanism 682 to be coupled with the second outrigger 692 while the goggle 650 is not being worn, but also resist and/or prevent unintentional disengagement of the second strap engagement mechanism 682 with the second outrigger 692 while the goggle 650 is being worn.

Figure 45:
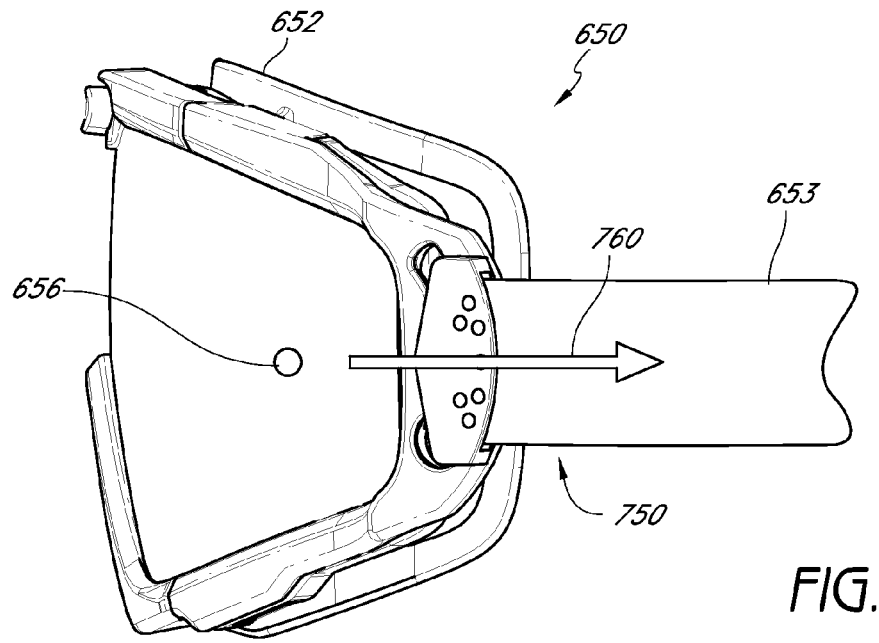
FIG. 45 is a side view of the goggle of FIG. 40, illustrating a force exerted in a horizontal direction at a centroid of the goggle, according to an embodiment.
Figure 46:
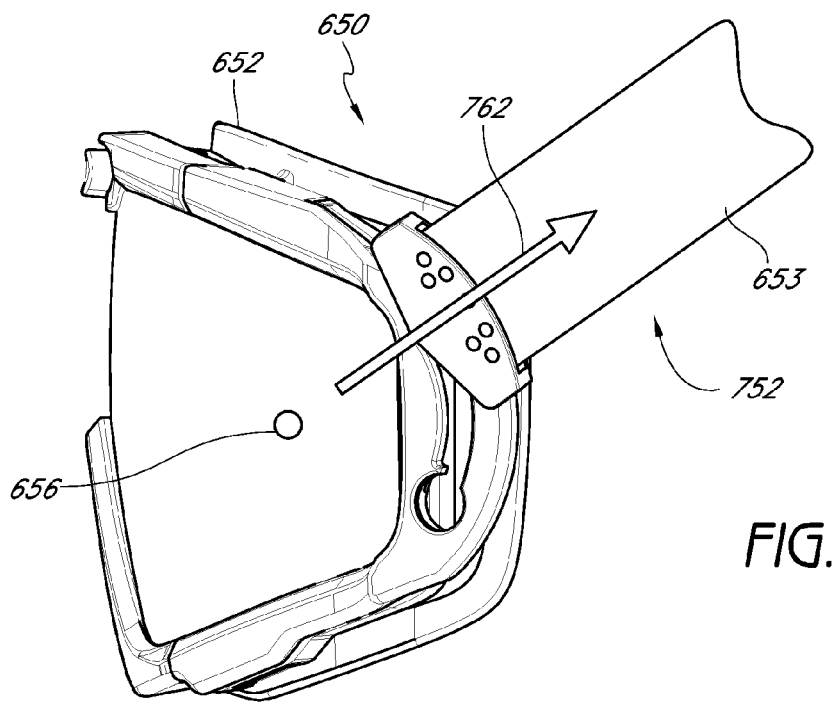
FIG. 46 is a side view of the goggle of FIG. 40, illustrating a force exerted in a vertical direction, according to an embodiment.

FIGS. 45 and 46 illustrate the goggle 650 when the strap 653 is moved from a horizontal position 750 to an angled position 752. When in the horizontal position 750, shown in FIG. 45, a resultant force 760 passes through or sufficiently near the centroid 656 of the faceplate 652 of the goggle 650. Thus, when the strap 653 is in the horizontal position 750, impressive forces exerted by the faceplate 652 against the face of the wearer will be generally evenly or substantially evenly distributed across the surface of the faceplate 652. Further, in contrast to prior art designs, when the strap 653 assumes the angled position 752, as shown in FIG. 46, a resultant force 762 will be oriented through or sufficiently near the centroid 656 of the faceplate 652 of the goggle 650. Accordingly, as with the horizontal position 750, the angled position 752 can also allow forces exerted by the faceplate 652 against the face of the wearer to be generally evenly distributed across the surface of the faceplate 652.

The retention component taught herein can provide excellent ballistic resistance for the lens and the frame of the eyewear. The retention component can be integrated into, carried, or supported by the frame of the eyewear. The retention component can also be integrated into, carried, or supported by the lens or lenses supported by the frame. The retention component can also be formed as a separate part that can be retrofitted onto existing eyewear. In some embodiments, the retention component can restrict rotational and/or sliding movement of the lens relative to the frame at one or more points of the engagement between the lens and the frame. Further, the retention component can comprise a portion of the frame and/or a portion formed separately from the frame that engages with a portion of the lens.

Some of the embodiments discussed herein provide for a retention component that performs the function of engaging the frame separately from the function of engaging the lens. However, the retention component can engage both the frame and the lens together. For example, the retention component can engage a protrusion of the frame onto which the lens is mounted, thus engaging the frame and engaging and restricting movement of the lens.

Embodiments of the eyewear disclosed herein can tend to ensure that the lens does not become substantially separated from the frame in response to a ballistic event. Further, embodiments of the eyewear can be configured such that any force transmitted to the lens is also transmitted to the frame of the eyewear while substantially maintaining engagement between the lens and the frame. For example, although the lens of such eyewear may be damaged (cracked or chipped), the lens may not be shattered or displaced relative to the frame. This ballistic resistance can provide excellent protection to the wearer.

Additionally, the retention component can comprise a resilient material, such as a compressible or flexible material disposed at least along a portion of the retention component. For example, a tab, connector, body, or other structure or component of the retention component can be formed from and/or include one or more resilient materials. As a result, a ballistic event will not tend to result in damage at the interconnection between the retention component and the engagement portion. In some embodiments, a tab of the retention component can be formed from a resilient or flexible material or comprise a coating, layer, or one or more surface features formed from the resilient or flexible material. The retention component, such as the tab and/or the resilient or flexible material, can have a modulus of elasticity that is less than that of the lens. Further, retention component, such as the tab and/or the resilient or flexible material, can have a modulus of elasticity that is less than that of the frame. Accordingly, at least a portion of the retention component can dampen or absorb force or vibration from a ballistic event.

The eyewear can comprise a plurality of retention components that engage the lens and/or the frame to secure the lens relative to the frame. For example, a lens of the eyewear can be engaged and/or supported at two or more points along the upper edge or boundary thereof.

In an embodiment that comprises a unitary lens, the lens can be engaged and/or supported at least at both lateral sides and a central portion thereof. For example, a unitary lens may be secured to and/or supported by a frame using a first retention structure on the left side of midline and a second retention structure on the right side of midline. The retention structures can include any of the clips or other mechanisms disclosed herein. The first retention structure may be centered on a point that is within the left lateral one third of the length of the frame, measured hinge to hinge. The second retention structure may be centered on a point that is within the right lateral one third of the frame. A third retention structure may also be used, located within the central one third of the frame, preferably on the midline. Four or five or more retention structures may also be used, depending upon the desired performance. Typically, the retention structures can be symmetrically spaced apart along the length of the frame, or as a mirror image across the plane of symmetry (anatomical midline).

In an embodiment that comprises dual lenses, each lens can be engaged and/or supported by at least one retention component. For example, a dual lens may be secured to and/or supported by the frame using a first retention structure on the left side of a midline and a second retention structure on the right side of the midline. In some embodiments, a dual lens can be secured by three or more retention components, for example, at both lateral sides and a central portion thereof. Alternatively, a dual lens may be secured by a single retention component and by engagement between the dual lens and the frame, such as with a protrusion, catch, or tab that engages a recess of the frame. As with the unitary lens embodiments discussed above, typically, the retention structures can be symmetrically spaced apart along the length of the frame, or as a mirror image across the plane of symmetry (anatomical midline).

Although embodiments of these inventions have been disclosed in the context of certain examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions.

What is claimed is:

1. Eyewear comprising:
 a faceplate configured to be positioned against a wearer's head when the eyewear is worn by the wearer, the faceplate defining a centroid;
 a frame being coupled to the faceplate and being configured to support at least one lens in a field of view of a wearer, the frame comprising first and second guide slots formed along first and second sides thereof, the first and second guide slots defining a radius of curvature having a center point located along a horizontal centroidal axis, the horizontal centroidal axis passing through or sufficiently near the centroid of the faceplate; and
 a strap for securing the eyewear to the wearer's head, the strap comprising first and second ends and first and second strap engagement mechanisms attached to the respective first and second ends, the first and second strap engagement mechanisms being engageable with the first and second guide slots of the frame to transfer tensile loading of the strap to the faceplate in the form of compressive forces exerted by the faceplate against the face of the wearer, the compressive forces defining a resultant force, wherein the first and second strap engagement mechanisms are slidable within the first and second guide slots of the frame to maintain the orientation of the resultant force in a direction passing through or sufficiently near the centroid of the faceplate for substantially evenly distributing the compressive forces along a surface of the faceplate.

2. Eyewear as in claim 1, wherein the first and second guide slots define upper and lower portions, the lower portion of each guide slot comprising an enlarged opening that is wider than the upper portion, the enlarged opening configured to receive a wide end portion of the first and second strap engagement mechanisms.

3. Eyewear as in claim 2, wherein the first and second guide slots each further comprise a tooth being disposed above the lower portion of each guide slot and extending into each guide slot to define a gate, wherein the first and second strap engagement mechanisms comprise a neck extending from a body thereof, the wide end portion of the first and second strap engagement mechanisms being disposed at a distal end of the neck, the neck defining a cross-sectional profile that is less that a width of the gate in a first rotational orientation and greater than the width of the gate in a second rotational orientation.

4. Eyewear as in claim 3, wherein the second rotational orientation of the neck is achieved with the strap of the eyewear in an as-worn orientation.

5. Eyewear as in claim 1, wherein the horizontal centroidal axis is configured to be parallel or coincident with an interception axis that passes through both pupils of the eyes of the wearer.

6. Eyewear as in claim 1, wherein the first and second guide slots define a radius of curvature between at least about 10 mm and/or less than or equal to about 40 mm.

7. Eyewear as in claim 6, wherein the first and second guide slots define a radius of curvature between at least about 15 mm and/or less than or equal to about 30 mm.

8. Eyewear as in claim 7, wherein the first and second guide slots define a radius of curvature of about 20.8 mm.

9. Eyewear as in claim 1, wherein the frame comprises first and second outriggers, the first and second outriggers comprising the first and second guide slots.

10. Eyewear comprising:
   a faceplate configured to be positioned against a wearer's head when the eyewear is worn by the wearer, the faceplate defining a centroid;
   a frame being coupled to the faceplate and being configured to support at least one lens in a field of view of a wearer, the frame comprising first and second guide slots formed along first and second sides thereof, the first and second guide slots defining a radius of curvature having a center point located generally adjacent to a horizontal centroidal axis, the horizontal centroidal axis passing through or sufficiently near the centroid of the faceplate; and
   a strap for securing the eyewear to the wearer's head, the strap comprising first and second ends and first and second strap engagement mechanisms attached to the respective first and second ends, the first and second strap engagement mechanisms being engageable with the first and second guide slots of the frame to transfer tensile loading of the strap to the faceplate in the form of compressive forces exerted by the faceplate against the face of the wearer, the compressive forces defining a resultant force, wherein the first and second strap engagement mechanisms are slidable within the first and second guide slots of the frame between a first angular position and a second angular position, wherein the orientation of the resultant force passes generally through or sufficiently near the centroid of the faceplate for substantially evenly distributing the compressive forces along a surface of the faceplate when the strap is in either of the first or second angular positions.

11. Eyewear as in claim 10, wherein the first and second strap engagement mechanisms can rotate through a range of about 10 degrees below horizontal to about 40 degrees above horizontal.

12. Eyewear as in claim 10, wherein the first and second guide slots define a radius of about 20.8 mm.

* * * * *

UNITED STATES PATENT AND TRADEMARK OFFICE
CERTIFICATE OF CORRECTION

Page 1 of 1

| | |
|---|---|
| PATENT NO. | : 8,746,877 B2 |
| APPLICATION NO. | : 13/925048 |
| DATED | : June 10, 2014 |
| INVENTOR(S) | : Belbey et al. |

It is certified that error appears in the above-identified patent and that said Letters Patent is hereby corrected as shown below:

On the Title page, item [72], First Inventor line 1, Change "Fullterton," to --Fullerton,--.

In the Specification

Column 1 at line 14, Change "reference" to --reference.--.

Column 7 at line 1, Change "engagable" to --engageable--.

Column 7 at line 46, Change "that" to --than--.

Column 22 at line 50, After "a" delete "a". (Second occurrence)

In the Claims

Column 38 at line 65, Claim 3, Change "that" to --than--.

Signed and Sealed this
Tenth Day of February, 2015

Michelle K. Lee
*Deputy Director of the United States Patent and Trademark Office*